United States Patent
Young et al.

(10) Patent No.: US 9,109,022 B2
(45) Date of Patent: *Aug. 18, 2015

(54) PRODUCTION OF CARRIER-PEPTIDE CONJUGATES USING CHEMICALLY REACTIVE UNNATURAL AMINO ACIDS

(71) Applicant: The Scripps Research Institute, La Jolla, CA (US)

(72) Inventors: Travis Young, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/065,111

(22) Filed: Oct. 28, 2013

(65) Prior Publication Data

US 2014/0170704 A1 Jun. 19, 2014

Related U.S. Application Data

(63) Continuation of application No. 13/133,629, filed as application No. PCT/US2009/006500 on Dec. 9, 2009, now Pat. No. 8,609,383, which is a continuation-in-part of application No. 12/316,370, filed on Dec. 10, 2008, now abandoned, and a continuation-in-part of application No. PCT/US2008/013568, filed on Dec. 10, 2008.

(60) Provisional application No. 61/208,141, filed on Feb. 20, 2009.

(51) Int. Cl.
| | |
|---|---|
| *C07K 14/765* | (2006.01) |
| *C07K 16/00* | (2006.01) |
| *A61K 38/00* | (2006.01) |
| *C07K 16/18* | (2006.01) |
| *C07K 19/00* | (2006.01) |
| *C12N 15/81* | (2006.01) |
| *C07K 14/78* | (2006.01) |
| *C12N 15/62* | (2006.01) |
| *C12P 21/02* | (2006.01) |

(52) U.S. Cl.
CPC .............. *C07K 16/18* (2013.01); *C07K 14/765* (2013.01); *C07K 14/78* (2013.01); *C07K 19/00* (2013.01); *C12N 15/62* (2013.01); *C12N 15/815* (2013.01); *C12P 21/02* (2013.01)

(58) Field of Classification Search
CPC combination set(s) only.
See application file for complete search history.

(56) References Cited

U.S. PATENT DOCUMENTS

| | | | |
|---|---|---|---|
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 7,183,082 B2 | 2/2007 | Schultz et al. | |
| 7,199,222 B2 | 4/2007 | Shultz et al. | |
| 7,217,809 B2 | 5/2007 | Schultz et al. | |
| 7,238,510 B2 | 7/2007 | Schultz et al. | |
| 7,262,040 B2 | 8/2007 | Schultz et al. | |
| 7,385,028 B2 | 6/2008 | Miao et al. | |
| 2003/0082575 A1 | 5/2003 | Schultz et al. | |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0136513 A1 | 6/2005 | Zhang et al. | |
| 2005/0208536 A1 | 9/2005 | Schultz et al. | |
| 2005/0227318 A1 | 10/2005 | Alfonta et al. | |
| 2005/0250183 A1 | 11/2005 | Schultz et al. | |
| 2005/0272121 A1 | 12/2005 | Xie et al. | |
| 2006/0063244 A1 | 3/2006 | Schultz et al. | |
| 2006/0073507 A1 | 4/2006 | Deiters et al. | |
| 2006/0110784 A1 | 5/2006 | Deiters et al. | |
| 2006/0110796 A1 | 5/2006 | Schultz et al. | |
| 2006/0134746 A1 | 6/2006 | Deiters et al. | |
| 2006/0160175 A1 | 7/2006 | Anderson et al. | |
| 2006/0177900 A1 | 8/2006 | Anderson et al. | |
| 2006/0217532 A1 | 9/2006 | Miao et al. | |
| 2006/0246509 A1 | 11/2006 | Deiters et al. | |
| 2007/0009990 A1 | 1/2007 | Alfonta et al. | |
| 2007/0020634 A1 | 1/2007 | Anderson et al. | |
| 2007/0042461 A1 | 2/2007 | Anderson et al. | |
| 2007/0111193 A1 | 5/2007 | Zhang et al. | |
| 2007/0117184 A1 | 5/2007 | Schultz et al. | |
| 2007/0154952 A1 | 7/2007 | Chin et al. | |
| 2007/0160598 A1 | 7/2007 | Dennis et al. | |

(Continued)

FOREIGN PATENT DOCUMENTS

| | | |
|---|---|---|
| WO | WO 02/085923 A2 | 10/2002 |
| WO | WO 2004/094503 A1 | 11/2004 |

(Continued)

OTHER PUBLICATIONS

Buckholz and Gleeson (1991) "Yeast systems for the commercial production of heterologous proteins." *Biotechnology*, 9(11): 1067-1072.

(Continued)

*Primary Examiner* — Kagnew H Gebreyesus

(74) *Attorney, Agent, or Firm* — Quine Intellectual Property Law Group, P.C.

(57) ABSTRACT

Provided are methods of making carrier polypeptide that include incorporating a first unnatural amino acid into a carrier polypeptide variant, incorporating a second unnatural amino acid into a target polypeptide variant, and reacting the first and second unnatural amino acids to produce the conjugate. Conjugates produced using the provided methods are also provided. In addition, orthogonal translation systems in methylotrophic yeast and methods of using these systems to produce carrier and target polypeptide variants comprising unnatural amino acids are provided.

21 Claims, 13 Drawing Sheets

(56) References Cited

U.S. PATENT DOCUMENTS

| | | | |
|---|---|---|---|
| 2007/0166791 | A1 | 7/2007 | Chin et al. |
| 2007/0172915 | A1 | 7/2007 | Schultz et al. |
| 2007/0178448 | A1 | 8/2007 | Tsao et al. |
| 2007/0184517 | A1 | 8/2007 | Schultz et al. |
| 2007/0202552 | A1 | 8/2007 | Sidhu et al. |
| 2007/0238152 | A1 | 10/2007 | Wang et al. |
| 2007/0281335 | A1 | 12/2007 | Ryu et al. |
| 2008/0102124 | A1 | 5/2008 | Cho et al. |
| 2010/0297693 | A1 | 11/2010 | Young et al. |

FOREIGN PATENT DOCUMENTS

| | | | |
|---|---|---|---|
| WO | WO 2004/094593 | A2 | 11/2004 |
| WO | WO 2006/068802 | A2 | 6/2006 |
| WO | WO 2007/136778 | A2 | 11/2007 |
| WO | WO 2008/066583 | A2 | 6/2008 |
| WO | WO 2009/075847 | A2 | 6/2009 |

OTHER PUBLICATIONS

Cereghino and Cregg (2000) "Heterologous protein expression in the methylotrophic yeast *Pichia pastoris*." *FEMS Microbiology Reviews*, 24(1): 45-66.

Cereghino et al. (2001) "Expression of Foreign Genes in the yeast *Pichia pastoris*." *Genetic Engineering*, 23: 157-169.

Chen et al. (2007) "An Improved System for the Generation and Analysis of Mutant Proteins Containing Unnatural Amino Acids in *Saccharomyces cerevisiae*." *Journal of Molecular Biology*, 371(1): 112-122.

Chin et al. (2002) "Addition of p-Azido-L-phenylalanine to the Genetic Code of *Escherichia coli*." *Journal of the American Chemistry Society*, 124: 9026-9027.

Chin et al. (2003) "An Expanded Eukaryotic Genetic Code." *Science*, 301(5635): 964-967.

Cos et al. (2006) "Operational strategies, monitoring and control of heterologous protein production in the methylotropic yeast *Pichia pastoris* under different promoters: A review." 5(17): 1-20.

Daly and Hearn (2005) "Expression of heterologous proteins in *Pichia pastoris*: a useful experimental tool in protein engineering and production.." *Journal of Molecular Recognition*. 18: 119-138.

Deiters et al. (2003) "Adding amino acids with novel reactivity to the genetic code of *Saccharomyces cerevisiae*." *Journal of the American Chemistry Society*, 125(39): 11782-11783.

Dirksen et al. (2006) "Nucleophilic Catalysis of Oxime Ligation." *Angewandte Chemie International Eddition English*, 45(45): 7581-7584.

Hendrickson et al. (2004) "Incorporation of Nonnatural Amino Acids Into Proteins." *Annual Review of Biochemistry*, 73: 147-176.

Higgins (2000) "Overview of Protein Expression in *Pichia pastoris*." *Current Protocols in Protein Science*, 5.7.1-5.7.18.

Invitrogen (2009) "Multi-Copy *Pichia* Expression Kit," User Manual for the Isolation and Expression of Recombinant Proteins from *Pichia pastoris* Strains Containing Multiple Copies of a Particular Gene by Invitrogen Life Technologies.

Kupcsulik and Sevella (2005) "Optimization of Specific Product Formation Rate by Statistical and Formal Kinetic Model Descriptions of an HAS Producing *Pichia pastoris* Mut$^s$Strain." *Chemical and Biochemical Engineering Quarterly*, 19(1): 99-108.

Lemke et al. (2007) "Control of protein phosphorylation with a genetically encoded photocaged amino acid." *Nature Chemical Biology*, 3(12): 769-772.

Li et al. (2006) "Optimization of humanized IgGs in glycoengineered *Pichia pastoris*." *Nature Biotechnology*, 24: 210-215.

Neundorf et al. (2008) "Detailed Analysis Concerning the Biodistribution and Metabolism of Human Calcitonin-Derived Cell-Penetrating Peptides." *Bioconjugate Chem.*, 19: 1596-1603.

Ohya et al. (2005) "Optimization of human serum albumin production in methylotropic yeast *Pichia pastoris* by repeated fed-batch fermentation." *Biotechnology and Bioengineering*. 90(7): 876-887.

PCT Search Report and Written Opinion, dated Oct. 29, 2010 for Application No. PCT/US2009/006500.

Shen et al. (1998) "A strong nitrogen sourse-regulated prompter for controlled expression of forein genes in the yeast *Pichia pastois*." *Gene*, 216(1): 93-102.

Sreekirshna et al. (1989) "High-level expression, purification, and characterization of recombinant human tumor recrosis factor synthesized in the methylotropic yease *Pichia pastoris*." *Biochemistry* 28(9): 4117-4125.

Summerer et al. (2006) "A Genetically Encoded Fluorescent Amino Acid. " *Proceedings of the National Academy of Sciences, USA*, 103(26): 9785-9789.

Wang and Wang (2008) "New methods enabiling efficient incorporation of unnatural amino acids in yeast." *Journal of the American Chemistry Society*, 130(19): 6066-6067.

Wang et al. (2002) "Addition of the keto functiona; group to the genetic code of Escheri." *Proceedings of the National Academy of Sciences, USA*, 100(1): 56-61.

Xie et al. (2005) "Adding Amino Acids to the Genetic Repertoire." *Current Opinion in Chemical Biology*, 9: 548-554.

Young et al. (2009) "Expanding the Genetic Repertoire of the Methylotrophic Yease *Pichia pastoris* dagger." *Biochemistry*, 48(12): 2643-2653.

Ambrogelly et al. (2007) "Pyrrolysine in not hardwired for cotranslational insertion at UAG codons." *Proceedings of the International Academy of Sciences, USA*, 104(9): 3141-3146.

De Montigny et al. (2000) "Genomic Exploration of the Hemiascomycetous Yeases: 15. *Pichia soritophila*." *FEBS Letters*, 487: 87-90.

Hani and Feldmann (1998) "tRNA genes retroelements in the yeast genome." *Nucleic Acids Research*, 26(3): 689-696.

Kim et al. (2003) "Development and Characterization of a Glucagon-Like Peptide 1-Albumin Conjugate." *Diabetes*, 52: 751-759.

Kratz (2008) "Albumin as a drug carrier: Design of prodrugs, drug conjugates and nanoparticles." *Journal of Controlled Release*, 132: 171-183.

Rodriguez et al. (2007) "Improved amber and opal suppressor tRNAs for incorporation of unnatural amino acids in vivo. Part 1: Minimizing misacylation." *RNA*, 13: 1703-1714.

Rodriguez et al. (2007) "Improved amber and opal suppressor tRNAs for incorporation of unnatural amino acids in vivo. Part 2: Evaluating supression." *RNA*, 13: 1715-1722.

Search Report from European Application No. 09832243.1, dated Feb. 4, 2013.

Strable et al. (2008) "Unnatural Amino Acid Incorporation into Virus-Like Particles." *Bioconjugate Chem*, 19: 866.

Veronese and Pasut (2005) "PEGylation, successful approach to drug delivery." *Drug Discovery Today*, 10(21): 1451-1458.

Clare, et al. (1991) "High-level expression of tetanus toxin fragment C in *Pichia pastoris* strains containing multiple tandem integrations of the gene." *Biotechnology*, 9(5):455-460.

Office Action dated Jun. 20, 2014 for related Indian application No. 4071/CHEN/2010 (corresponding to international application No. PCT/US2008/013568).

Office Action dated Jul. 8, 2014 for related Japanese application No. 2010-537955 (corresponding to international application No. PCT/US2008/013568).

Office Action dated Nov. 15, 2014, for related Chinese application No. 200980156791, including English translation. (corresponding to international application No. PCT/US2009/006500).

Cregg, et al. (2000) "Recombinant protein expression in *Pichia pastoris*." Mol Biotechnol, 16: 23-52. (Cited in Office Action dated Nov. 15, 2014, for related Chinese application No. 200980156791).

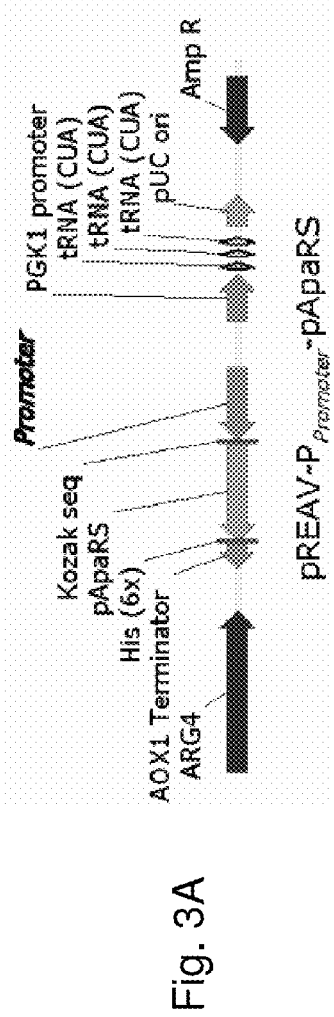
Fig. 3A
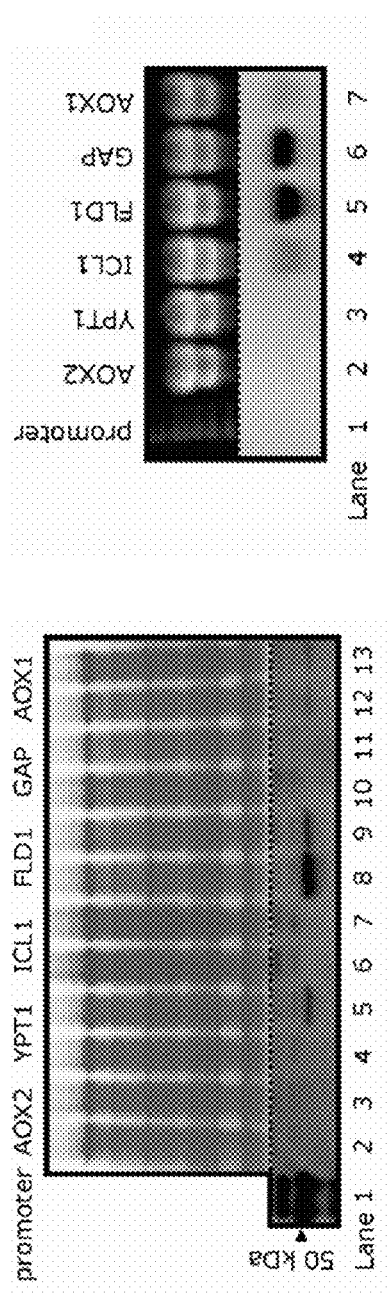
Fig. 3B
Fig. 3C

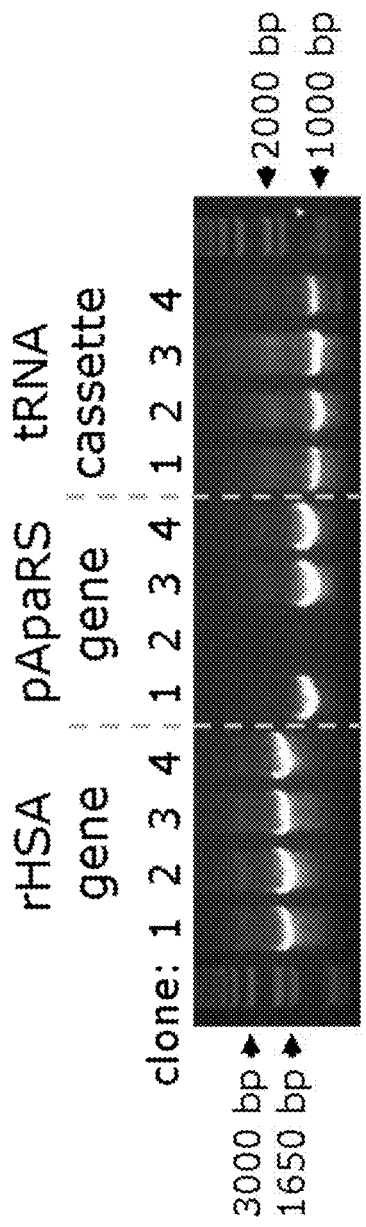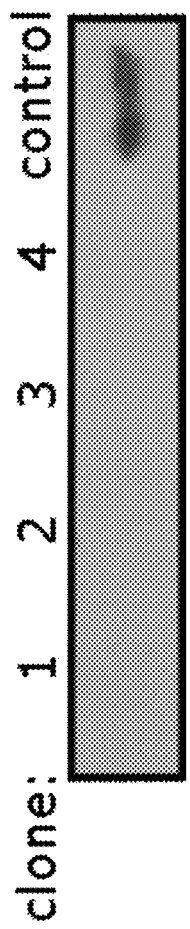
Fig. 7
Fig. 8

| Primer name | Sequence |
|---|---|
| –BglII 1F | 5'-GAC AGA CCT TAC CAA AGT CCA CAC GGA ATG CTG CCA TG-3' |
| –BglII 1R | 5'-GGT AAG TCT GTC ACT AAC TTG GAA ACT TCT GCA AAA CTC AGC TTT GGG-3' |
| –BglII 2F | 5' CAT GGA GAC CTG CTT GAA TGT GCT GAT GAC AGG GCG G 3' |
| –BglII 2R | 5'-CAA GCA GGT CTC CAT GGC AGC ATT CCG TGT GGA C-3' |
| Glu37 F' | 5'-GAT TGC CTT TGC TCA GTA TCT TCA GCA GTG TCC ATT TTA GGA TCA T-3' |
| Glu37 R' | 5'-GTT TTT GCA AAT TCA GTT ACT TCA TTC ACT AAT TTT ACA TGA TCC TAA AAT GG-3' |
| HSA Forward | 5'-ATC CGA GGA TCC AAA CGA TGA AGT GGG TAA CCT TTA TTT CCC TTC TTT TTC-3' |
| HSA Reverse | 5' GCT AAC GAA TTC ATT ATA AGC CTA AGG CAG CTT GAC TTG CAG C 3' |
| pESC F | 5'-TAC CAC TAG AAG CTT GGA GAA AAT ACC GCA TCA GGA AAT TGT AAA CGT-3' |
| pESC R | 5'-GTG AGG CAG GTA CCG TTC TGT AAA AAT GCA GCT CAG ATC TTG TTT G-3' |
| ARG4 F new | 5'-AAA TAT GGT ACC TGC CCT CAC GCT GGT TAC GGT-3' |
| ARG4 R new | 5'-CAT TTC AAG CTT CTA GTG GTA GCA ATT CTG TAC CGG TTT AC-3' |
| KETO-Koz-F | 5'-TTC TGA GAA TTC ACC ATG GCA AGC AGT AAC TTG ATT AAA CAA TTG C-3' |
| KetoRS R 6xHis | 5'-TAG GCT CGG CCG CTT AGT GGT GGT GGT GGT GGT GTT CCA GCA AAT CAG ACG AGT AAT CTT TTA C-3' |
| pESC-AOX-KETO F | 5'-ATC GTA CTT AAG GAA AGC GTA CTC AAA CAG ACA ACC ATT TCC-3' |
| pESC-AOX-KETO R | 5'-TTC TCA GGC GCG CCA TCG CCC TTC CCA ACA GTT GCG-3' |
| pPIC-keto AOX5 F | 5'-ATC GTA CTT AAG AGA TCT AAC ATC CAA AGA CGA AAG GTT GAA TGA AAC-3' |
| pPIC-keto AOXTT R | 5'-TGC ACA GGC GCG CCA AGC TTG CAC AAA CGA ACT CT CAC TTA ATC TTC-3' |
| PAOX2 F | 5'-GTA TCG CTT AAG TCC AAG ATA GCC TAT TTT TGT CGC ATA AAT TTT TGT C-3' |
| PAOX2 R | 5'-CGT TAG CCA TGG TTT TCT CAG TTG ATT GTT TTG TGG GGA TTT AGT AAG TCG-3' |
| PYPT1 F | 5'-GTA TCG CTT AAG CAT ATG ATG AGT CAC AAT CTG CTT CCA CAG ACG AG-3' |
| PYPT1 R | 5'-CGT TAG CCA TGG GAC TGC TAT TAT CTC TGT GTG TAT GTG TGT ATT GGG C-3' |
| PICL1 F | 5'-GTA TCG CTT AAG GAA TTC GGA CAA ATG TGC TGT TCC GGT AGC TTG-3' |
| PICL1 R | 5'-CGT TAG CCA TGG TCT TGA TAT ACT TGA TAC TGT GTT CTT GAA TTG AAA G-3' |
| PFLD1 F | 5'-GTA TCG CTT AAG GCA TGC AGG AAT CTC TGG CAC GGT GCT AAT GG-3' |
| PFLD1 R | 5'-CGT TAG CCA TGG TGT GAA TAT CAA GAA TTG TAT GAA CAA GCA AGT TG G-3' |
| PGAP1 F | 5'-GTA TCG CTT AAG GGA TCC TTT TTT GTA GAA ATG TCT TGG TGT CCT CGT C-3' |
| PGAP1 R | 5'-CGT TAG CCA TGG TGT GTT TTG ATA GTT GTT CAA TTG ATT GAA ATA GGG AC-3' |
| Leu tRNA F | 5'-AAG GAA GCT AGC CTC TTT TTC AAT TGT ATA TGT G-3' |
| Leu tRNA R | 5'-CGT ACA CGC GTC TGT ACA GAA AAA AAA GAA AAA TTT G-3' |
| LeuRS F | 5'-ATT CAC ACC ATG GAA GAG CAA TAC CGC CCG GAA GAG-3' |
| LeuRS R | 5'-TTA ATT CGC GGC CGC TTA GCC AAC GAC CAG ATT GAG GAG TTT ACC TG-3' |

Fig 14

PRODUCTION OF CARRIER-PEPTIDE CONJUGATES USING CHEMICALLY REACTIVE UNNATURAL AMINO ACIDS

CROSS-REFERENCE TO RELATED APPLICATIONS

This application is a continuation of U.S. Ser. No. 13/133,629 filed Jul. 8, 2011, now allowed, which is a 371 application of PCT/US2009/006500, filed Dec. 9, 2009, which is a continuation-in-part of U.S. patent application Ser. No. 12/316,370, entitled "IN VIVO UNNATURAL AMINO ACID EXPRESSION IN THE METHYLOTROPHIC YEAST *PICHIA PASTORIS*" by Travis Young et al., filed Dec. 10, 2008; and is a continuation-in-part of International Patent Application Serial No. PCT/US2008/013568, entitled "IN VIVO UNNATURAL AMINO ACID EXPRESSION IN THE METHYLOTROPHIC YEAST *PICHIA PASTORIS*" by Travis Young et al., filed Dec. 10, 2008; and is also related to U.S. Provisional Patent Application Ser. No. 61/208,141, entitled "Production of Carrier-Peptide Conjugates Using Chemically Reactive Unnatural Amino Acids," by Travis Young et al., filed Feb. 20, 2009; the contents of which are incorporated herein by reference in their entirety for all purposes.

STATEMENT AS TO RIGHTS TO INVENTIONS MADE UNDER FEDERALLY SPONSORED RESEARCH AND DEVELOPMENT

The invention was made with United States Government support under Grant No. DE-FG03-00ER46051 from the United States Department of Energy, Division of Materials Sciences. A portion of the work described herein was supported by grant number GM 62159 from the National Institutes of Health, and grant number ER 46051 from the Department of Energy. The United States Government has certain rights in this invention.

FIELD OF THE INVENTION

This invention relates to the field of protein chemistry. Described herein are methods for producing carrier polypeptide-target polypeptide conjugates wherein a first unnatural amino acid that has been incorporated into the carrier polypeptide variant is reacted with a second unnatural amino acid that has been incorporated into the target polypeptide variant. Compositions produced by these methods are also described.

BACKGROUND OF THE INVENTION

A variety of limitations impede the development of peptides for therapeutic use. For example, therapeutic peptides generally exhibit low stability in vivo and are often rapidly cleared, e.g., within several minutes to a few hours, via chemical or enzymatic degradation following their administration to a subject, i.e., before any therapeutic effect can be achieved. Consequently, low bioavailability can necessitate frequent administration of the peptide, often by injection, at fairly high doses to maintain activity. Such high doses can lead to undesired side effects. Furthermore, the delivery of therapeutic peptides can be restricted by the selective permeability of membrane barriers (e.g., intestinal and blood-brain barriers). To promote their delivery into cells, to increase their half-life, and/or to maintain their activities, polypeptides of interest, e.g., small therapeutic polypeptides, can be covalently coupled to carrier polypeptides, e.g., any of a variety of polypeptides that can have a high affinity for a specific ligand or group of ligands e.g., sugars, nucleosides, salts, amino acids, fatty acids, or other molecules. Carrier polypeptides typically facilitate the transport of such ligands, e.g., into subcellular compartments, in extracellular fluids (e.g., in the blood) or across cell membranes. Beneficially, carrier proteins can thus promote the delivery of covalently linked target polypeptides into cells, reduce their toxicity, and/or prolong their stability and/or activity following the administration of the carrier-target conjugate to a subject.

Current methods for chemically coupling small peptides to carrier polypeptides range from the use of non-specific reagents, e.g., glutaraldehyde or carbodiimide activated N-hydroxysuccinimide esters, to highly specific heterobifunctional crosslinkers that can circumvent the formation of carrier polypeptide-carrier polypeptide or target-polypeptide-target polypeptide conjugates. However, such reagents can only be used to modify a limited number of amino acid residues (e.g., amino acids comprising amine, keto, thiol, sulfhydryl, or carboxyl groups). Using such crosslinkers to conjugate a carrier polypeptide to a target polypeptide can perturb the conformation of the carrier polypeptide, the target polypeptide, or the resulting carrier-target polypeptide conjugate, thus decreasing the conjugate's stability, biological activity, pharmacokinetic activity, etc. Coupling reactions that make use of these crosslinking reagents can produce a heterogeneous population of carrier-polypeptide-target polypeptide conjugates, decreasing manufacturing efficiency and complicating quality control.

What are needed in the art are methods and compositions for the efficient, cost-effective, large-scale production of homogenous populations of carrier polypeptide-target polypeptide conjugates. The invention provides these and other needs, as will be apparent upon review of the following disclosure.

SUMMARY OF THE INVENTION

The invention provides methods and compositions for making carrier polypeptide-target polypeptide conjugates that can exhibit increased bioavailability, pharmacological activity, biological activity, half-life, and/or immunogenicity. The current invention utilizes the direct incorporation of first and second unnatural amino acids into carrier polypeptides and target polypeptides, respectively. The first and second unnatural amino acids present in the carrier and target polypeptide variants can then be reacted to produce the conjugates of the invention. Such conjugates can find therapeutic or pharmaceutical use, and they can be beneficially produced in a low-cost expression system that is capable of producing biologically active heterologous proteins that comprise complex posttranslational modifications.

In one aspect, the invention provides methods of making a carrier polypeptide-target polypeptide conjugate. The methods include incorporating a first unnatural amino acid residue into a carrier polypeptide during synthesis or translation of the carrier polypeptide, incorporating a second unnatural amino acid residue into a target polypeptide during synthesis or translation of the target polypeptide, and reacting the first and second residue to produce the carrier polypeptide-target polypeptide conjugate. The first and second unnatural amino acids can optionally be reacted via one or more of: an electrophile-nucleophile reaction, a ketone reaction with a nucleophile, an oxime ligation, an aldehyde reaction with a nucleophile, a reaction between a carbonyl group and a nucleophile, a reaction between a sulfonyl group and a nucleophile, an esterification reaction, a reaction between a hindered ester group and a nucleophile, a reaction between a thioester group and a nucleophile, a reaction between a stable imine group and a nucleophile, a reaction between an epoxide group and a nucleophile, a reaction between an aziridine group and a nucleophile, a reaction between an electrophile and an aliphatic or aromatic amine, a reaction between an electrophile and a hydrazide, a reaction between an electrophile and a carbohydrazide, a reaction between an electrophile and a semicarbazide, a reaction between an electrophile and a thiosemicarbazide, a reaction between an electrophile and a carbonylhydrazide, a reaction between an electrophile and a thiocarbonylhydrazide, a reaction between an electrophile and a sulfonylhydrazide, a reaction between an electrophile and a carbazide, a reaction between an electrophile and a thiocarbazide, a reaction between an electrophile and a hydroxylamine, a reaction between a nucleophile or nucleophiles such as a hydroxyl or diol and a boronic acid or ester, a transition metal catalyzed reaction, a palladium catalyzed reaction, a copper catalyzed heteroatom alkylation reaction, a cycloaddition reaction, a 1,3, cycloaddition reaction, a 2,3 cycloaddition reaction, an alkyne-azide reaction, a Diels-Alder reaction, or a Suzuki coupling reaction. In preferred embodiments, the reactions in which conjugates are produced optionally proceed with an efficiency of greater than 50%, greater than 70% or greater than 90%.

Incorporating the first unnatural amino acid into the carrier polypeptide during translation can optionally comprise providing a translation system that includes the first unnatural amino acid, an orthogonal tRNA-synthetase (O-RS), an orthogonal tRNA (O-tRNA) that is specifically aminoacylated by the O-RS with the first unnatural amino acid, and a nucleic acid encoding the carrier peptide, wherein the nucleic acid comprises a selector codon that is recognized by the O-tRNA; and translating the nucleic acid, thereby incorporating the first unnatural amino acid into the carrier polypeptide during translation. Optionally, the carrier polypeptide (or target polypeptide) can be produced during translation in a methylotrophic yeast cell, e.g., *Candida* cell, a *Hansenula* cell, a *Pichia* cell, or a *Torulopsis* cell.

In particular embodiments of the methods, incorporating the first unnatural amino acid into the carrier polypeptide results in an HSA variant comprising the first unnatural amino acid e.g., an HSA variant comprising a p-acetylphenylalanine. Optionally, the first unnatural amino acid can be incorporated into the HSA variant during translation. For example, the first unnatural amino acid can optionally be incorporated into the HSA variant at amino acid position 37, wherein numbering of amino acid position is relative to that of SEQ ID NO: 1. However, the carrier polypeptide into which the first unnatural amino acid is incorporated can optionally be or be homologous to any of a variety of polypeptides including, but not limited to, e.g., an antibody (e.g., an OKT3 antibody, an HER2 antibody, etc.), an antibody fragment (e.g., an Fc, an Fab, an scFv, etc.), an albumin, a serum albumin, a bovine serum albumin, an ovalbumin, a c-reactive protein, a conalbumin, a lactalbumin, a keyhole limpet hemocyanin (KLH), an ion carrier protein, an acyl carrier protein, a signal transducing adaptor protein, an androgen-binding protein, a calcium-binding protein, a calmodulin-binding protein, a ceruloplasmin, a cholesterol ester transfer protein, an f-box protein, a fatty acid-binding proteins, a follistatin, a follistatin-related protein, a GTP-binding protein, an insulin-like growth factor binding protein, an iron-binding protein, a latent TGF-beta binding protein, a light-harvesting protein complex, a lymphocyte antigen, a membrane transport protein, a neurophysin, a periplasmic binding protein, a phosphate-binding protein, a phosphatidylethanolamine binding protein, a phospholipid transfer protein, a retinol-binding protein, an RNA-binding protein, an s-phase kinase-associated protein, a sex hormone-binding globulin, a thyroxine-binding protein, a transcobalamin, a transcortin, a transferrin-binding protein, and/or a vitamin d-binding protein.

In certain embodiments of the methods, incorporating a second unnatural amino acid into the target polypeptide results in a TSP-1 variant comprising the second unnatural amino acid, e.g., a TSP-1 variant comprising a ε-(2-(aminooxy)acetyl)-L-lysine. The ε-(2-(aminooxy)acetyl)-L-lysine can optionally be incorporated into the TSP-1 variant at amino acid position 6 or at amino acid position 1, wherein numbering of amino acid position is relative to that of SEQ ID NO: 2. In other embodiments of the methods, incorporating a second unnatural amino acid into the target polypeptide results in an ABT-510 variant comprising the second unnatural amino acid, e.g., an ABT-510 variant comprising a ε-(2-(aminooxy)acetyl)-L-lysine. The ε-(2-(aminooxy)acetyl)-L-lysine can optionally be incorporated into the ABT-510 variant at amino acid position 6 or at amino acid position 1, wherein numbering of amino acid position is relative to that of SEQ ID NO: 3. Optionally, the ε-(2-(aminooxy)acetyl)-L-lysine is incorporated into the TSP-1 variant or the ABT-510 variant during synthesis. However, the target polypeptide(s) into which a second unnatural amino acid is incorporated can optionally be or be homologous to, e.g., a TSP-1, an ABT-510, a glugacon-like peptide-1 (GLP-1), a parathyroid hormone (PTH), a ribosome inactivating protein (RIP), an angiostatin, an Exedin-4, an apoprotein, an atrial natriuretic factor, an atrial natriuretic polypeptide, an atrial peptide, a C—X—C chemokine, a T39765, a NAP-2, an ENA-78, a gro-a, a gro-b, a gro-c, an IP-10, a GCP-2, a NAP-4, an a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, a RANTES, an I309, an R83915, an R91733, a T58847, a D31065, a T64262, a CD40 ligand, a complement inhibitor, a cytokine, an epithelial neutrophil activating peptide-78, a GROα, a MGSA, a GROβ, a GROγ, a MIP1-α, a MIP1-β, an MCP-1, an epithelial neutrophil activating peptide, an erythropoietin (EPO), an exfoliating toxin, a fibroblast growth factor (FGF), an FGF21, a G-CSF, a gonadotropin, a growth factor, a Hirudin, an LFA-1, a human insulin, a human insulin-like growth factor (hIGF), an hIGF-I, an hIGF-II, a human interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a leukemia inhibitory factor, a neurturin, a PDGF, a peptide hormone, a pleiotropin, a pyrogenic exotoxin A, a pyrogenic exotoxin B, a pyrogenic exotoxin C, a relaxin, a somatostatin, a superoxide dismutase, a thymosin alpha 1, a human tumor necrosis factor (hTNF), a human tumor necrosis factor alpha, a human tumor necrosis factor beta, a Ras, a Tat, an inflammatory molecule, a signal transduction molecule, a bovine pancreatic trypsin inhibitor (BPTI), and/or a BP320 antigen, wherein the target polypeptide comprises the second unnatural amino acid. It will be appreciated that the preceding list is not intended to be limiting on the embodiments herein.

For example, using the methods described above, a p-acetylphenylalanine can be incorporated into an HSA variant at amino acid position 37 during translation, wherein the numbering of amino acid position in the HSA is relative to SEQ ID NO: 1, a ε-(2-(aminooxy)acetyl)-L-lysine can be incorporated into a TSP-1 variant at amino acid position 6 during synthesis, wherein the numbering of the amino acid position in the TSP-1 is relative to SEQ ID NO: 2, and the p-acetylphenylalanine and the ε-(2-(aminooxy)acetyl)-L-lysine can be reacted via oxime ligation to produce an HSA-TSP-1 conjugate. Optionally, using the methods described above, a p-acetylphenylalanine can be incorporated into an HSA variant at amino acid position 37 during translation, wherein the numbering of amino acid position in the HSA is relative to SEQ ID NO: 1, a ε-(2-(aminooxy)acetyl)-L-lysine can be incorporated into an ABT-510 variant at amino acid position 6 during synthesis, wherein the numbering of the amino acid position in the ABT-510 is relative to SEQ ID NO: 3, and the p-acetylphenylalanine and the ε-(2-(aminooxy)acetyl)-L-lysine can be reacted via oxime ligation to produce an HSA-ABT-510 conjugate In a related aspect, the invention provides carrier polypeptide-target polypeptide conjugates produced by the methods described above. Optionally, a carrier polypeptide-target polypeptide conjugate of the invention displays a longer serum half-life than the target polypeptide. A conjugate of the invention can optionally include any one or more of the carrier polypeptides described above and any one or more of the target polypeptides described above. However, it will be appreciated that the conjugates of the invention are not limited to those comprising said carrier and target polypeptides.

The conjugate can optionally include a carrier polypeptide that is an HSA variant comprising at least a first unnatural amino acid and a target polypeptide that is a TSP-1 variant or an ABT-510 variant comprising the second unnatural amino acid. The first unnatural amino acid can optionally be a p-acetylphenylalanine that has been incorporated into, e.g., amino acid position 37 of an HSA variant, e.g., during translation, wherein the numbering of amino acid position is relative to that of SEQ ID NO: 1. The second unnatural amino acid can optionally be a ε-(2-(aminooxy)acetyl)-L-lysine that has been incorporated into, e.g., amino acid position 6 of a TSP-1 variant, e.g., during synthesis, wherein the numbering of amino acid position is relative to that of SEQ ID NO:2. The second unnatural amino acid can optionally be a ε-(2-(aminooxy)acetyl)-L-lysine that has been incorporated into, e.g., amino acid position 6 of an ABT-510 variant, e.g., during synthesis, wherein the numbering of amino acid position is relative to that of SEQ ID NO: 3.

For example, a conjugate of the invention can comprise a carrier polypeptide that is an HSA variant comprising a p-acetylphenylalanine at amino acid position 37, wherein the numbering of amino acid position is relative to that of SEQ ID NO: 1, and a target polypeptide that is a TSP-1 variant comprising a ε-(2-(aminooxy)acetyl)-L-lysine at amino acid position 6, wherein the numbering of amino acid position is relative to that of SEQ ID NO: 2. Alternatively, a conjugate of the invention can comprise a carrier polypeptide that is an HSA variant comprising a p-acetylphenylalanine at amino acid position 37, wherein the numbering of amino acid position is relative to that of SEQ ID NO: 1, and a target polypeptide that is an ABT-510 variant comprising a ε-(2-(aminooxy)acetyl)-L-lysine at amino acid position 6, wherein the numbering of amino acid position is relative to that of SEQ ID NO: 3. In these embodiments, the conjugate is produced by reacting the p-acetylphenylalanine and the ε-(2-(aminooxy)acetyl)-L-lysine via oxime ligation Relatedly, the invention provides carrier polypeptide-target polypeptide conjugates that comprise a carrier polypeptide domain comprising a first unnatural amino acid residue, and a target polypeptide domain comprising a second amino acid residue, wherein the carrier polypeptide domain and the target polypeptide domain are conjugated together through the first and second unnatural amino acid residues. A carrier polypeptide domain of the conjugate can optionally comprise any of the carrier polypeptides described herein, and a target polypeptide of the conjugate can optionally comprise any one (or more) of the target polypeptide variants described herein.

In particular embodiments, the carrier polypeptide domain of a carrier polypeptide-target polypeptide conjugate comprises an HSA, the first unnatural amino acid residue is a p-acetylphenylalanine, the target polypeptide domain comprises a TSP-1, and the second unnatural amino acid residue is a ε-(2-(aminooxy)acetyl)-L-lysine. In other embodiments, the carrier polypeptide domain of a carrier polypeptide-target polypeptide conjugate comprises an HSA, the first unnatural amino acid residue is a p-acetylphenylalanine, the target polypeptide domain comprises an ABT-510, and the second unnatural amino acid residue is a ε-(2-(aminooxy)acetyl)-L-lysine. Optionally, the first unnatural amino acid residue is incorporated into a carrier polypeptide domain during translation in a methylotrophic yeast cell, e.g., a *Candida* cell, a *Hansenula* cell, a *Pichia* cell, or a *Torulopsis* cell. A carrier polypeptide and target polypeptide can optionally be covalently coupled by reacting the first and second unnatural amino acids in any one or more of the reactions described herein.

Cells comprising the carrier polypeptide-target polypeptide conjugates described herein are also provided by the invention. For example, such a cell can optionally comprise a polypeptide-target polypeptide conjugate wherein the carrier polypeptide domain of the conjugate comprises an HSA variant that comprises a first unnatural amino acid, e.g., a p-acetylphenylalanine. A cell of the invention can comprise a polypeptide-target polypeptide conjugate wherein the target polypeptide domain of the conjugate comprises a TSP-1 variant that comprises a second unnatural amino acid, e.g., a ε-(2-(aminooxy)acetyl)-L-lysine. In other embodiments, a cell of the invention can comprise a polypeptide-target polypeptide conjugate wherein the target polypeptide domain of the conjugate comprises an ABT-510 variant that comprises a second unnatural amino acid, e.g., a ε-(2-(aminooxy)acetyl)-L-lysine Kits are also a feature of the invention. For example, kits can optionally contain any one or more compositions provided by the invention. Alternatively or additionally, kits can contain reagents for the synthesis of carrier polypeptides that comprise first chemically reactive unnatural amino acids and/or target polypeptides, e.g., small therapeutic peptides, that comprise second chemically reactive unnatural amino acids. Such reagents can include, e.g., the reactive unnatural amino acids, host cells, e.g., methylotrophic yeast cells that include orthogonal translation system components suitable for the production of carrier polypeptides and/or target polypeptides comprising unnatural amino acids, solutions in which to perform ligation reactions that produce the conjugates of the invention, reagents with which to produce therapeutic formulations comprising one or more conjugates of the invention, media, etc. Kits of the invention can include additional components such as instructions to, e.g., construct a methylotrophic yeast strain that can express a carrier polypeptide and/or target polypeptide that comprises unnatural amino acids, perform a chemical ligation reaction to produce a carrier polypeptide-target polypeptide conjugate, etc. The kit can include a container to hold the kit components, instructional materials for practicing any method or any combination of methods herein, instructions for using cells (e.g., methylotrophic yeast cells) provided with the kit, e.g., to produce a carrier and/or target polypeptide of interest that comprises a chemically reactive unnatural amino acid at a selected amino acid position.

Those of skill in the art will appreciate that the methods, kits and compositions provided by the invention can be used alone or in combination. For example, the methods of the invention can be used to produce the carrier polypeptide-target polypeptide conjugates of the invention. One of skill will appreciate further combinations of the features of the invention noted herein.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an aminoacyl tRNA synthetase (RS)" optionally includes combinations of two or more RS molecules; reference to "carrier polypeptide" or "a methylotrohpic yeast cell" optionally includes, as a practical matter, a plurality of that carrier polypeptide or many methylotrophic yeast cells.

Unless defined otherwise, all technical and scientific terms used herein have the same meaning as commonly understood by one of ordinary skill in the art to which the invention pertains. Although any methods and materials similar or equivalent to those described herein can be used in the practice of or testing of the present invention, the preferred materials and methods are described herein. In describing and claiming the present invention, the following terminology will be used in accordance with the definitions set out below.

Carrier Polypeptide:

The term "carrier polypeptide" refers to any one of a variety of polypeptides that can be conjugated to a target polypeptide, e.g., using the methods provided herein. A carrier polypeptide can be beneficially used, e.g., to promote the delivery of covalently linked target polypeptides into cells, to reduce their toxicity, and/or to prolong their stability and/or activity following the administration of the carrier-target conjugate to a subject. Preferred characteristics of carrier proteins can include high solubility and long half-lives; however, it is not intended that a carrier polypeptide be limited by possessing or not possessing any particular biological activity. Commonly used carrier proteins include human serum albumin (HSA; 66 kDa), bovine serum albumin (BSA; 67 kDa), antibody fragments such as Fc (45 kDa), and keyhole limpet hemocyanin (KLH; $4.5 \times 10^5$-$1.3 \times 10^7$ Da). In one useful example described below, covalently linking the therapeutic peptide ABT-510 to the carrier polypeptide HSA can increase the peptide's serum half-life.

Carrier polypeptides can optionally be modified versions of such polypeptides, e.g., modified by inclusion of an unnatural amino acid. A carrier polypeptide into which an unnatural amino acid has been incorporated is referred to herein as a "carrier polypeptide variant."

Cognate:

The term "cognate" refers to components that function together, or have some aspect of specificity for each other, e.g., an orthogonal tRNA (O-tRNA) and an orthogonal aminoacyl-tRNA synthetase (O-RS), in which the O-RS specifically aminoacylates the O-tRNA with an unnatural amino acid.

Derived from:

As used herein, the term "derived from" refers to a component that is isolated from or made using a specified molecule or organism, or sequence information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event, e.g., caused by polymerase infidelity, and the identification of the derived polypeptide can be made by appropriate screening methods, e.g., as discussed in references cited herein. Mutagenesis of a polypeptide typically entails manipulation of the polynucleotide that encodes the polypeptide.

Encode:

As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, a DNA molecule can encode an RNA molecule, e.g., by the process of transcription incorporating a DNA-dependent RNA polymerase enzyme. Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

To Incorporate an Unnatural Amino Acid:

As used herein, "to incorporate an unnatural amino acid", e.g., into a carrier or target polypeptide, refers to the direct addition of an unnatural amino acid to a growing polypeptide chain during primary construction of the carrier or target polypeptide, e.g., via translation or chemical synthesis.

In Response to:

As used herein, the term "in response to" refers to the process in which an O-tRNA of the invention recognizes a selector codon and mediates the incorporation of an unnatural amino acid, which is coupled to the tRNA, into a growing polypeptide chain.

Non-Eukaryote:

As used herein, the term "non-eukaryote" refers to organisms belonging to the Kingdom Monera (also termed Prokarya). Non-eukaryotic organisms, e.g., prokaryotic organisms, are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera. Nevertheless, Eubacteria, Archaea, Cyanobacteria, and mycoplasma are all understood to be non-eukaryotes.

Orthogonal:

As used herein, the term "orthogonal" refers to a molecule, e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency, e.g., 45% efficiency, 50% efficiency, 60% efficiency, 70% efficiency, 75% efficiency, 80% efficiency, 90% efficiency, 95% efficiency, or 99% or more efficiency, as compared to that of a control, e.g., a corresponding tRNA/RS endogenous pair, or an active orthogonal pair.

Orthogonal Aminoacyl tRNA Synthetase:

As used herein, an orthogonal aminoacyl tRNA synthetase (O-RS) is an enzyme that preferentially aminoacylates an O-tRNA with an amino acid in a translation system of interest. The amino acid that the O-RS loads onto the O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS.

Orthogonal tRNA:

As used herein, an orthogonal tRNA (O-tRNA) is a tRNA that is orthogonal to a translation system of interest, where the tRNA is, e.g., (1) identical or substantially similar to a naturally occurring tRNA, (2) derived from a naturally occurring tRNA by natural or artificial mutagenesis, (3) derived by any process that takes a sequence of a wild-type or mutant tRNA sequence of (1) or (2) into account, (4) homologous to a wild-type or mutant tRNA; (5) homologous to any example tRNA that is designated as a substrate for an orthogonal tRNA synthetase or (6) a conservative variant of any example tRNA that is designated as a substrate for an orthogonal tRNA synthetase. The O-tRNA can exist charged with an amino acid, or in an uncharged state. It is also to be understood that a "O-tRNA" optionally is charged (aminoacylated) by a cognate synthetase with an unnatural amino acid. Indeed, it will be appreciated that an O-tRNA of the invention is advantageously used to insert essentially any unnatural amino acid into a growing polypeptide, during translation, in response to a selector codon.

Polypeptide:

A polypeptide is any oligomer of amino acid residues (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acid residues. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Preferentially Aminoacylates:

As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector Codon:

The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppression Activity:

As used herein, the term "suppression activity" refers, in general, to the ability of a tRNA, e.g., a suppressor tRNA, to allow translational read-through of a codon, e.g., a selector codon that is an amber codon or a 4-or-more base codon, that would otherwise result in the termination of translation or mistranslation, e.g., frame-shifting. Suppression activity of a suppressor tRNA can be expressed as a percentage of translational read-through activity observed compared to a second suppressor tRNA, or as compared to a control system, e.g., a control system lacking an O-RS.

Suppression efficiency can be determined by any of a number of assays known in the art. For example, a β-galactosidase reporter assay can be used, e.g., a derivatized lacZ plasmid (where the construct has a selector codon in the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Suppressor tRNA:

A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon, e.g., an amber, ocher or opal codon, a four base codon, a rare codon, etc.

Target Polypeptide:

The term "target polypeptide" refers to any polypeptide of interest whose, e.g., bioavailability, pharmacological activity, biological activity, half-life, immunogenicity, etc. is maintained or improved when it is covalently linked to a carrier polypeptide. A target polypeptide can optionally be a small therapeutic peptide, e.g., TSP-1 or ABT-510. Alternatively or additionally, a target polypeptide can be immunogenic, derived from a foreign organism, a self-protein, or a synthetic polypeptide. It is not intended that a target polypeptide be limited by possessing or not possessing any particular biological activity. Examples of small therapeutic peptides that can be used with the invention include, e.g., a TSP-1 polypeptide or a derivative thereof, an ABT-510, a glugacon-like peptide-1 (GLP-1), a parathyroid hormone (PTH), Exedin-4, and many others, e.g., as noted herein.

Target polypeptides can optionally be modified versions of such polypeptides, e.g., modified by inclusion of an unnatural amino acid. A target polypeptide into which an unnatural amino acid has been incorporated is referred to herein as a "target polypeptide variant."

Translation System:

The term "translation system" refers to the components that incorporate an amino acid into a growing polypeptide chain (protein). Components of a translation system can include, e.g., ribosomes, tRNAs, synthetases, mRNA, O-RSs, O-tRNAs, and the like.

Unnatural Amino Acid:

As used herein, the term "unnatural amino acid" refers to any amino acid, modified amino acid, and/or amino acid analogue, that is not one of the 20 common naturally occurring amino acids or the rare naturally occurring amino acids e.g., selenocysteine or pyrrolysine.

Variant:

As used herein, the term "variant" refers to a polypeptide that comprises at least one chemically reactive unnatural amino acid and is typically derived from a corresponding "natural" polypeptide that contains no unnatural amino acids. For example, a carrier polypeptide variant (or target polypeptide variant) is a mutant of a "natural" carrier polypeptide (or "natural" target polypeptide), which mutant comprises a chemically reactive unnatural amino acid. The chemically reactive unnatural amino acid in a carrier polypeptide variant and/or a target polypeptide variant can optionally replace a natural amino acid in the carrier and/or target polypeptide's primary sequence. Alternatively or additionally, one (or more) unnatural amino acid can be added to the primary sequence of a carrier or target polypeptide. The chemically reactive unnatural amino acid that is incorporated into a carrier or target polypeptide variant can be a conservative or non-conservative replacement (as compared to the corresponding natural amino acid in the "natural" carrier or target polypeptide that comprises no unnatural amino acids).

BRIEF DESCRIPTION OF THE DRAWINGS

FIG. 3 shows the results of experiments that were performed to compare promoters to optimize pApaRS expression and amber suppression. (a) Linear map of pREAV-$P_{promoter}$-pApaRS illustrating the promoter region being varied. Promoters were PCR amplified from genomic DNA. (b) Two clones from each transformation of GS200-rHSA$_{E37X}$ with pREAV-$P_{promoter}$-pApaRS were grown with methanol as the primary carbon source for 6 days, lysed, and separated on an SDS-PAGE gel (top gel). The gel was stained with Coomassie to verify equal loading. Lysates were analyzed via Western blot for pApaRS-His$_{6x}$ (bottom gel). (c) The clones which produced the most protein in (b) were analyzed by Northern blot for pApaRS mRNA transcription (bottom gel). Bands for the 18s and 28s rRNA were stained with ethidium bromide (top gel) to confirm RNA integrity and equal loading.

FIG. 7 depicts the results of PCR performed on 4 transformants to determine whether pPIC3.5k and pREAV cassettes were successfully incorporated into GS200-rHSA$_{E37X}$/pREAV-$P_{ADH1}$-PApaRS.

FIG. 8 depicts western blots for pApaRS-$_{His6x}$ in four separate clones of GS200-rHSA$_{E37X}$/pREAV-$P_{ADH1}$-pApaRS from a single transformation. No pApaRS protein was detectable.

FIG. 14 provides the sequences of oligonucleotide primers that are used for strain and plasmid construction in Example 1.

DETAILED DESCRIPTION OF THE INVENTION

Overview

Figure 1A:
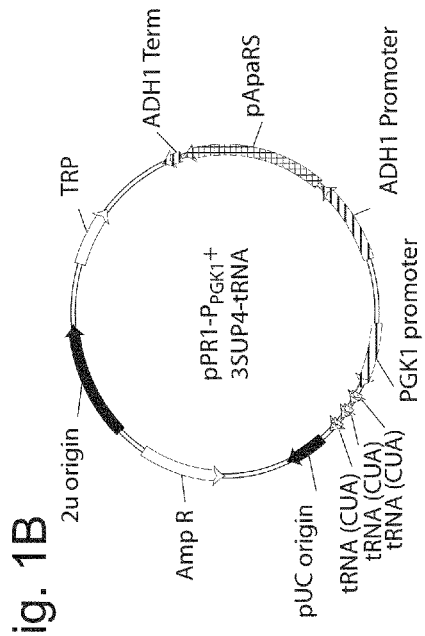
FIG. 1 provides schematic illustrations of various plasmids that find use with the invention. Vectors for amber suppression in eukaryotes illustrate selectable markers (white arrows), replication origins (black arrows), promoters and transcriptional terminator elements (vertically striped arrows), and suppressor tRNAs (tRNA(CUA)). (a) Map of the commercially available pPIC3.5K shuttle vector for in vivo multicopy incorporation and expression in *P. pastoris*. rHSA$_{E37X}$ is subcloned between the AOX1 promoter and terminator. (b). Optimized amber suppression vector for *S. cerevisiae* harboring the pApaRS/tRNA pair under $P_{ADH1}$ control. tRNA$_{CUA}$ repeats are separated by regions from the SUP4 gene (not labeled) and driven by $P_{PGK1}$. (c) Modified pPR1-$P_{PGK1}$+3SUP4-tRNA plasmid where the 2μ eukaryotic origin and TRP marker were replaced by ARG4 to create pREAV-$P_{ADH1}$-pApaRS. (d) $P_{ADH1}$ and $T_{ADH1}$ were replaced by their AOX1 counterparts to create pREAV-$P_{AOX1}$-pApaRS. (e) The first 61 amino acids of rHSA$_{E37X}$. The pre-pro leader peptide allows export of rHSA$_{E37X}$ into the media and is cleaved during transport to yield the mature protein (rHSA) beginning with an aspartic acid. The $37^{th}$ residue (X) of the mature rHSA denotes the unnatural amino acid incorporated in response to the amber codon.
Figure 1B:
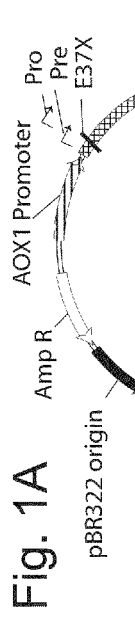

The invention provides a beneficial alternative to using currently available cross-linking reagents to produce carrier polypeptide-target polypeptide conjugates. The methods provided herein include reacting a first chemically reactive unnatural amino acid residue, which has been directly incorporated into a carrier polypeptide variant, with a second chemically reactive unnatural amino acid residue, which has been directly incorporated into a target polypeptide variant, to produce a stable, well-defined conjugate. Such conjugates can optionally find use as therapeutic agents with novel or improved biological properties, reduced toxicity, enhanced activities, and/or increased half-life. Advantageously, these methods can maximize yields and minimize costs by permitting the consistent production of homogenous populations of conjugates, e.g., that each comprise identical stoichiometries and ligation sites.

As will be apparent from the description herein, various embodiments of the invention can comprise any of a wide variety of carrier polypeptide variants that include a first reactive unnatural amino acid and any of a wide variety of target polypeptide variants that include a second reactive unnatural amino acid, wherein the first and second unnatural amino acids are reacted to form the stable, covalently linked carrier polypeptide-target polypeptide conjugate. The carrier polypeptide and/or target polypeptide can optionally be therapeutic, immunogenic, derived from a foreign organism, a self-protein, synthetic, etc. Particular carrier polypeptides of interest are described in detail hereinbelow. Target polypeptides that find use with the invention include, but are not limited to, such small therapeutic peptides as TSP-1, ABT-510, GLP-1, Exedin-4, peptide derivatives of the preceding, and others, which are described in further detail elsewhere herein.

In certain embodiments described herein, the unnatural amino acids can be site-specifically incorporated into a carrier or target polypeptide variant with high efficiency and high fidelity using orthogonal tRNA/aminoacyl-tRNA synthetase pairs, e.g., in methylotrophic yeast such as *P. pastoris, P. methanolica, P. angusta* (also known as *Hansenula polymorpha*), *Candida boidinii*, and *Torulopsis* spp. Methylotrophic yeast are attractive candidates for use as recombinant expression systems for heterologous, therapeutically useful proteins (Lin-Cereghino et al. (2000) "Heterologous protein expression in the methylotrophic yeast *Pichia pastoris*." FEMS Microbiol Rev 24: 45-66; International Patent Application Number PCT/US2008/013568, filed Dec. 10, 2008, entitled, "In Vivo Unnatural Amino Acid Expression in the Methylotrophic Yeast *Pichia Pastoris*"; and US Patent Application Publication 2009/0197339, filed Dec. 10, 2008, entitled, "In Vivo Unnatural Amino Acid Expression in the Methylotrophic Yeast *Pichia Pastoris*". The eukaryotic subcellular organization of methylotrophic yeast enables them to carry out many of the posttranslational folding, processing and modification events required to synthesize biologically active carrier polypeptides and/or target polypeptides derived from mammals. Unlike proteins expressed in *S. cerevisiae*, proteins produced by methylotrophic yeast such as *P. pastoris, P. methanolica, P. angusta* (also known as *Hansenula polymorpha*), *Candida boidinii*, and *Torulopsis* spp., are less likely to contain high-mannose glycan structures that can hamper downstream processing of heterologously expressed glycoproteins. In addition, carrier and/or target polypeptides synthesized in methylotrophic yeast are advantageously free of pyrogenic and antigenic compounds often characteristic of proteins expressed in *E. coli*. Most significantly, methylotrophic yeast expression systems are particularly useful for large-scale synthesis. For example, orthogonal translation systems in methylotrophic yeast can permit the expression of recombinant carrier and/or target polypeptides comprising unnatural amino acids at levels 10- to 100-fold higher than in *S. cerevisiae*, bacterial, insect, or mammalian systems. In addition, methylotrophic yeast can be easily cultured in a simple, defined salt medium, eliminating the need for the expensive media supplements and equipment that are required for baculovirus expression systems. Further details regarding the use of orthogonal translation systems in methylotrophic yeast can be found in International Patent Application Number PCT/US2008/013568, filed Dec. 10, 2008, entitled, "In Vivo Unnatural Amino Acid Expression in the Methylotrophic Yeast *Pichia Pastoris*" and US Patent Application Publication 2009/0197339, filed Dec. 10, 2008, entitled, "In Vivo Unnatural Amino Acid Expression in the Methylotrophic Yeast *Pichia Pastoris*".

First and second unnatural amino acids can be directly incorporated into carrier and target polypeptides, respectively, using any of a number of methods known in the art. While many embodiments utilize orthogonal translation systems, e.g., in *P. pastoris* (see below) or other methylotrophic yeast (e.g., *P. methanolica, P. angusta* (or *Hansenula polymorpha*), *Candida boidinii*, and *Torulopsis* spp), as the route of direct incorporation of the unnatural amino acids, other direct incorporation methods (e.g., in vitro translation systems, solid-phase synthesis, etc.) can also optionally be used. It will be appreciated that in typical embodiments herein, an unnatural amino acid is incorporated into a carrier and/or target polypeptide during construction of the polypeptide and is not added via post-translational chemical derivatization.

In one illustrative example, the invention provides methods and compositions useful for the production of an HSA-ABT-510 conjugate. ABT-510 is an antiangiogenic peptide mimetic derived from human thrombospondin that exhibits potent antitumor activity in humans, but which suffers from rapid clearance by the kidneys when administered intravenously (Hoekstra et al. (2005) "Phase I safety, pharmacokinetic, and pharmacodynamic study of the thrombospondin-1-mimetic angiogenesis inhibitor ABT-510 in patients with advanced cancer." *J Clin Oncol* 23: 5188-5197; Yang et al. (2007) "Thrombospondin-1 peptide ABT-510 combined with valproic acid is an effective antiangiogenesis strategy in neuroblastoma." *Cancer Res* 67: 1716-1724; Reiher et al. (2002) "Inhibition of tumor growth by systemic treatment with thrombospondin-1 peptide mimetics." *Int J Cancer* 98: 682-689). HSA is a well-characterized soluble serum protein with a half-life of 19 days, which functions primarily as a carrier protein for steroids, fatty acids, and thyroid hormones. HSA is described, for example, in entry 103600 in the Online Mendelian Inheritance in Man database (see also GenBank Accession No. AAA98797.1). A p-acetylphenylalanine residue, which has been incorporated into an HSA variant at amino acid position 37, and a $\epsilon$-(2-(aminooxy)acetyl)-L-lysine residue, which has been incorporated into an ABT-510 variant at amino acid position 6, react via selective oxime ligation to produce an HSA-ABT-510 conjugate. Conjugation to HSA can prolong the conjugated peptide's half-life, thus increasing its therapeutic utility. A p-acetylphenylalanine residue, which has been incorporated into an HSA variant at amino acid position 37, and a $\epsilon$-(2-(aminooxy)acetyl)-L-lysine residue, which has been incorporated into an ABT-510 variant at amino acid position 1 can also be reacted, via oxime ligation, to produce a useful conjugate.

The detailed description is organized to first elaborate the various carrier polypeptides and target polypeptides that can be chemically ligated using the methods and compositions provided by the invention. Next, details regarding methods of producing carrier polypeptide variants and/or target polypeptide variants comprising first and second reactive unnatural amino acids, respectively, are described. Chemical coupling reactions that can be used to conjugate a carrier polypeptide variant to a target polypeptide variant are then elaborated. Pharmaceutical compositions comprising conjugates of the invention and details regarding their administration are described thereafter. Lastly, kits comprising conjugates of the invention and/or methods of their production are described.

Carrier Polypeptides and Target Polypeptides of Interest

As described above, the invention provides methods and compositions for the production of carrier polypeptide-target polypeptide conjugates wherein first and second unnatural amino acid residues with unique chemical functionalities that have been directly incorporated into carrier polypeptides and target polypeptides, respectively, are reacted to produce a homogenous population of defined conjugates. The reactive unnatural amino acids present in carrier and target polypeptide variants can optionally be in any location within the polypeptides. Placement of the unnatural amino acids in the carrier and target polypeptide variants is optionally chosen based on, e.g., whether placement in that location would change, e.g., the conformations, biological activities, pharmacologically activities, or other relevant properties, of the carrier and/or target polypeptide variants vs. the "natural" polypeptides from which they are derived. Another criterion by which the locations of chemically reactive unnatural amino acids in carrier and target polypeptides are optionally selected is whether the locations allow the reactive unnatural amino acids to be accessible (e.g., can the two unnatural amino acids participate in a ligation reaction to produce a stable conjugate), etc.

The first and second amino acids that are incorporated into the carrier and target polypeptide variants, respectively, can be conservative or non-conservative replacements (as compared to the corresponding natural amino acids in the "natural" carrier and target polypeptides that comprise no unnatural amino acids). A chemically reactive unnatural amino acid in a carrier polypeptide and/or a target polypeptide can optionally replace a natural amino acid in the carrier and/or target polypeptide's primary sequence. Alternatively or additionally, one (or more) reactive unnatural amino acids can be added to the primary sequence of a carrier or target polypeptide.

The carrier and target polypeptides that include the first and second reactive unnatural amino acids, respectively, can be constructed in any of a number of methods that entail the direct incorporation of an unnatural amino acid into a growing polypeptide chain. While many embodiments utilize orthogonal translation in, e.g., *P. pastoris* (see below) or other methylotrophic yeast such as *P. methanolica, P. angusta* (also known as *Hansenula polymorpha*), *Candida boidinii*, and *Torulopsis* spp., as the route of direct incorporation of the unnatural amino acids, other direct incorporation methods (e.g., in vitro translation systems, solid-phase synthesis, etc.) can also optionally be used, or the methods can be used in combination. However, advantages to expression in methylotrophic yeast include their ease of genetic manipulation, their economy of recombinant protein production, and their abilities to perform complex posttranslational modifications typically associated with eukaryotic proteins. These and other advantages of recombinant protein expression in methylotrophic yeast are explained in further detail below.

In certain embodiments, a carrier polypeptide can be conjugated to more than one target polypeptide, e.g., using one or more of the ligation chemistries described herein, to produce, e.g., a therapeutically useful carrier-target conjugate such as a multiple antigen peptide (MAP). Conversely, a target polypeptide can optionally be conjugated to multiple carrier polypeptides.

HSA and ABT-510 were chosen as the carrier polypeptide and target polypeptide, respectively, to illustrate aspects of the current invention. HSA is a well-characterized serum protein with a serum half-life of 19 days, and ABT-510, a peptide derivative of the natural angiogenic inhibitor thrombospondin-1, exhibits potent antitumor activity in humans but suffers from rapid clearance by the kidneys when administered intravenously (Hoekstra et al. (2005) "Phase I safety, pharmacokinetic, and pharmacodynamic study of the thrombospondin-1-mimetic angiogenesis inhibitor ABT-510 in patients with advanced cancer." *J Clin Oncol* 23: 5188-5197; Yang et al. (2007) "Thrombospondin-1 peptide ABT-510 combined with valproic acid is an effective antiangiogenesis strategy in neuroblastoma." *Cancer Res* 67: 1716-1724; Reiher et al. (2002) "Inhibition of tumor growth by systemic treatment with thrombospondin-1 peptide mimetics." *Int J Cancer* 98: 682-689). As described in the Example below, a p-acetylphenylalaine that has been incorporated into an HSA or an HSA variant can be reacted with a ε-(2-(aminooxy)acetyl)-L-lysine that has been incorporated into an ABT-510 or ABT-510 variant, e.g., via oxime ligation. It will be appreciated that the illustrations in the Example below are not the only embodiments of the invention. As will be apparent from the description herein, various embodiments of the invention can comprise any of a wide variety of carrier polypeptide variants that include a first reactive unnatural amino acid and any of a wide variety of target polypeptide variants that include a second reactive unnatural amino acid, wherein the first and second unnatural amino acids are reacted to form a stable, covalently linked carrier polypeptide-target polypeptide conjugate. Thus, in various embodiments, the carrier polypeptide and/or target polypeptide can optionally be therapeutic, immunogenic, derived from a foreign organism, a self-protein, synthetic, etc. Particular carrier and target polypeptides of interest are described below.

Carrier Polypeptides of Interest

As described elsewhere herein, a carrier protein can be beneficially linked to a target polypeptide, e.g., a therapeutic peptide such as ABT-510, using the methods provided be the invention, in order to, e.g., promote the target polypeptide's delivery into cells, to increase its serum half-life, to maintain stabilize its activity, to prevent its aggregation following administration to a subject, etc. Preferred characteristics of a carrier protein can include high solubility and a long half-life; however, it is not intended that a carrier polypeptide used in the invention be limited by possessing or not possessing any particular biological activity.

The carrier polypeptide can optionally comprise, be, or be homologous to, e.g., an antibody (e.g., an OKT3 antibody, a HER2 antibody, etc.), an antibody fragment (e.g., an scFv, an Fab, an Fc, etc.), an albumin, a serum albumin, a bovine serum albumin, an ovalbumin, a c-reactive protein, a conalbumin, a lactalbumin, a keyhole limpet hemocyanin (KLH), an ion carrier protein, an acyl carrier protein, a signal transducing adaptor protein, an androgen-binding protein, a calcium-binding protein, a calmodulin-binding protein, a ceruloplasmin, a cholesterol ester transfer protein, an f-box protein, a fatty acid-binding proteins, a follistatin, a follistatin-related protein, a GTP-binding protein, an insulin-like growth factor binding protein, an iron-binding protein, a latent TGF-beta binding protein, a light-harvesting protein complex, a lymphocyte antigen, a membrane transport protein, a neurophysin, a periplasmic binding protein, a phosphate-binding protein, a phosphatidylethanolamine binding protein, a phospholipid transfer protein, a retinol-binding protein, an RNA-binding protein, an s-phase kinase-associated protein, a sex hormone-binding globulin, a thyroxine-binding protein, a transcobalamin, a transcortin, a transferrin-binding protein, or a vitamin D-binding protein.

However, it will be appreciated that the methods and compositions of the invention are not limited to the polypeptides listed above. A carrier polypeptide-target polypeptide conjugate of the invention can optionally comprise any carrier polypeptide well known in the art Target Polypeptides of Interest Target polypeptides can include any polypeptide of interest whose half-life, pharmacological activity, biological activity, bioavailability can be stabilized or improved by the chemical ligation of the target polypeptide to a carrier protein. Target polypeptides can optionally be therapeutic, immunogenic, derived from a foreign organism, a self-protein, synthetic, etc. In particularly useful embodiments, a target polypeptide can be a small therapeutic peptide (see below). However, it is not intended that a target polypeptide be limited by possessing or not possessing any particular biological activity. In embodiments herein, a target polypeptide can comprise, be a variant of, or be homologous to, e.g., a TSP-1, an ABT-510, a glugacon-like peptide-1 (GLP-1), a parathyroid hormone (PTH), an Exedin-4, a ribosome inactivating protein (RIP), an angiostatin, an apoprotein, an atrial natriuretic factor, an atrial natriuretic polypeptide, an atrial peptide, a C—X—C chemokine, a T39765, a NAP-2, an ENA-78, a gro-a, a gro-b, a gro-c, an IP-10, a GCP-2, a NAP-4, an a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, a RANTES, an I309, an R83915, an R91733, a T58847, a D31065, a T64262, a CD40 ligand, a complement inhibitor, a cytokine, an epithelial neutrophil activating peptide-78, a GROα, a MGSA, a GROβ, a GROγ, a MIP1-α, a MIP1-β, an MCP-1, an epithelial neutrophil activating peptide, an erythropoietin (EPO), an exfoliating toxin, a fibroblast growth factor (FGF), an FGF21, a G-CSF, a gonadotropin, a growth factor, a Hirudin, an LFA-1, a human insulin, a human insulin-like growth factor (hIGF), an hIGF-I, an hIGF-II, a human interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a leukemia inhibitory factor, a neurturin, a PDGF, a peptide hormone, a pleiotropin, a pyrogenic exotoxin A, a pyrogenic exotoxin B, a pyrogenic exotoxin C, a relaxin, a somatostatin, a superoxide dismutase, a thymosin alpha 1, a human tumor necrosis factor (hTNF), a human tumor necrosis factor alpha, a human tumor necrosis factor beta, a Ras, a Tat, an inflammatory molecule, a signal transduction molecule, a bovine pancreatic trypsin inhibitor (BPTI), or a BP320 antigen. Again, it will be appreciated that the methods and compositions of the invention are not limited to those target polypeptides listed above.

Methods of Producing Carrier Polypeptide Variants and/or Target Polypeptide Variants The carrier polypeptide variants and/or target polypeptide variants, e.g., that are to be reacted to produce the conjugates of the invention, can be produced using any of a variety of methods that entail the direct incorporation of an unnatural amino acid into a growing polypeptide chain. Thus, while the description and the examples primarily focus on the use of orthogonal translation systems in methylotrophic yeast, e.g., *P. pastoris* (see below), *P. methanolica, P. angusta* (also known as *Hansenula polymorpha*), *Candida boidinii*, and *Torulopsis* spp., to incorporate chemically reactive first and second unnatural amino acids into carrier polypeptide variants and target polypeptide variants, respectively, other orthogonal translation systems and/or other non-orthogonal direct incorporation methods can optionally be used to produce the target and carrier polypeptide variants that comprise such unnatural amino acids. In several embodiments, a chemically reactive unnatural amino acid can be incorporated into a carrier polypeptide variant or a target polypeptide variant, e.g., a small therapeutic peptide, while the polypeptide is being made, e.g., during translation using O-tRNA/O-RS pairs, during in vitro synthesis using chemico-synthetic methods, etc. Therefore, while particular methods of constructing carrier and/or target polypeptide variants that comprise unnatural amino acids are detailed herein, e.g., using orthogonal translation systems in methylotrophic yeast, they such should not necessarily be taken as limiting. Other methods in which unnatural amino acids are directly incorporated into carrier and/or polypeptides during primary assembly are also included herein in the many embodiments.

Following incorporation of the reactive first and second unnatural amino acids into a carrier polypeptide and target polypeptide, respectively, e.g., using any of the methods detailed hereinbelow, the first unnatural amino acid present in the carrier polypeptide variant can be reacted with the second unnatural amino acid present in the target polypeptide variant, e.g., via any one of the ligation chemistries described elsewhere herein, to form a stable, defined conjugate.

It will be appreciated that genetic incorporation of unnatural amino acids into carrier polypeptides and target polypeptides (e.g., through orthogonal translation systems such as those described and referenced to herein) prior to the formation of stable carrier polypeptide-target polypeptide conjugates can, in some embodiments, offer benefits over generation of carrier polypeptide-target polypeptide conjugates using methods that are currently available. For example, one current methodology for conjugation of target polypeptides to the carrier HSA involves exploitation of its single free cysteine (residue 34) via maleimide linkages. This strategy has several drawbacks, including the antigenicity of maleimide and the frequent modification of cysteine 34 by endogenous nitric oxide, free cysteine, glutathione, or sugars, which can lead to variable coupling efficiency.

The genetic incorporation of unnatural amino acids into carrier polypeptides and/or target polypeptides using an in vivo orthogonal translation system can produce biologically and/or pharmacologically active carrier polypeptide variants and/or target polypeptide variants, but with the added active/functional groups introduced via the direct incorporation of unnatural amino acids, which functional groups can be reacted to produce stable carrier-target polypeptide conjugates. Furthermore, use of the novel biotechnological tool of in vivo incorporation of unnatural amino acids can help produce the proper native conformation of carrier and/or target polypeptides that comprise unnatural amino acids in high yields at low cost. In addition, the reactivities of the first and second unnatural amino acids that are incorporated into the carrier and target polypeptide variants, respectively, can be deliberately chosen based on such criteria as molecular linker length, reaction conditions, whether the resulting linker is cleavable, etc.

In contrast, total synthesis of carrier or target polypeptide variants with unnatural amino acids using other in vitro methods such as solid-phase peptide synthesis can, in some embodiments, be targeted to shorter molecules (e.g., ~60-100 amino acids) as well as producing denatured proteins at a lower yield.

In certain embodiments, orthogonal translation systems in methylotrophic yeast are used to produce a carrier polypeptide variant, e.g., HSA, that comprises an unnatural amino acid, e.g., p-acetylphenylalanine, that can be reacted with a second unnatural amino acid, e.g., ε-(2-(aminooxy)acetyl)-L-lysine, in a target polypeptide variant, e.g., TSP-1 or ABT-510, to form a stable carrier polypeptide-target polypeptide conjugate. The use of O-RS/O-tRNA pairs in methylotrophic yeast such as *Pichia pastoris* (see below), *P. methanolica, P. angusta* (also known as *Hansenula polymorpha*), *Candida boidinii*, and *Torulopsis* spp. is characterized by several beneficial advantages over other orthogonal systems, e.g., those in *E. coli, S. cerevisiae*, or mammalian cells, for the production of such proteins. As described further hereinbelow, their ease of genetic manipulation, their economy of recombinant protein production, and their abilities to perform the post-translational modifications typically associated with eukaryotic proteins make methylotrophic yeast an advantageous system for the expression of heterologous proteins, e.g., carrier polypeptide variants and/or target polypeptide variants, that comprise unnatural amino acids.

Orthogonal tRNA/Orthogonal Aminoacyl t-RNA Synthetase Technology

In certain embodiments, chemically reactive first and second unnatural amino acids that can participate in chemical ligation reactions, e.g., those described elsewhere herein, are incorporated into carrier polypeptides and/or target polypeptides, respectively, prior to the chemical ligation reaction via orthogonal tRNA (O-tRNA)/aminoacyl-tRNA synthetase (O-RS) systems. Thus, an understanding of the compositions and methods provided by the invention is further developed through an understanding of the activities associated with O-tRNA/O-RS pairs. In general, in order to add unnatural amino acids to the genetic code, new orthogonal pairs comprising an aminoacyl-tRNA synthetase and a suitable tRNA are needed that can function efficiently in the host translational machinery, but that are "orthogonal" to the translation system at issue. Thus, the orthogonal moieties function independently of the synthetases and tRNAs endogenous to the translation system. Desired characteristics of the orthogonal pair include a tRNA that decodes or recognizes only a specific codon, such as a selector codon, e.g., an amber stop codon, that is not decoded by any endogenous tRNA, and an aminoacyl-tRNA synthetase that preferentially aminoacylates, or "charges" its cognate tRNA with only one specific unnatural amino acid. The O-tRNA is also not typically aminoacylated, or is poorly aminoacylated, i.e., charged, by endogenous synthetases.

The general principles of orthogonal translation systems that are suitable for making proteins that comprise one or more unnatural amino acid in the invention are known in the art, as are the general methods for producing orthogonal translation systems. For example, see International Publication Numbers: WO 2002/086075, entitled "METHODS AND COMPOSITION FOR THE PRODUCTION OF ORTHOGONAL tRNA-AMINOACYL-tRNA SYNTHETASE PAIRS"; WO 2002/085923, entitled "IN VIVO INCORPORATION OF UNNATURAL AMINO ACIDS"; WO 2004/094593, entitled "EXPANDING THE EUKARYOTIC GENETIC CODE"; WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE IN VIVO INCORPORATION OF UNNATURAL AMINO ACIDS"; WO 2007/103490, filed Mar. 7, 2007, entitled "SYSTEMS FOR THE EXPRESSION OF ORTHOGONAL TRANSLATION COMPONENTS IN EUBACTERIAL HOST CELLS", and International Patent Application Number PCT/US2008/013568, filed Dec. 10, 2008, entitled, "In Vivo Unnatural Amino Acid Expression in the Methylotrophic Yeast *Pichia Pastoris*". See also, e.g., Liu et al. (2007) "Genetic incorporation of unnatural amino acids into proteins in mammalian cells" *Nat Methods* 4: 239-244; Int'l Application PCT/US2008/081868 entitled "A Genetically Encoded Boronate Amino Acid," filed Oct. 30, 2008; WO2007/047301 entitled "Selective Posttranslational Modification of Phage-Displayed Polypeptides," filed Oct. 11, 2006; and WO2006/110182 entitled "Orthogonal Translation Components for the in vivo Incorporation of Unnatural Amino Acids," filed Oct. 27, 2005. Each of the aforementioned applications is incorporated herein by reference in its entirety. For discussion of orthogonal translation systems that incorporate unnatural amino acids, and methods for their production and use, see also, Wang and Schultz (2005) "Expanding the Genetic Code" *Angewandte Chemie Int Ed* 44: 34-66; Xie and Schultz (2005) "An Expanding Genetic Code" *Methods* 36: 227-238; Xie and Schultz (2005) "Adding Amino Acids to the Genetic Repertoire" *Curr Opinion in Chemical Biology* 9: 548-554; Wang et al. (2006) "Expanding the Genetic Code" *Annu Rev Biophys Biomol Struct* 35: 225-249; Deiters et al. (2005) "In vivo incorporation of an alkyne into proteins in *Escherichia coli*" *Bioorganic & Medicinal Chemistry Letters* 15: 1521-1524; Chin et al. (2002) "Addition of p-Azido-L-phenylalanine to the Genetic Code of *Escherichia coli*" *J Am Chem Soc* 124: 9026-9027; and International Publication No. WO2006/034332, filed on Sep. 20, 2005. The contents of each of these documents are incorporated by reference in its entirety. Additional details of orthogonal translation systems can be found in U.S. Pat. Nos. 7,045,337; 7,083,970; 7,238,510; 7,129,333; 7,262,040; 7,183,082; 7,199,222; and 7,217,809.

As used herein, an unnatural amino acid refers to any amino acid, modified amino acid, or amino acid analogue other than the twenty genetically encoded alpha-amino acids. As used herein, a selenocysteine or a pyrrolysine can be incorporated into a carrier polypeptide and/or target polypeptide. See, e.g., *Biochemistry* by L. Stryer, $3^{rd}$ ed. 1988, Freeman and Company, New York, for structures of the twenty natural amino acids. Unnatural amino acids have side chain groups that distinguish them from the natural amino acids, although unnatural amino acids can be naturally occurring compounds other than the twenty proteinogenic alpha-amino acids. Unnatural amino acids finding use with the invention include an p-(propargyloxy)phenylalanine, p-methoxyphenylalanine, dansylalanine, DMNB-serine, O-methyl-L-tyrosine, an L-3-(2-naphthyl)alanine, an O-4-allyl-L-tyrosine, an O-propargyl-L-tyrosine, an L-Dopa, a fluorinated phenylalanine, an isopropyl-L-phenylalanine, a p-azido-L-phenylalanine, a p-acetyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, sulfo, seleno, ester, thioacid, borate, boronate, phospho, phosphono, heterocyclic, enone, imine, aldehyde, alkoxyamine, hydroxylamine, keto, or amino substituted amino acid, or any combination thereof; an amino acid with a photoactivatable crosslinker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a sugar-substituted cysteine; a redox-active amino acid; an α-hydroxy containing acid; an amino thio acid containing amino acid; an α,α disubstituted amino acid; a β-amino acid; sulfotyrosine, 4-borono-phenylalanine, an aminooxy amino acid, an aminooxy lysine, an aminooxy ornithine, an aminooxy tyrosine, or a cyclic amino acid other than proline.

Other unnatural amino acids that can be incorporated into, e.g., target and/or carrier polypeptides, include, but are not limited to, unnatural amino acids comprising any one or more of the following functional groups: an aldehyde moiety, a keto moiety, a beta-diketo moiety, an alkoxyamine moiety, an acyl hydrazide moiety, a dehydroalanine moiety, a thioester moiety, an ester moiety, a boronate moiety, an azide moiety, an acetylenic moiety, an olefinic moiety, a vicinal thiol amine moiety, and the like. An unnatural amino acid present in a target or carrier polypeptide that comprises such functional groups can react with a second unnatural amino acid, e.g., present in a carrier or target polypeptide, respectively, that comprises a reactive nucleophile and/or electrophile, e.g., a keto moiety, an aldehyde moiety, an alkoxyamine moiety, an acylhydrazide moiety, an azide moiety, an alkyne moiety, an olefinic moiety, an amino moiety, a thiol moiety, an aminophenol moiety, an iodophenyl moiety, or the like.

Orthogonal Translation Systems

Orthogonal translation systems generally comprise cells, e.g., prokaryotic cells such as *E. coli*; and eukaryotic cells such as *S. cerevisiae*, mammalian cells, and methylotrophic yeast cells (e.g., *P. pastoris*, *P. methanolica*, *P. angusta* (also known as *Hansenula* polymorphs), *Candida boidinii*, and *Torulopsis* spp.) etc., that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair can include an O-tRNA, e.g., a suppressor tRNA, a frameshift tRNA, or the like, and a cognate O-RS. Orthogonal systems that can be used to produce the carrier polypeptides and/or target polypeptide variants herein, which typically include O-tRNA/O-RS pairs, can comprise a cell or a cell-free environment.

In general, when an orthogonal pair recognizes a selector codon and loads an amino acid in response to the selector codon, the orthogonal pair is said to "suppress" the selector codon. That is, a selector codon that is not recognized by the translation system's endogenous machinery is not ordinarily charged, which results in blocking production of a polypeptide that would otherwise be translated from the nucleic acid. In an orthogonal pair system, the O-RS aminoacylates the O-tRNA with a specific unnatural amino acid, e.g., p-acetylphenylalanine, as used in the Example herein. The charged O-tRNA recognizes the selector codon and suppresses the translational block caused by the selector codon, e.g., producing an HSA variant that comprises a p-acetylphenylalanine, e.g., at amino acid position 37.

The translation system uses the O-tRNA/O-RS pair to incorporate an unnatural amino acid into a growing polypeptide chain, e.g., via a polynucleotide that encodes a polypeptide of interest (such as a carrier polypeptide and/or a target polypeptide), where the polynucleotide comprises a selector codon that is recognized by the O-tRNA. In certain systems, the cell can include one or more additional O-tRNA/O-RS pairs, where an additional O-tRNA is loaded by an additional O-RS with a different unnatural amino acid. For example, one of the O-tRNAs can recognize a four base codon and the other O-tRNA can recognize a stop codon. Alternately, multiple different stop codons, multiple different four base codons, multiple different rare codons and/or multiple different noncoding codons can be used in the same coding nucleic acid. Thus, a single polypeptide, e.g., carrier polypeptide and/or target polypeptide variant, can comprise multiple unnatural amino acids. Alternatively or additionally, different carrier and/or target polypeptide or polypeptide variants created in the system can comprise different unnatural amino acids. For further details regarding available O-RS/O-tRNA cognate pairs and their use, see, e.g., the references noted elsewhere herein.

Thus, some translational systems can comprise multiple O-tRNA/O-RS pairs, which allow incorporation of more than one unnatural amino acid into a carrier polypeptide variant and/or a target polypeptide variant. For example, the translation system can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair, where the O-tRNA recognizes, e.g., an amber selector codon, can further comprise a second orthogonal pair, where the second O-tRNA recognizes a different selector codon, e.g., an opal codon, an ochre codon, a four-base codon, a rare codon, a non-coding codon, or the like. In some systems, the different orthogonal pairs are derived from different sources, which can facilitate recognition of different selector codons.

Certain translation systems can comprise a cell, such as an *E. coli* cell, a mammalian cell, an *S. cerevisiae* cell, or a methylotrophic yeast cell (e.g., a *P. pastoris* cell, a *P. methanolica* cell, a *P. angusta* (or *Hansenula polymorpha*) cell, a *Candida boidinii* cell, or a *Torulopsis* spp. cell) that includes an orthogonal tRNA (O-tRNA), an orthogonal aminoacyl-tRNA synthetase (O-RS), an unnatural amino acid, and a nucleic acid that comprises a polynucleotide that encodes a polypeptide of interest, e.g., a carrier polypeptide variant and/or a target polypeptide variant, where the polynucleotide comprises the selector codon that is recognized by the O-tRNA. Although orthogonal translation systems can utilize cultured cells to produce proteins having unnatural amino acids, it is not intended that orthogonal translation systems used herein require an intact, viable cell. For example, an orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a tRNA/synthetase pair that is heterologous to the system in which the pair will function from a source, or multiple sources, other than the translation system in which the tRNA/synthetase pair will be used. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O-RS. Such strategies can also be combined.

Orthogonal tRNA (O-tRNA)

An orthogonal tRNA (O-tRNA) desirably mediates incorporation of an unnatural amino acid into a polypeptide encoded by a polynucleotide that comprises a selector codon recognized by the O-tRNA, e.g., in vivo or in vitro.

Thus compositions comprising an O-tRNA can further include an orthogonal aminoacyl-tRNA synthetase (O-RS), where the O-RS preferentially aminoacylates the O-tRNA with an unnatural amino acid. Such compositions including an O-tRNA can further include a translation system, e.g., in vitro or in vivo. A nucleic acid that comprises a polynucleotide that encodes a polypeptide of interest, where the polynucleotide comprises a selector codon that is recognized by the O-tRNA, or a combination of one or more of these can also be present in the cell.

Methods for producing a recombinant orthogonal tRNA and screening its efficiency with respect to incorporating an unnatural amino acid into a polypeptide in response to a selector codon can be found in, e.g., International Application Publications WO 2002/086075, entitled "METHODS AND COMPOSITIONS FOR THE PRODUCTION OF ORTHOGONAL tRNA AMINOACYL-tRNA SYNTHETASE PAIRS"; WO 2004/094593, entitled "EXPANDING THE EUKARYOTIC GENETIC CODE"; and WO 2005/019415, filed Jul. 7, 2004. See also Forster et al. (2003) "Programming peptidomimetic synthetases by translating genetic codes designed de novo." *Proc Natl Acad Sci USA* 100: 6353-6357; and Feng et al. (2003) "Expanding tRNA recognition of a tRNA synthetase by a single amino acid change." *Proc Natl Acad Sci USA* 100:5676-5681. Additional details can be found in U.S. Pat. Nos. 7,045,337; 7,083,970; 7,238,510; 7,129,333; 7,262,040; 7,183,082; 7,199,222; and 7,217,809.

Orthogonal Aminoacyl-tRNA Synthetase (O-RS)

The O-RS of systems used to produce, e.g., carrier and/or target polypeptide variants that comprise unnatural amino acids, preferentially aminoacylates an O-tRNA with an unnatural amino acid either in vitro or in vivo. The O-RS can be provided to the translation system by a polypeptide that includes an O-RS and/or by a polynucleotide that encodes an O-RS or a portion thereof.

General details for producing an O-RS, assaying its aminoacylation efficiency, and/or altering its substrate specificity can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS"; and WO 2004/094593, entitled "EXPANDING THE EUKARYOTIC GENETIC CODE." See also, Wang and Schultz (2005) "Expanding the Genetic Code." *Angewandte Chemie Int Ed* 44: 34-66; and Hoben and Soll (1985) *Methods Enzymol* 113: 55-59, the contents of which are incorporated by reference in their entirety. Additional details concerning such systems can be found in U.S. Pat. Nos. 7,045,337; 7,083,970; 7,238,510; 7,129,333; 7,262,040; 7,183,082; 7,199,222; and 7,217,809

Source and Host Organisms

The orthogonal translational components (O-tRNA and O-RS) that can optionally be used to create, e.g., the carrier polypeptide variants and target polypeptide variants comprising unnatural amino acids that react to form the stable carrier-target conjugates of the invention, can be derived from any organism, or a combination of organisms, for use in a host translation system from any other species, with the caveat that the O-tRNA/O-RS components and the host system work in an orthogonal manner. It is not a requirement that the O-tRNA and the O-RS from an orthogonal pair be derived from the same organism. For example, the orthogonal components can be derived from archaebacterial genes for use in a eubacterial host system.

Furthermore, the orthogonal O-tRNA can be derived from an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a *eubacterium*, such as *Escherichia coli, Thermus thermophilus, Bacillus subtilis, Bacillus stearothermphilus*, or the like, while the orthogonal O-RS can be derived from an organism or combination of organisms, e.g., an archaebacterium, such as *Methanococcus jannaschii, Methanobacterium thermoau-* *totrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a *eubacterium*, such as *Escherichia coli, Thermus thermophilus, Bacillus subtilis, Bacillus stearothermphilus*, or the like. In other systems, eukaryotic sources, e.g., plants, algae, protists, fungi, yeasts, animals, e.g., mammals, insects, arthropods, or the like can also be used as sources of O-tRNAs and O-RSs. Furthermore, the individual components of an O-tRNA/O-RS pair can be derived from the same organism or different organisms.

The O-tRNA, O-RS or O-tRNA/O-RS pair can be selected or screened in vivo or in vitro and/or used in a cell, e.g., a eubacterial cell, to produce a polypeptide with an unnatural amino acid. The eubacterial cell used is not limited and can include, for example, *Escherichia coli, Thermus thermophilus, Bacillus subtilis, Bacillus stearothermphilus*, or the like.

Selector Codons

Various selector codons expand the genetic codon framework of protein biosynthetic machinery. For example, a selector codon can include, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. Conventional site-directed mutagenesis can be used to introduce the selector codon at the site of interest in a polynucleotide encoding a polypeptide of interest (e.g., a self antigen of a subject, etc.). See, e.g., Sayers et al. (1988) "5', 3' Exonuclease in phosphorothioate-based oligonucleotide-directed mutagenesis." *Nucl Acid Res* 16: 791-802. By using different selector codons, multiple orthogonal tRNA/synthetase pairs can be used that allow the simultaneous site-specific incorporation of multiple unnatural amino acids e.g., including at least one unnatural amino acid, using these different selector codons.

Unnatural amino acids can also be encoded with rare codons. For example, when the arginine concentration in an in vitro protein synthesis reaction is reduced, the rare arginine codon AGG has proven to be efficient for insertion of Ala by a synthetic tRNA acylated with alanine. See, e.g., Ma et al. (1993) "In vitro protein engineering using synthetic tRNA$^{Ala}$ with different anticodons." *Biochemistry* 32: 7939-7945. In such case, the synthetic tRNA competes with the naturally occurring tRNA$^{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver (1997) "Exploiting unassigned codons in *Micrococcus luteus* for tRNA-based amino acid mutagenesis" *Nucl Acid Res* 25: 4685-4689.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Particular methods of incorporating unnatural amino acids into proteins, e.g., carrier polypeptides and/or target polypeptides described elsewhere herein, can include using extended codons based on frameshift suppression. Four or more base codons can insert, e.g., one or multiple unnatural amino acids, into the same protein.

In other instances, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al. (2002) "Exploring the Limits of Codon and Anticodon Size." *Chemistry and Biology* 9: 237-244; Magliery et al. (2001) "Expanding the Genetic Code: Selection of Efficient Suppressors of Four-base Codons and Identification of "Shifty" Four-base Codons with a Library Approach in *Escherichia coli.*" *J Mol Biol* 307: 755-769; Ma et al. (1993) "In vitro protein engineering using synthetic tRNA$^{Ala}$ with different anticodons." *Biochemistry* 32: 7939; Hohsaka et al. (1999) "Efficient Incorporation of Nonnatural Amino Acids with Large Aromatic Groups into Streptavidin in in Vitro Protein Synthesizing Systems." *J Am Chem Soc* 121: 34-40; and Moore et al. (2000) "Quadruplet Codons: Implications for Code Expansion and the Specification of Translation Step Size." *J Mol Biol* 298: 195-209. Four base codons have been used as selector codons in a variety of orthogonal systems. See, e.g., WO 2005/019415; WO 2005/007870; and WO 2005/07624. See also, Wang and Schultz, (2005) "Expanding the Genetic Code," *Angewandte Chemie Int Ed* 44: 34-66.

For a given system, a selector codon can also include one of the natural three base codons, where the endogenous system does not use (or rarely uses) the natural base codon. For example, such can include a system that is lacking a tRNA that recognizes the natural three base codon, and/or a system where the three base codon is a rare codon.

Selector codons optionally include unnatural base pairs. Descriptions of unnatural base pairs which can be adapted for use with the methods and compositions herein include, e.g., Hirao et al. (2002) "An unnatural base pair for incorporating amino acid analogues into protein." *Nature Biotechnology* 20: 177-182. See also, Wu et al. (2002) "Enzymatic Phosphorylation of Unnatural Nucleosides." *J Am Chem Soc* 124: 14626-14630.

Expression and Purification of Carrier Polypeptides and/or Target Polypeptides Comprising Unnatural Amino Acids Using Orthogonal Translation Systems in Methylotrophic Yeast In embodiments described in the Example, the carrier polypeptide HSA comprising a first unnatural amino acid, p-acetylphenylalanine is produced, e.g., in preparation for conjugation to a target polypeptide comprising a second unnatural amino acid, using an orthogonal translation system in the methylotrophic yeast *Pichia Pastoris*. The orthogonal components used in *P. pastoris* include an O-RS derived from *E. coli* tyrosyl tRNA-synthetase, and an O-tRNA, e.g., a mutant tyrosyl tRNA$_{CUA}$ amber suppressor derived from *E. coli*, which function as an orthogonal pair in host *P. pastoris* cells.

The use of O-RS/O-tRNA pairs in methylotrophic yeast is characterized by several beneficial advantages over other orthogonal systems, e.g., *E. coli*, *S. cerevisiae*, or mammalian cells, for the production of carrier polypeptides and/or target polypeptides that comprise unnatural amino acids. First, the eukaryotic subcellular structure of methylotrophic yeast such as *P. pastoris, P. methanolica, P. angusta* (*Hansenula polymorpha*), *Candida boidinii*, and *Torulopsis* spp., permits the incorporation of UAA into proteins that require complex post-translational modifications, e.g., glycosylation, disulfide bond formation, sulfation, acetylation, prenylation, and proteolytic processing, for biological activity, e.g., mammalian proteins such as human serum albumin (HSA) and human neutral endopeptidase (NEP). Thus, many proteins that end up as inactive inclusion bodies in bacterial systems can be produced as biologically active molecules in methylotrophic yeast. Second, proteins comprising UAA that are expressed in and prepared from in methylotrophs do not contain high concentrations of pyrogens, e.g., lipopolysaccharides, or antigens, e.g., high-mannose oligosaccharides, that might hinder the efficacy of proteins expressly designed for therapeutic use. Third, many well established techniques and methods, e.g., gene-targeting, high-frequency DNA transformation, cloning by functional complementation, are available for the genetic manipulation of foreign genes in methylotrophs (Lin-Cereghino et al, (2002) "Production of recombinant proteins in fermenter cultures of the yeast *Pichia pastoris*." *Curr Opin Biotechnol* 13: 329-332). The availability of endogenous inducible promoters and selectable markers adds flexibility to range of proteins comprising UAA that can be produced by in methylotrophic yeast hosts.

In addition to these advantages, methylotrophs such as *P. pastoris, P. methanolica, P. angusta* (or *Hansenula polymorpha*), *Candida boidinii*, and *Torulopsis* spp., are also well suited for low-cost, large-scale synthesis of complex proteins comprising UAA. Methylotrophic yeast are easily cultured in a simple, defined salt medium, eliminating the need for the expensive media supplements and costly equipment that are required for, e.g., baculovirus expression systems or mammalian tissue culture. In general, methylotrophs can grow to very high cell densities, and, under ideal conditions, methylotrophic yeast can multiply to the point where the cell suspension is the consistency of a paste. Their prolific growth rates allow recombinant methylotrophic yeast strains to produce carrier and/or target polypeptides comprising UAA at high levels, e.g., 10- to 100-fold higher level than in *S. cerevisiae*. Their ease of genetic manipulation, their economy of recombinant protein production, and their abilities to perform the posttranslational modifications typically associated with eukaryotic proteins make methylotrophic yeast an advantageous system for the expression of heterologous proteins comprising UAA.

The four known genera of methylotrophic yeast, e.g., *Hansenula, Pichia, Candida*, and *Torulopsis*, share a common metabolic pathway that enables them to use methanol as a sole carbon source. In a transcriptionally regulated response to methanol induction, several of the enzymes are rapidly synthesized at high levels. Since the promoters controlling the expression of these genes are among the strongest and most strictly regulated yeast promoters, methylotrophic yeast have become very attractive as hosts for the large scale production of recombinant proteins. The cells of these methylotrophic yeast can be grown rapidly to high densities, and the level of product expression can be regulated by simple manipulation of the medium. Expression systems have this far been developed in *P. pastoris, P. methanolica, P. angusta* (or *Hansenula polymorpha*) and *Candida boidinii*, and these systems are further elaborated in, e.g., Houard et al. (2002) "Engineering of non-conventional yeasts for efficient synthesis of macromolecules: the methylotrophic genera." *Biochimie* 84: 1089-1093; Gellison (2002) *Hansenula Polymorpha: Biology and Applications,* 1st Ed., Wiley-VCH, NY; U.S. Pat. No. 6,645,739; Gellisen (2000) "Heterologous protein production in methylotrophic yeasts." *Applied Microbiology and Biotechnology* 54: 741-750. Many of these systems are commercially available, e.g., *Hansenula* kits from Artes Biotecnology and *Pichia* kits from Invitrogen, for use in academic and industrial laboratories.

Carrier polypeptide variants and/or target polypeptide variants comprising one (or more) unnatural amino acid can be expressed and purified from methylotrophic yeast. As described elsewhere herein, foreign genes can be expressed in

*P. pastoris* from the alcohol oxidase 1 (AOX1) promoter, the regulatory characteristics of which are well suited for this purpose. The AOX1 promoter is tightly repressed during growth of the yeast on most carbon sources, e.g., glycerol, glucose, or ethanol, but is highly induced during growth on methanol (Tschorp et al. (1987) "Expression of the lacZ gene from two methanol-regulated promoters in *Pichia pastoris*." *Nucl Acids Res* 15: 3859-3876). Expression of, e.g., carrier polypeptide variants and/or target polypeptide variants, encoded by genes regulated by $P_{AOX1}$ can typically reach ≥30% of the total soluble protein in *P. pastoris* cells grown on methanol. For the production of recombinant carrier and/or target polypeptide variants, $P_{AOX1}$-controlled expression strains are grown initially on a repressing carbon source to generate biomass, e.g., maximize culture density, and then shifted to a methanol-containing medium, e.g., BMGY, BMMY, or BMM, as the sole energy source to induce expression of the foreign gene.

However, promoters that are not induced by methanol can also be advantageous for the expression of heterologous genes encoding carrier polypeptides or polypeptide variants and/or target polypeptides or polypeptide variants. Alternative promoters to the AOX1 promoter in this expression system are the *P. pastoris* GAP, FLD1, AOX2, ILC1, and YPT1 promoters. Further details regarding the regulation of these promoters, the conditions under which it can be most beneficial to express a foreign gene from these promoters, and the expression of foreign proteins in *P. pastoris* by these promoters are discussed in, e.g., Sears et al. (1998) "A Versatile Set of Vectors for Constitutive and Regulated Gene Expression in *Pichia pastoris*." *Yeast* 14: 783-790; Vassileva et al. (2001) "Expression of hepatitis B surface antigen in the methylotrophic yeast *Pichia pastoris* using the GAP promoter." *J Biotechnology* 88: 21-35; Shen et al. (1998) "A strong nitrogen-source regulated promoter for controlled expression of foreign genes in the yeast *Pichia pastoris*." *Gene* 216: 93-102; Lin-Cereghino et al. "Expression of foreign genes in the yeast *Pichia pastoris*." *Genetic Engineering Principles and Methods*, Vol. 23 1$^{st}$ Ed. Ed. Jane K. Setlow, Springer, NY: (2005).

Although expression of carrier and/or target polypeptide variants in *P. pastoris* or other methylotrophic yeast can be done in shake-flask culture, protein levels expressed in this system are typically much higher in fermenter cultures, because it is in fermenters that parameters such as pH, aeration, and carbon source feed rate can be controlled to achieve ultra-high cell densities, e.g., >100 g/L dry cell weight; >400 g/L wet cell weight, >500 $OD_{600}$ units/ml (see, e.g., Lin-Cereghino et al. (2002) "Production of recombinant proteins in fermenter cultures of the yeast *Pichia pastoris*." *Curr Opin Biotechnol* 13: 329-332. A hallmark of the *P. pastoris* expression system is the ease with which expression strains scale up from shake-flask to high-density fermenter cultures.

A three step process can typically be employed to express carrier and/or target polypeptide variants encoded by genes under the transcriptional control of $P_{AOX1}$, in fermenter cultures of *P. pastoris* or other methylotrophic yeast. In the first step, the engineered methylotrophic yeast expression strain is cultured in a simple, defined, medium comprising a non-fermentable, $P_{AOX1}$-repressing carbon source to permit the cell growth. The second step comprises a transition phase during which glycerol is fed to the culture at a growth-limiting rate to further increase the culture's biomass and to prepare the cells for induction. During the third step, methanol is added to the culture at a rate that allows the cells to physiologically acclimate to metabolizing methanol and to synthesize the recombinant protein. The methanol feed rate is then adjusted upwards periodically until the desired growth rate and protein expression rate is achieved (Lin-Cereghino et al. "Expression of foreign genes in the yeast *Pichia pastoris*." *Genetic Engineering Principles and Methods*, Vol. 23 1$^{st}$ Ed. Ed. Jane K. Setlow, Springer, NY: (2005)).

The media in which methylotrophic yeast can be grown are inexpensive and highly defined, consisting of carbon sources, e.g., glycerol and/or methanol, biotin, salts, trace elements, and water. The media are free of pyrogens and toxins, and are therefore compatible with the production of pharmaceutical agents for human use.

The recombinant carrier polypeptide variants and/or target polypeptide variants expressed in methylotrophic yeast can be produced either intracellularly or extracellularly. Because methylotrophic yeast secrete only low levels of endogenous protein, secreted recombinant protein can constitute the majority of protein in the medium. Therefore, directing the recombinant carrier and/or target polypeptide variant into the culture medium can serve as a first step in protein purification, eliminating the need to follow harsh yeast lysis protocols and avoiding the possibility of contamination of the recombinant protein by endogenous yeast proteins. However, due to protein stability and folding requirements, secreting a heterologous protein into the medium is typically reserved only for those proteins that are normally secreted by their native host cells. Nevertheless, kits are available, e.g., Original *Pichia* Expression Kit (Invitrogen), Multi-Copy *Pichia* Expression Kit (Invitrogen), *Pichia* Protein Expression System (Research Corporation Technologies), in which pre-made expression cassettes allow practitioners to clone a gene of interest in frame with sequences encoding its native secretion signal, the *S. cerevisiae* α-factor prepro peptide, or the *P. pastoris* acid phosphatase (PHO1) signal to allow secretion into the culture medium. A number of techniques for the recovery of intracellular recombinant proteins from methylotrophic have also been developed (Shepard et al. (2002) "Recovery of intracellular recombinant proteins from the yeast *Pichia pastoris* by cell permeabilization." *J Biotechnology* 99: 149-160; U.S. Pat. No. 6,821,752).

General Methods for the Purification of Heterologous Proteins from Methylotrophic Yeast A variety of protein purification methods are well known in the art and can be applied to the purification and analysis of carrier and/or target polypeptides and polypeptide variants comprising UAA expressed in methylotrophic yeast. These techniques, and others that are necessary for the analysis of polypeptides, include those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods,* 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Methods and Strategies for Strain Construction in Methylotrophic Yeast

Shuttle vectors that are suitable for replication in *E. coli* are typically used to engineer nucleic acid constructs that place a gene of interest, e.g., a gene encoding a carrier polypeptide and/or a target polypeptide or variant thereof comprising a selector codon, under the control of a highly inducible methylotrophic yeast promoter. Because plasmids are relatively unstable in methylotrophic yeast, the expression constructs are then usually linearized and transformed into e.g., a *Pichia* cell, a *Hansenula* cell, a *Candida* cell, or a *Torulopsis* cell, and integrated into the genome. Integration is generally site specific; however, high frequencies of non-homologous integration have been observed in *Hansenula polymorpha* (Agaphonov et al. (2005) "Defect of vacuolar protein sorting stimulates proteolytic processing of human urokinase-type plasminogen activator in the yeast *Hansenula polymorpha*." *FEMS Yeast Research* 5: 1029-1035). Additional details regarding the general molecular manipulation, e.g., transformation, gene targeting, cloning by functional complementation, use of available selectable markers, and the like, of methylotrophic yeast can be found in, e.g.; Peberdy, Ed. (1991) *Applied Molecular Genetics of Fungi*. Cambridge University Press, UK; *Hansenula Polymorpha: Biology and Applications*, 1st Ed., Wiley-VCH; Higgins and Cregg. *Pichia Protocols (Methods in Molecular Biology)*, $1^{st}$ Ed. Humana Press: New Jersey (1998); and the references cited therein.

In a preferred embodiment, carrier polypeptide variants and/or target polypeptide variants, e.g., those described in detail elsewhere herein, are expressed in the methylotroph *P. pastoris*. Expression of most foreign genes in *P. pastoris* can be performed by following three basic steps: The insertion of the gene encoding the carrier or target polypeptide into an expression vector; the introduction of the expression vector into the *P. pastoris* genome; and analysis of the putative expression strain for production of the carrier or target polypeptide variant expressed by the foreign gene, the methods for which are described above. Fortunately, techniques for the molecular genetic manipulation of *P. pastoris*, e.g., DNA-mediated transformation, gene targeting, gene replacement, and cloning by functional complementation, are similar to those described for *S. cerevisiae*. In contrast to *S. cerevisiae*, however, plasmids are unstable in *P. pastoris*, and expression constructs encoding a protein of interest are instead integrated into the *P. pastoris* genome via homologous recombination. Protocols for the molecular genetic manipulation of *P. pastoris* are discussed in detail in, e.g., Cregg et al. (1985) "*Pichia pastoris* as a host system for transformations." *Molec Cell Biol* 5: 3376-3385; Lin-Cereghino et al. "Expression of foreign genes in the yeast *Pichia pastoris*." *Genetic Engineering Principles and Methods*, Vol. 23 $1^{st}$ Ed. Ed. Jane K. Setlow, Springer, NY: (2005); Higgins and Cregg. *Pichia Protocols (Methods in Molecular Biology)*, $1^{st}$ Ed. Humana Press: New Jersey (1998); Lin-Cereghino et al. (2000) "Heterologous protein expression in the methylotrophic yeast *Pichia pastoris*." *FEMS Microbiol Rev* 24: 45-66, and in the references cited therein.

A variety of *P. pastoris* host strains and expression vectors are available. Virtually all *P. pastoris* expression strains are derived from NRRL-Y 111430 (Northern Regional Research Laboratories, Peoria, Ill.). Most expression strains have one or more auxotrophic markers that permit selection of expression vectors comprising the appropriate complementary markers. Host strains can differ in their abilities to metabolize methanol because of deletions in AOX1, AOX2, or both. In fact, strains carrying mutations in AOX1 and/or AOX2 can be better producers of foreign proteins than wild-type strains (Cregg et al. (1987) "High level expression and efficient assembly of hepatitis B antigen in the methylotrophic yeast, *Pichia pastoris*." *Bio/Technology* 5: 479-485; Chiruvolu et al. (1997) "Recombinant protein production in an alcohol oxidase-defective strain of *Pichia pastoris* in fed-batch fermentation." *Enzyme Microb Technol* 21: 277-283). Nevertheless, even aox1⁻ strains retain the ability to induce expression of foreign proteins at high levels from the AOX1 promoter. More detailed information host strains, including protease deficient host strains in which the expression of certain recombinant proteins may be more beneficial, is available in, e.g., Brierley et al. (1998) "Secretion of recombinant insulin-like growth factor-1 (IGF-1)." *Methods Mol Biol* 103: 149-177; White et al. (1995) "Large-scale expression, purification, and characterization of small fragments of thrombomodulin: the roles of the sixth domain and of methionine 388." *Protein Eng* 8: 1177-1187.

Most *P. pastoris* expression vectors have been designed as *E. coli/P. pastoris* shuttle vectors, containing origins of replication for maintenance in *E. coli* and selectable markers that are functional in one or both organisms, e.g., ARG4, HIS4, ADE1, URA3, TRP1 and certain antibiotics, e.g., Zeocin™ and Geneticin®, which are selectable in *P. pastoris*, and/or any of a number of antibiotic resistance markers which are selectable in *E. coli*. Typically, an expression vector will comprise 5' AOX1 promoter sequences and AOX1-derived sequences for transcriptional termination, between which lies a multiple cloning site. Although the AOX1 promoter has been successfully used to express numerous foreign proteins, there are circumstances under which the use of this promoter may not be suitable, e.g., for the production of food products. Alternative promoters to the AOX1 promoter in this expression system are the *P. pastoris* AOX2, ICL1, GAP, FLD1, and YPT1 promoters. Generalized diagrams of expression vectors comprising any of the aforementioned promoters and lists of possible vector components are also given in, e.g., Lin-Cereghino et al. "Expression of foreign genes in the yeast *Pichia pastoris*." *Genetic Engineering Principles and Methods*, Vol. 23 $1^{st}$ Ed. Ed. Jane K. Setlow, Springer, NY: (2005) and Lin-Cereghino, et al. (2000) "Heterologous protein expression in the methylotrophic yeast *Pichia pastoris*." *FEMS Microbiol Rev* 24: 45-66. In addition, the DNA sequences of many vectors can be found at the Invitrogen website (www.invitrogen.com), and are available from Invitrogen individually and in *P. pastoris* expression kits.

General Molecular Cloning Methods and Techniques

Procedures for isolating, cloning, and amplifying nucleic acids in preparation for, e.g., cloning a gene of interest, e.g., a gene encoding a carrier polypeptide variant or a target polypeptide variant, into an expression construct as described above, are replete in the literature and can be used in the present invention to, e.g., provide and express a gene of interest in a methylotrophic yeast, e.g., *P. pastoris*. Further details these techniques can be found in Berger and Kimmel, *Guide to Molecular Cloning Techniques, Methods in Enzymology* volume 152 Academic Press, Inc., San Diego, Calif. (Berger); Sambrook et al. *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc (Rapley); *Current Protocols in Molecular Biology*, F. M. Ausubel et al. eds., Current Protocols, a joint venture between Greene Publishing Associates, Inc. and John Wiley & Sons, Inc., (supplemented through 2007) ("Ausubel")); *PCR Protocols A Guide to Methods and Applications* (Innis et al. eds) Academic Press Inc. San Diego, Calif. (1990) (Innis); Chen et al. (ed) *PCR Cloning Protocols, Second Edition* (Methods in Molecular Biology, volume 192) Humana Press; in Viljoen et al. (2005) *Molecular Diagnostic PCR Handbook* Springer; and Demidov and Broude (eds) (2005) *DNA Amplification: Current Technologies and Applications*, Horizon Bioscience, Wymondham, UK. Other useful references, e.g., for cell isolation and culture, e.g., for subsequent nucleic acid isolation, include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A plethora of kits are also commercially available for the purification of plasmids or other relevant nucleic acids from cells, (see, e.g., EasyPrep™, FlexiPrep™ both from Pharmacia Biotech; StrataClean™, from Stratagene; QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Sambrook, Ausubel and Berger. In addition, essentially any nucleic acid can be custom or standard ordered from any of a variety of commercial sources, such as Operon Technologies Inc. (Huntsville, Ala.).

It will be appreciated that while particular methods of constructing carrier and/or target polypeptide variants that comprise chemically reactive unnatural amino acids are detailed herein, e.g., using orthogonal translation systems in methylotrophic yeast, they should not necessarily be taken as limiting. Carrier polypeptide variants comprising a first reactive amino acid and/or target polypeptide variants comprising a second reactive amino acid can be constructed using orthogonal translation systems in, e.g., *E. coli, S. cerevisiae*, mammalian cells, etc. Furthermore, other, e.g., non-orthogonal, methods of constructing carrier and/or target polypeptides having unnatural amino acids are also included herein in the many embodiments. Such methods are described in further detail below.

Non-Orthogonal Methods for the Direct Incorporation of Unnatural Amino Acids into Carrier Polypeptides and/or Target Polypeptides As stated above, in different embodiments of the invention, carrier polypeptides and target polypeptides or carrier polypeptides and target polypeptides variants (that each comprise an reactive unnatural amino acid which, when reacted with the unnatural amino acid in the other, forms a stable carrier polypeptide-target polypeptide conjugate) can be constructed via direct incorporation methods such as an orthogonal translation system. This represents a preferred embodiment, due to the ability of orthogonal systems to produce high yields of correctly folded and post-translationally modified polypeptides with site-specifically incorporated unnatural amino acids. Alternatively or additionally, however, other strategies for the direct incorporation of unnatural amino acids into a polypeptide chain can be employed to introduce first and second unnatural amino acids into the carrier polypeptide variants and/or target polypeptide variants, respectively. It will be appreciated that in typical embodiments herein, an unnatural amino acid is incorporated into a carrier and/or target polypeptide during construction of the polypeptide and is not added via post-translational chemical derivatization.

For example, one general in vitro biosynthetic method for incorporating unnatural amino acids into, e.g., carrier and/or target polypeptides, during primary construction uses nonsense or frameshift suppressor tRNAs that have been chemically acylated with the desired unnatural amino acid and then added to an in extract capable of supporting protein biosynthesis and which includes a gene containing a desired amber nonsense mutation. This strategy has been used to site-specifically incorporate over 100 unnatural amino acids into a variety of proteins of virtually any size and can be used herein to create carrier and/or target polypeptide variants that comprise unnatural amino acids. See, e.g., Cornish et al. (1995) "Probing Protein Structure and Function with an Expanded Genetic Code." *Angew Chem Int Ed Engl* 34: 621-633; Noren et al. (1989) "A general method for site-specific incorporation of unnatural amino acids into proteins." *Science* 244: 182-188; and Bain et al. (1989) "Biosynthetic site-specific incorporation of a non-natural amino acid into a polypeptide." *JACS* 111: 8013-8014.

In other embodiments, unnatural amino acids can be directly incorporated into smaller carrier and/or target polypeptides (ranging from 60-100 amino acids) via chemical synthesis. Solid phase peptide synthesis is a method that is widely used to chemically synthesize peptides and small proteins that comprise unnatural amino acids (see, e.g., Merrifield (1963) "Solid Phase Peptide synthesis. I. The synthesis of a tetrapeptide." *JACS* 85: 2149-2154) and can be adapted to produce carrier and/or target polypeptides comprising unnatural amino acids that can be reacted to produce a stable conjugate. This technique typically comprises two stages: The first stage solid phase peptide synthesis (SPPS) includes the assembly of a peptide chain using protected amino acid derivatives on a polymeric support via repeated cycles of coupling-deprotection. The free N-terminal amine of a solid-phase attached peptide can then be coupled to a single N-protected amino acid unit, e.g., an unnatural amino acid. This unit is then deprotected, revealing a new N-terminal amine to which a further amino acid may be attached. While the peptide is being synthesized usually by stepwise methods, all soluble reagents can be removed from the peptide-solid support matrix by filtration and washed away at the end of each coupling step. In the second stage of SPPS, the peptide is cleaved from the support and side-chain protecting groups are removed to produce the peptide, e.g., a carrier or target polypeptide comprising one or more unnatural amino acids. There are two major used forms of solid phase peptide synthesis: Fmoc (Carpino et al. (1972) "9-Fluorenylmethoxycarbonyl amino-protecting group." *J Org Chem* 37: 3404-3409), in which a base labile alpha-amino protecting group is used, and t-Boc, in which an acid labile protecting group is used. Each method involves different resins and amino acid side-chain protection and consequent cleavage/deprotection steps. For additional details regarding peptide synthesis, see the following publications and references cited within: Crick et al. (1961) "General nature of the genetic code for proteins." *Nature* 192: 1227-1232; Hofmann et al. (1966) "Studies on Polypeptides. XXXVI. The Effect of Pyrazole—Imidazole Replacements on the S-Protein Activating Potency of an S-Peptide Fragment[1-3]." *JACS* 88: 5914-5919; Kaiser et al. (1989) "Synthetic approaches to biologically active peptides and proteins including enzymes." *Acc Chem Res* 22: 47-54; Nakatsuka et al. (1987) "Peptide segment synthesis catalyzed by the semisynthetic enzyme thiolsubtilisin." *JACS* 109:

3808-3810; Schnolzer et al. (1992) "Constructing proteins by dovetailing unprotected synthetic peptides: backbone-engineered HIV protease." *Science* 5054: 221-225; Chaiken et al. (1981) "Semisynthetic peptides and proteins." *CRC Crit. Rev Biochem* 11: 255-301; Offord (1987) "Protein engineering by chemical means?" *Protein Eng* 1: 151-157; and Jackson et al. "A designed peptide ligase for total synthesis of ribonuclease A with unnatural catalytic residues." *Science* 5184: 243-247.

Chemical Coupling Reactions that can be Used to Conjugate Carrier Polypeptide and Target Polypeptide Variants Current methods for chemically coupling target polypeptide variants (e.g., small therapeutic peptide variants) to carrier polypeptide variants range from the use of non-specific reagents, e.g., glutaraldehyde or carbodiimide activated N-hydroxysuccinimide esters, to highly specific heterobifunctional crosslinkers that can circumvent the formation of carrier polypeptide-carrier polypeptide or target-polypeptide-target polypeptide conjugates. However, only a limited number of amino acids can be chemically modified with such reagents (e.g., amino acids comprising amine, keto, thiol, sulfhydryl, or carboxyl groups). Using these reagents in the coupling of a carrier polypeptide to a target polypeptide can perturb the conformation of the carrier polypeptide, the target polypeptide, or the resulting carrier-target polypeptide conjugate, thus decreasing the conjugate's stability, biological activity, pharmacokinetic activity, etc. Using such reagents can often result in the production of a heterogeneous population of carrier-polypeptide-target polypeptide complexes, which can be difficult to separate, decreasing manufacturing efficiency and complicating quality control.

In contrast, conjugates of the invention are produced by reacting a first unnatural amino acid that has been incorporated into a carrier polypeptide variant, e.g., using an orthogonal translation system in a methylotrophic yeast cell, with a second unnatural amino acid that has been incorporated into a target polypeptide variant in an orthogonal coupling reaction, e.g., any one of the chemical ligation reactions described below. These reactions can be performed in vitro or in vivo, depending on the appropriate reaction conditions. Because only the unnatural amino acids present on the carrier and target polypeptide variants participate in the ligation reaction, the methods of the invention can be reliably used to produce homogenous populations of well-defined carrier-polypeptide-target polypeptide conjugates (e.g., comprising defined stoichiometries and defined ligation sites) with high efficiency. Because any of a variety chemically of reactive first and second unnatural amino acids can optionally be incorporated into carrier and target polypeptide variants, respectively, the production of carrier-target polypeptide conjugates is not limited only to those conditions under which a particular chemical ligation reaction can proceed, e.g., conditions under which the target polypeptide variant, the carrier polypeptide variant, or the resulting carrier-target conjugate may be unstable. Furthermore, existing technologies beneficially permit the incorporation of unnatural amino acids into any amino acid position in a polypeptide. Thus, placement of the first and second chemically reactive unnatural amino acids in the carrier and target polypeptides, respectively, can optionally be chosen based on, e.g., whether placement in that location would change, e.g., the conformations, biological activities, pharmacological activities, stabilities, bioavailabilities, or other properties, of the carrier polypeptide, of the target polypeptide, or of the resulting carrier-target polypeptide conjugate.

In one illustrative, but non-limiting example described in more detail below, a p-acetylphenylalanine, which has been incorporated into HSA, can be reacted with a $\epsilon$-(2-(aminooxy)acetyl)-L-lysine, which has been incorporated into ABT-510, via oxime ligation to produce an HSA-ABT-510 conjugate with an increased serum half-life. It will be appreciated that illustrations in the Example below are not the only embodiments of the invention. As will be apparent from the description herein, any of a wide variety of chemical ligation reactions can be used to couple a carrier polypeptide that includes a first reactive unnatural amino acid to a target polypeptide that includes a second reactive unnatural amino acid, wherein the coupling entails reacting the first and second unnatural amino acids.

In various embodiments of the invention, first and second unnatural amino acid are optionally reacted via one or more of an electrophile-nucleophile reaction, an oxime ligation, a ketone reaction with a nucleophile, an aldehyde reaction with a nucleophile, a reaction between a carbonyl group and a nucleophile, a reaction between a sulfonyl group and a nucleophile, an esterification reaction, a reaction between a hindered ester group and a nucleophile, a reaction between a thioester group and a nucleophile, a reaction between a stable imine group and a nucleophile, a reaction between an epoxide group and a nucleophile, a reaction between an aziridine group and a nucleophile, a reaction between an electrophile and an aliphatic or aromatic amine, a reaction between an electrophile and a hydrazide, a reaction between an electrophile and a carbohydrazide, a reaction between an electrophile and a semicarbazide, a reaction between an electrophile and a thiosemicarbazide, a reaction between an electrophile and a carbonylhydrazide, a reaction between an electrophile and a thiocarbonylhydrazide, a reaction between an electrophile and a sulfonylhydrazide, a reaction between an electrophile and a carbazide, a reaction between an electrophile and a thiocarbazide, a reaction between an electrophile and a hydroxylamine, a reaction between a nucleophile or nucleophiles such as a hydroxyl or diol and a boronic acid or ester, a transition metal catalyzed reaction, a palladium catalyzed reaction, a copper catalyzed heteroatom alkylation reaction, a cycloaddition reaction, a 1,3, cycloaddition reaction, a 2,3 cycloaddition reaction, an alkyne-azide reaction, a Diels-Alder reaction, or a Suzuki coupling reaction. Some of these reactions are described in further detail below.

Oxime Ligation

Oxime ligation was first used in the chemoselective ligation of unprotected polypeptides in an effort to produce a synthetic macromolecule of controlled structure of a molecular weight greater than 10 kD (Rose (1994) "Facile Synthesis of Homogenous Artificial Proteins." *JACS* 116: 30-33). In a first step, a purified polypeptide that carries an aldehyde group and a second purified polypeptide that carries an aminooxy group are prepared. In a second step, the two polypeptides spontaneously self-assemble under very mild conditions through formation of an oxime bond. The resulting oximes are stable in water at room temperature at pH 2-7.

As described in the Example below, an HSA-ABT-510 conjugate was produced by reacting the aminooxy group of a $\epsilon$-(2-(aminooxy)acetyl)-L-lysine residue in an ABT-510 variant with the keto group of a p-acetylphenylalanine residue in an HSA variant at a pH<5. The aminooxy group undergoes a selective oxime ligation with the keto group to covalently link the $\epsilon$-(2-(aminooxy)acetyl)-L-lysine to the p-acetylphenylalanine, thus covalently coupling the HSA to the ABT-510.

1,3-Dipolar Cycloaddition Reactions 1,3-dipolar cycloaddition, also known as "click" chemistry, is the reaction between a 1,3-dipole and a dipolarophile, e.g., a substituted alkene, to form a five-membered ring. One useful example of a 1,3 dipolar cycloadditon is the Azide-Alkyne Huisgen Cycloaddition, e.g., a 1,3-dipolar cycloaddition between an azide and a terminal or internal alkyne to give a 1,2,3-triazole. This copper(I)-catalyzed reaction is mild and very efficient, requiring no protecting groups, and requiring no purification in many cases (Rostovtsev et al. (2002) "A Stepwise Huisgen Cycloaddition Process: Copper (I)-Catalyzed Regioselective Ligation of Azides and Terminal Alkynes" *Angew Chem Int Ed* 41: 2596-2599). Because this reaction involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe et al. (2002) "Peptidotriazoles on solid phase: [1,2,3]-triazoles by regiospecific copper(i)-catalyzed 1,3-dipolar cycloadditions of terminal alkynes to azides." *J Org Chem* 67: 3057-3064; and Rostovtsev et al. (2002) "A Stepwise Huisgen Cycloaddition Process: Copper(I)-Catalyzed Regioselective Ligation of Azides and Terminal Alkynes" *Angew Chem Int Ed* 41: 2596-2599. The azide and alkyne functional groups are largely inert towards biological molecules and aqueous environments, which allows the use of the Azide-Alkyne Huisgen Cycloaddition in the coupling of, e.g., carrier polypeptides to target polypeptides. The triazole has similarities to the ubiquitous amide moiety found in nature, but unlike amides, is not susceptible to cleavage. Additionally, triazoles are nearly impossible to oxidize or reduce.

Suzuki Coupling Reactions

A target polypeptide variant (or carrier polypeptide variant) comprising an surface-exposed unnatural amino acid with an aryl iodide can be covalently attached to a carrier polypeptide variant (or target polypeptide variant) comprising a surface-exposed boronic unnatural amino acid residue, e.g., a p-boronophenylalanine, an m-boronophenylalanine, or an o-boronophenylalanine, through a palladium catalyzed Suzuki coupling. For a description of this chemistry, see, e.g., Miyaura and Suzuki (1995) "Palladium-Catalyzed Cross-Coupling Reactions of Organoboron Compounds," *Chemical Reviews* 95: 2457 and Suzuki (1999) "Recent advances in the cross-coupling reactions of organoboron derivatives with organic electrophiles, 1995-1998," *Journal of Organometallic Chemistry* 576:147. Aryl iodides are reactive groups with a variety of uses in organometallic chemistry, including silylation, aminocarbonylation, Heck Arylation, vinylation, cross-coupling with aryl acetylenes, and many others. Further details regarding the use of unnatural amino acids in Suzuki coupling reactions are elaborated in U.S. patent application Ser. No. 12/262,025, entitled, "A Genetically Encoded Boronate Amino Acid", filed Oct. 30, 2008 and Int'l Application PCT/US2008/081868 entitled "A Genetically Encoded Boronate Amino Acid," filed Oct. 30, 2008.

Copper-Catalyzed Heteroatom Alkylation Reactions

A target polypeptide variant or carrier polypeptide variant that comprises an unnatural amino acid residue that includes a boronate group can participate in copper catalyzed heteroatom alkylation reactions (Chan et al. (2003) "Copper promoted C—N and C—O bond cross-coupling with phenyl and pyridylboronates." Tetrahedron Letters 44: 3863), asymmetric reductions (Huang et al (2000) "Asymmetric reduction of acetophenone with borane catalyzed by chiral oxazaborolidinone derived from L-a-amino acids." *Synthetic Communications* 30: 2423), Diels-Alder reactions (Ishihara and Yamamoto (1999) "Arylboron Compounds as Acid Catalysts in Organic Synthetic Transformations." *European Journal of Organic Chemistry* 3: 527-538), as well as a variety of other transformations.

A boronic unnatural amino acid residue present on the surface of a carrier or target polypeptide variant can also be used to form reversible boronic esters with unnatural amino acid residues on a corresponding target or carrier polypeptide variant that includes an alcohol group a diol an amino-alcohol, or a diamine containing moiety. For example, boronic acids form reversible covalent complexes with diols. For an early description of this chemistry, see Lorand and Edwards (1959) "Polyol Complexes and Structure of the Benzeneboronate Ion." *Journal of Organic Chemistry* 24: 769-774. Reversible complexes can also be formed with aminoalcohols (Springsteen et al. (2001) "The Development of Photometric Sensors for Boronic Acids." *Bioorganic Chemistry* 29: 259-270), amino acids (Mohler and Czarnik (1994) "Alpha-Amino Acid Chelative Complexation by an Arylboronic Acid. [Erratum to document cited in CA119(17):181171a]." *JACS* 116: 2233; Mohler and Czarnik (1993) "Alpha-Amino-Acid Chelative Complexation by an Arylboronic Acid," *JACS* 115: 7037-7038) alkoxides (Cammidge and Crépy (2004) "Synthesis of chiral binaphthalenes using the asymmetric Suzuki reaction." *Tetrahedron* 60: 4377-4386), and hydroxamic acids (Lamandé et al. (1980) "Structure et acidite de composes a atome de bore et de phosphore hypercoordonnes," *Journal of Organometallic Chemistry* 329: 1-29. Further details regarding the utility of boronic amino acids in chemical ligation reactions can be found in U.S. patent application Ser. No. 12/262,025, entitled, "A Genetically Encoded Boronate Amino Acid", filed Oct. 30, 2008; Int'l Application PCT/US2008/081868 entitled "A Genetically Encoded Boronate Amino Acid," filed Oct. 30, 2008; and references cited therein.

[2+3] Cycloaddition Reactions

In certain embodiments, a carrier polypeptide variant comprising a first unnatural amino acid can be coupled to target polypeptide variant comprising a second unnatural amino acid through a [2+3] cycloaddition. In one embodiment, the first unnatural amino acid includes an alkynyl or azido moiety and the second unnatural amino acid includes an azido or alkynyl moiety. For example, the first unnatural amino acid includes the alkynyl moiety (e.g., in unnatural amino acid p-propargyloxyphenylalanine) and the second unnatural amino acid includes the azido moiety. In another example, the first unnatural amino acid includes the azido moiety (e.g., in the unnatural amino acid p-azido-L-phenylalanine) and the second unnatural amino acid includes the alkynyl moiety. The use of unnatural amino acids in [2+3] cycloaddition reactions is described in U.S. patent application Ser. No. 10/826,919, entitled, "Unnatural Reactive Amino Acid Genetic Code Additions", filed Apr. 4, 2004.

Electrophile-Nucleophile Reactions

In some embodiments, one of the reactive groups present in an unnatural amino acid that has been incorporated into a carrier polypeptide variant (or target polypeptide variant) is an electrophilic moiety, and the reactive group present in a second unnatural amino acid that has been incorporated into a target polypeptide variant (or carrier polypeptide variant) is a nucleophilic moiety. Suitable electrophilic moieties that react with nucleophilic moieties to form a covalent bond are known to those of skill in the art. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

The product of the reaction between the nucleophile and the electrophile typically incorporates the atoms originally present, e.g., in the nucleophilic moiety. In some embodiments, the electrophile is an aldehyde or ketone with the nucleophilic moiety including reaction products such as an oxime, an amide, a hydrazone, a reduced hydrazone, a carbohydrazone, a thiocarbohydrazone, a sulfonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids are typically referred to as carbohydrazides or as hydroxamic acids. Linkages with sulfonic acids are typically referred to as sulfonylhydrazides or N-sulfonylhydroxylamines. The resulting linkage can be subsequently stabilized by chemical reduction.

Suitable nucleophilic moieties that can react with aldehydes and ketones to form a covalent bond are known to those of skill in the art. Such nucleophiles include, for example, aliphatic or aromatic amines, such as ethylenediamine. In other embodiments, the unnatural amino acid can include reactive groups such as —$NR^1$—$NH_2$(hydrazide), —$NR^1$(C=O)$NR^2NH_2$ (semicarbazide), —$NR^1$(C=S)$NR^2NH_2$ (thiosemicarbazide), —(C=O)$NR^1NH_2$ (carbonylhydrazide), —(C=S)$NR^1NH_2$ (thiocarbonylhydrazide), —($SO_2$)$NR^1NH_2$ (sulfonylhydrazide), —$NR^1NR^2$(C=O)$NR^3NH_2$ (carbazide), —$NR^1NR^2$(C=S)$NR^3NH_2$(thiocarbazide), or —O—$NH_2$(hydroxylamine), where each $R^1$, $R^2$, and $R^3$ is independently H, or alkyl having 1-6 carbons, preferably H. In one aspect of the invention, the reactive group is a hydrazide, hydroxylamine, carbohydrazide or a sulfonylhydrazide.

Still other reactive chemistries also find use with the invention, including but not limited to the Staudinger ligation and the olefin metathesis chemistries (see, e.g., Mahal et al. (1997) "Engineering Chemical Reactivity on Cell Surfaces Through Oligosaccharide Biosynthesis." *Science* 276: 1125-1128). Many other coupling chemistries are also applicable, and can be used, depending on the unnatural amino acids to be incorporated into the carrier and target polypeptide. Such reactions are well known to those of skill in the are and are described in further detail in, e.g., Dawson et al. (1994) "Synthesis of Proteins by Native Chemical Ligation." *Science* 266: 776-779; Lemieux et al. (1998) "Chemoselective ligation reactions with proteins, oligosaccharides and cells." *TIBS* 16: 506-513; Knipe, Chris. *Organic Reaction Mechanisms*, 2004. New York: Wiley, 2004; and others.

Pharmaceutical Compositions and their Administration

The carrier polypeptide-target polypeptide conjugates of the invention are optionally employed for therapeutic uses, e.g., in combination with a suitable pharmaceutical carrier. Such compositions comprise, e.g., a therapeutically effective amount of the conjugate, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the conjugates of the invention.

Therapeutic compositions comprising one or more carrier polypeptide-target polypeptide conjugates of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to unconjugated target proteins (e.g., comparison of a carrier polypeptide-target peptide conjugate, e.g., an HSA-TSP-1 conjugate (or an HSA-ABT-510 conjugate), to a TSP (or ABT-510) that is not conjugated to an HSA and which does not comprise any unnatural amino acids), i.e., in a relevant assay.

Administration is by any of the routes normally used for introducing a molecule into ultimate contact with blood or tissue cells. The carrier-peptide/target polypeptide conjugates of the invention are administered in any suitable manner, optionally with one or more pharmaceutically acceptable carriers. Suitable methods of administering such conjugates in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Pharmaceutically acceptable carriers and excipients are well known in the art, and one or more conjugates of the invention can be formulated into pharmaceutical compositions by well-known methods (see, e.g., Remington: The Science and Practice of Pharmacy, 21st edition, A. R. Gennaro, Ed., Mack Publishing Company (2005); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

Carrier polypeptide-target polypeptide conjugates of the invention can be administered by a number of routes including, but not limited to: oral, intravenous, intraperitoneal, intramuscular, transdermal, subcutaneous, topical, sublingual, or rectal means. Carrier polypeptide-target polypeptide conjugates can also be administered via liposomes. Such administration routes and appropriate formulations are generally known to those of skill in the art.

The conjugates of the invention, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for carrier polypeptide-target polypeptide conjugate therapeutics, along with formulations in current use, provide preferred routes of administration and formulation for the conjugates of the invention.

The dose administered to a patient, in the context of the present invention, is sufficient to effect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the carrier polypeptide-target polypeptide conjugate employed and the condition of the patient, as well as the body weight or surface area of the patient to be treated. The size of the dose is also determined by the existence, nature, and extent of any adverse side-effects that accompany the administration of a particular composition/formulation, or the like in a particular patient.

In determining the effective amount of the composition/formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, e.g., to a 70 kilogram patient, is typically in the range equivalent to dosages of currently-used therapeutic proteins, adjusted for the altered activity or serum half-life of the relevant carrier polypeptide-target polypeptide conjugate. The compositions/formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the conjugates of the present invention are administered at a rate determined by the LD-50 of the relevant formulation, and/or observation of any side-effects of the carrier polypeptide-target polypeptide conjugate at various concentrations, e.g., as applied to the mass and overall health of the patient. Administration can be accomplished via single or divided doses. General Methods for preparing administrable compositions are known to those skilled in the art and are described in more detail in e.g., Remington: The Science and Practice of Pharmacy, 21st edition, A. R. Gennaro, Ed., Mack Publishing Company (2005).

If a patient undergoing infusion of a formulation comprising one or more conjugates of the invention develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines Treatment is slowed or discontinued depending upon the severity of the reaction.

A variety of subjects can benefit from the therapeutic treatments, and/or prophylactic treatments provided by the carrier polypeptide-target polypeptide conjugates provided by the invention. Humans, and such animals including, but not limited to, domestic livestock, such as cows, pigs, goats, sheep, chickens, and/or other common farm animals can be administered compositions and formulations that include the conjugates described herein. Common household pets, e.g., cats, dogs, parrots, parakeets, etc., can also benefit from being administered a therapeutic or prophylactic carrier polypeptide-target polypeptide conjugate.

Further details regarding the use of animal models and animal subjects in biomedical testing and veterinary treatment are elaborated in, e.g., Ng, Chow, and Ogden, eds. *Using Animal Models in Biomedical Research: A Primer for the Investigator*. First Edition. Singapore: World Scientific Publishing Company, 2008; Conn, ed. *Sourcebook of Models for Biomedical Research*. Totowa, N.J.: Springer, 2008; Woodhead, ed. *Nonmammalian Animal Models for Biomedical Research* (Vol 1). New York: Academic Press, 1990. See also, e.g., Adams, ed. *Veterinary Pharmacology and Therapeutics*. Eighth Edition. USA: Wiley-Blackwell, 2001; Kahn and Line, Eds. Merck Veterinary Manual. Ninth Edition. USA: Merck, 2005; and references cited therein.

Carrier polypeptide-target polypeptide conjugates provided by the invention can be administered not only to treat a disease state in a subject, e.g., a human, but also to perform treatment efficacy tests, as well as metabolic tests, toxicology tests, and specific tests to determine the effects of the carrier peptide-target polypeptide conjugates on reproductive function or embryonic toxicity, or to determine their carcinogenic potential. Performing such observational studies can entail administering the conjugates of the invention to a variety of animal subjects. Those of skill in the art will be quite familiar with numerous medical tests and measurements to help in selection of animal subjects that are to be administered the compositions/formulations that include the conjugates of the invention. Such animal subjects include, but are not limited to, e.g., mammals such as goats sheep, camels, cows, pigs, rabbits, horses, hamsters, non-human primates (monkeys, including cynomolgus monkeys, baboons, Old World Monkeys, and chimpanzees), guinea pigs, rats, mice, and/or cats. Birds such as, e.g., domestic fowl (chickens, turkeys), cockatiels, psittacine birds, and cage and/or aviary birds, as well as bird embryos, can also be used in the research and development, production, quality control, or safety testing of the carrier polypeptide-target polypeptide conjugates provided by the invention.

Fish, such as zebrafish, platyfish, and swordtails; amphibians, including, e.g., frogs and salamanders; and reptiles (snakes, lizards, and turtles) can also be used in a wide variety of tests to determine the safety, effective dose, and/or toxicology of the compositions described herein and/or the methods of their administration. See, e.g., Barry, et al. (2002) "Information Resources for Reptiles, Amphibians, Fish, and Cephalopods Used in Biomedical Research." United States Department of Agriculture National Agricultural Library Animal Welfare Information Center, and the references cited therein.

Kits and Articles of Manufacture

Kits are also a feature of the invention. For example, kits can optionally contain any one or more carrier polypeptide-target polypeptide conjugates provided by the invention. Alternatively or additionally, kits can contain reagents for the synthesis of carrier polypeptide variants that comprise first chemically reactive unnatural amino acids and/or target polypeptides variants, e.g., small therapeutic peptides, that comprise second chemically reactive unnatural amino acids. Such reagents can include, e.g., the reactive unnatural amino acids, host cells, e.g., methylotrophic yeast cells that include orthogonal translation system components suitable for the production of carrier polypeptide and/or target polypeptide variants comprising unnatural amino acids, solutions in which to perform ligation reactions that produce the conjugates of the invention, reagents with which to produce therapeutic formulations comprising one or more conjugates of the invention, media, etc. Kits of the invention can include additional components such as instructions to, e.g., construct a methylotrophic yeast strain that can express a carrier polypeptide and/or target polypeptide that comprises unnatural amino acids, perform a chemical ligation reaction to produce a carrier polypeptide-target polypeptide conjugate, etc. The kit can include a container to hold the kit components, instructional materials for practicing any method or any combination of methods herein, instructions for using cells (e.g., methylotrophic yeast cells) provided with the kit, e.g., to produce a carrier and/or target polypeptide of interest that comprises a chemically reactive unnatural amino acid at a selected amino acid position.

EXAMPLE

The following example is offered to illustrate, but not to limit the claimed invention. It is understood that the embodiments described herein are for illustrative purposes only and that various modifications or changes in light thereof will be suggested to persons skilled in the art and are to be included within the spirit and purview of this application and scope of the appended claims.

Expanding the Genetic Repertoire of the Methylotrophic Yeast, Pichia pastoris

To increase the utility of protein mutagenesis with unnatural amino acids, a recombinant expression system in the methylotrophic yeast Pichia pastoris was developed. Aminoacyl-tRNA synthetase/suppressor tRNA (aaRS/tRNA$_{CUA}$) pairs previously evolved in Saccharomyces cerevisiae to be specific for unnatural amino acids were inserted between eukaryotic transcriptional control elements and stably incorporated into the P. pastoris genome. Both the Escherichia coli tyrosyl- and leucyl-RS/tRNA$_{CUA}$ pairs were shown to be orthogonal in P. pastoris and used to incorporate eight unnatural amino acids in response to an amber codon with high yields and fidelities. One example shows that a recombinant human serum albumin mutant containing a keto amino acid (p-acetylphenylalanine) (FIG. 6b, structure 1) can be efficiently expressed in this system and selectively conjugated via oxime ligation to a therapeutic peptide mimetic containing an ϵ-(2-(aminooxy)acetyl)-L-lysine residue. Moreover, unnatural amino acid expression in the methylotrophic yeast was systematically optimized by modulation of aaRS levels to express mutant human serum albumin in excess of 150 mg/L in shake flasks, more than an order of magnitude better than that reported in S. cerevisiae. This methodology should allow the production of high yields of complex proteins with unnatural amino acids whose expression is not practical in existing systems.

Recently, a methodology was developed that makes it possible to genetically encode a wide variety of unnatural amino acids with novel properties (including fluorophores, metal ion chelators, photocaged and photocrosslinking groups, NMR, crystallographic and IR probes, and post-translationally modified amino acids) in both prokaryotic and eukaryotic organisms (Xie & Schultz (2006) "A chemical toolkit for proteins—an expanded genetic code." Nat Rev Mol Cell Biol 7: 775-782; Chin et al. (2003) "An expanded eukaryotic genetic code." Science 301: 964-967; Wang et al. (2006) "Expanding the genetic code." Annu Rev Biophys Biomol Struct 35: 225-249). This is accomplished through the evolution of an orthogonal aminoacyl-tRNA synthetase/suppressor tRNA (aaRS/tRNA$_{CUA}$) pair, designed to selectively insert a desired unnatural amino acid in response to a nonsense or frameshift codon. Thus far, this methodology has been employed to add more than 40 unnatural amino acids to the genetic repertoires of Escherichia coli, Saccharomyces cerevisiae, and several lines of mammalian cells (Chin et al. (2003) "An expanded eukaryotic genetic code." Science 301: 964-967; Wang et al. (2006) "Expanding the genetic code." Annu Rev Biophys Biomol Struct 35: 225-249; Liu et al. (2007) "Genetic incorporation of unnatural amino acids into proteins in mammalian cells." Nat Methods 4: 239-244). Orthogonality in these systems is achieved by transplanting an orthogonal aaRS/tRNA$_{CUA}$ pair with distinct tRNA identity elements into the host organism such that no cross-aminoacylation occurs between the host aminoacylation machinery and the transplanted aaRS/tRNA pair (while still maintaining function in translation). In the current systems, this has proven most successful using aaRS/tRNA$_{CUA}$ pairs derived from the Methanococcus jannaschii tyrosyl-RS/tRNA$_{CUA}$ pair in E. coli (Wang et al. (2001) "A general approach for the generation of orthogonal tRNAs." Chem Biol 8: 883-890) and the E. coli tyrosyl- or leucyl-RS/tRNA$_{CUA}$ pairs in S. cerevisiae (Chin et al. (2003) "An expanded eukaryotic genetic code." Science 301: 964-967; Chin et al. (2003) "Progress toward an expanded eukaryotic genetic code." Chem Biol 10: 511-519) or mammalian cells (Liu et al. (2007) "Genetic incorporation of unnatural amino acids into proteins in mammalian cells." Nat Methods 4: 239-244). Directed evolution is then used to alter the specificity of the orthogonal aaRS so that it recognizes the unnatural amino acid of interest and not an endogenous amino acid.

To apply this methodology for the production of large quantities of proteins that are not easily expressed in bacterial hosts, a recombinant system is desired with low cost, scalability, and the ability to produce complex, post-translationally modified proteins. One such host is Pichia pastoris, which is capable of producing mammalian proteins in yields comparable to those of E. coli (Cereghino et al. (2000) "Heterologous protein expression in the methylotrophic yeast Pichia pastoris." FEMS Microbiol Rev 24: 45-66). Therapeutic proteins such as tumor necrosis factor (TNF), tetanus toxin fragment C (TTC), and human serum albumin (HSA) have afforded expression levels >10 g L$^{-1}$ in high density fermentations (Shekhar (2008) "Pichia power: India's biotech industry puts unconventional yeast to work." Chem Biol 15: 201-202; Clare et al. (1991) "High-level expression of tetanus toxin fragment C in Pichia pastoris strains containing multiple tandem integrations of the gene." Biotechnology (New York) 9: 455-460; Ohya et al. (2005) Optimization of human serum albumin production in methylotrophic yeast Pichia pastoris by repeated fed-batch fermentation." Biotechnol Bioeng 90: 876-887; Sreekrishna et al. (1989) "High-level expression, purification, and characterization of recombinant human tumor necrosis factor synthesized in the methylotrophic yeast Pichia pastoris." Biochemistry 28: 4117-4125). P. pastoris' ability to produce proteins in such yields is attributed to its alcohol oxidase 1 promoter (P$_{AOX1}$), one of the most highly regulated and strongest promoters known (Cos et al. (2006) "Operational strategies, monitoring and control of heterologous protein production in the methylotrophic yeast Pichia pastoris under different promoters: a review." Microb Cell Fact 5: 17). In addition, P. pastoris lacks endotoxins which can contaminate therapeutic proteins expressed in E. coli, and does not produce antigenic α1,3 glycan linkages as does S. cerevisiae (Cregg et al. (1993) "Recent advances in the expression of foreign genes in Pichia pastoris." Biotechnology (New York) 11: 905-910). Additionally, it is now possible to modulate glycosylation patterns in P. pastoris, including control of sialylation (Li et al. (2006) "Optimization of humanized IgGs in glycoengineered Pichia pastoris." Nat Biotechnol 24: 210-215). For these reasons, we undertook the development of methodology to allow unnatural amino acids to be genetically encoded in P. pastoris. Here we report that eight unnatural amino acids were site-specifically introduced into recombinant human serum albumin (rHSA) expressed in this host with high yields and fidelities.

Materials

DNA primers used to perform the experiments described herein (e.g., those listed in FIG. 14 and below) were purchased from Integrated DNA Technology (San Diego, Calif.).

Restriction enzymes used to prepare constructs described below were purchased from New England Biolabs (Beverly, Mass.). The pPIC3.5k vector (map available at http://tools.invitrogen.com/content/sfs/manuals/ppic3.5kpao_man.pdf) and protocols for yeast competency, transformation, and media recipes were purchased from Invitrogen (Carlsbad, Calif.). Multi-Copy *Pichia* Expression Kit Version F manual (Invitrogen Life, T., Vol. K1750-01, Edn. F 85 (Invitrogen Life Technologies, Carlsbad, Calif. 92008; 2005)) is available at http://tools.invitrogen.com/content/sfs/manuals/pichmulti_man.pdf. DNA was amplified in *E. coli* DH10B (Invitrogen) or, when noted, by PCR using platinum pfx (Invitrogen). The rHSA gene (accession BC034023) was obtained from the Mammalian Gene Collection (National Institutes of Health, Bethesda, Md.). All DNA constructs were confirmed by DNA sequencing (Genomics Institute of the Novartis Research Foundation, La Jolla, Calif.). The double auxotrophic *Pichia pastoris* strain, GS200 (his4, arg4), and the pBLARG vector were gracious gifts from the James Cregg laboratory at the Keck Graduate Institute, Claremont, Calif. Transformations of *P. pastoris* and *E. coli* were carried out on a GenePulser Xcell (Bio-Rad, Hercules, Calif.) using 2 and 1 mm electroporation cuvettes (Fisher Scientific, Rochester, N.Y.). Trisglycine (4-20%) SDS-PAGE gels for protein analysis were purchased from Invitrogen. RNA was harvested via the protocols and reagents accompanying the Purelink miRNA isolation kit (Invitrogen) or Ribo-pure-yeast kit (Ambion, Austin, Tex.). All relative gel band densities were determined using Photoshop CS2 (Adobe, San Jose, Calif.).

Design of a Two Gene Cassette Expression System

Due to the relative instability of autonomously replicating plasmids in *P. pastoris* (Higgins et al. (1998) "Introduction to *Pichia pastoris*." *Methods Mol Biol* 103: 1-15), a system was devised in which the target gene of interest (e.g., rHSA) and the aaRS/tRNA$_{CUA}$ pair were encoded in cassettes on two separate plasmids and stably integrated into the genome. FIG. 1 provides vectors that were used to construct the cassettes for amber suppression in *P. pastoris*. Selectable markers on each plasmid are indicated by the white arrows. Replication origins are indicated by black arrows. Promoters and transcriptional terminator elements are indicated by vertically striped arrows. The double auxotroph *P. pastoris* strain GS200 (arg4, his4) was used as the host strain for protein expression, and the gene of interest, e.g., HSA, was inserted into the commercially available pPIC3.5k plasmid (HIS4, Gen$^R$) (FIG. 1a) (Invitrogen Life, T., Vol. K1750-01, Edn. F 85 (Invitrogen Life Technologies, Carlsbad, Calif. 92008; 2005)).

rHSA was used as a model protein given its utility in producing fusion proteins or peptide bioconjugates that enhance the serum half-life of short lived therapeutic polypeptides (Kim et al. (2003) "Development and characterization of a glucagon-like peptide 1-albumin conjugate: the ability to activate the glucagon-like peptide 1 receptor in vivo." *Diabetes* 52: 751-759; Huang et al. (2008) "Preparation and characterization of a novel exendin-4 human serum albumin fusion protein expressed in *Pichia pastoris*." *J Pept Sci* 14: 588-595; Chuang et al. (2002) "Pharmaceutical strategies utilizing recombinant human serum albumin" *Pharm Res* 19: 569-577). Expression of rHSA in *E. coli* and *S. cerevisiae* is not practical due to the protein's complex disulfide crosslinkages. However, such post-translational modifications can be made in *P. pastoris*. Additionally, the 24 amino acid mammalian "pre-pro" leader sequence of HSA (FIG. 1e) is fully compatible with expression in *P. pastoris* and allows export of the mature protein into the media (Kobayashi (2006) "Summary of recombinant human serum albumin development." *Biologicals* 34: 55-59). The pre-pro leader peptide is cleaved during transport to yield the mature protein (e.g., rHSA$_{E37X}$). The 37$^{th}$ residue in rHSA, relative to SEQ ID NO: 1 denotes the unnatural amino acid incorporated in response to the amber codon.

First, cassettes encoding rHSA$_{WT}$, and rHSA$_{E37X}$ that could be used to transform GS200 were prepared. The pPIC3.5K-rHSA (wild type rHSA) construct was prepared as follows: The wild type rHSA gene was obtained from the Mammalian Gene Collection (NIH), gene accession BC034023. For compatibility with pPIC3.5k linearization (Invitrogen Life, T., Vol. K1750-01, Edn. F 85 (Invitrogen Life Technologies, Carlsbad, Calif. 92008; 2005)), BglII sites were removed from rHSA by a modified Quik Change mutagenesis (Stratagene) protocol (Zheng et al. (2004) "An efficient one-step site-directed and site-saturation mutagenesis protocol." *Nucleic Acids Res* 32: e115) using primers (IDT): –BglII 1F, 5'-GAC AGA CCT TAC CAA AGT CCA CAC GGA ATG CTG CCA TG-3' (SEQ ID NO: 4) and –BglII 1R, 5'-GGT AAG GTC TGT CAC TAA CTT GGA AAC TTC TGC AAA CTC AGC TTT GGG-3' (SEQ ID NO: 5) for BglII$_{781}$, and –BglII 2F, 5'-CAT GGA GAC CTG CTT GAA TGT GCT GAT GAC AGG GCG G-3' (SEQ ID NO: 6) and –BglII 2R,5'-CAA GCA GGT CTC CAT GGC AGC ATT CCG TGT GGA C-3' (SEQ ID NO: 7) for BglII$_{817}$ to create rHSA$_{WT}$. rHSA$_{WT}$, was amplified using primers: HSA Forward, 5'-ATC CGA GGA TCC AAA CGA TGA AGT GGG TAA CCT TTA TTT CCC TTC TTT TTC-3' (SEQ ID NO: 8) and HSA Reverse, 5'-GCT AAC GAA TTC ATT ATA AGC CTA AGG CAG CTT GAC TTG CAG C-3' (SEQ ID NO: 9), digested with EcoRI and BamHI (NEB) and ligated into the similarly digested pPIC3.5k vector (Invitrogen, vector map available at http://tools.invitrogen.com/content/sfs/manuals/ppic3.5kpao_man.pdf) to create pPIC3.5k-rHSA$_{WT}$ (or pPIC3.5k-rHSA$_{E37X}$, as described below). Constructs were confirmed by DNA sequencing and amplified in *E. coli* DH10B (Invitrogen).

The Glu37TAG mutant rHSA (rHSA$_{E37X}$) construct was generated by PCR mutagenesis. The Glu37 codon was replaced by the amber codon TAG using the modified Quik Change protocol and the primers: Glu37 F', 5'-GAT GCC CTT TGC TCA GTA TCT TCA GCA GTG TCC ATT TTA GGA TCA T-3' (SEQ ID NO: 10) and Glu37 R', 5'-GTT TTT GCA AAT TCA GTT ACT TCA TTC ACT AAT TTT ACA TGA TCC TAA AAT GG-3' (SEQ ID NO: 11). Glu37 is in a solvent accessible helix which should facilitate the conjugation of peptides to a chemically reactive unnatural amino acid (i.e., p-acetylphenylalanine, FIG. 6b, Structure 1) introduced at this site, and ensure that incorporation of relatively bulky groups minimally disrupt native protein structure and folding. rHSA$_{E37X}$ was then amplified using primers: HSA Forward, 5'-ATC CGA GGA TCC AAA CGA TGA AGT GGG TAA CCT TTA TTT CCC TTC TTT TTC-3' (SEQ ID NO: 8) and HSA Reverse, 5'-GCT AAC GAA TTC ATT ATA AGC CTA AGG CAG CTT GAC TTG CAG C-3' (SEQ ID NO: 9), digested with EcoRI and BamHI (NEB) and ligated into the similarly digested pPIC3.5k vector, as described above for HSA$_{WT}$, placing HSA$_{E37X}$ under the transcriptional control of the AOX1 promoter and terminator. The rHSA$_{E37X}$ construct, pPIC3.5k-rHSA$_{E37X}$, was confirmed by DNA sequencing, as described above.

Linearization of pPIC3.5k-rHSA$_{E37X}$ or pPIC3.5k-rHSA$_{WT}$ in the 5' AOX1 promoter allows genomic integration of one or more copies of the transformed cassette; generally more copies result in higher overall yields of target protein (Buckholz et al. (1991) "Yeast systems for the commercial production of heterologous proteins." *Biotechnology* (N Y) 9: 1067-1072). Integration in this manner leaves the AOX1 gene intact, retaining the yeast's ability to rapidly utilize methanol (Mut⁺ phenotype). Alternatively, gene replacement can be carried out by linearization on either side of AOX1 gene, resulting in replacement of the AOX1 gene by the pPIC3.5k vector (Invitrogen Life, T., Vol. K1750-01, Edn. F 85 (Invitrogen Life Technologies, Carlsbad, Calif. 92008; 2005)). Yeast lacking AOX1 rely on the weaker AOX2 gene for methanol utilization and are phenotypically mut$^S$. Because expression of rHSA is commonly carried out with mut$^s$ yeast (Kupcsulik et al. (2005) "Optimization of specific product formation rate by statistical and formal kinetic model descriptions of an HSA producing *Pichia pastoris* Mut(S) strain." *Chem Biochem Eng Q* 19: 99-108), pPIC3.5k HSA$_{E37X}$ and pPIC3.5k-rHSA$_{WT}$ were linearized and used to replace the AOX1 gene to yield GS200-rHSA$_{E37X}$ or GS200-rHSA$_{WT}$ (both strains are HIS4, arg4, Gen$^R$, mut$^s$). Successful transformants grew normally on minimal media plates lacking histidine and on rich media plates containing up to 0.25 mg/mL of the aminoglycoside antibiotic Geneticin®.

To transform GS200 with a pPIC3.5k HSA$_{E37X}$ or pPIC3.5k-rHSA$_{WT}$ cassette, 20 µg of pPIC3.5k-rHSA$_{E37X}$ or pPIC3.5k-rHSA$_{WT}$ was linearized with BglII (NEB), concentrated to 10 µl by ethanol precipitation, added to 80 µl of freshly competent GS200 in a 2 mm electroporation cuvette (Fisher), and electroporated with the *P. pastoris* settings (2000V, 25 µF, 200Ω) on a GenePulser Xcell (BioRad). Cells were recovered in 1 ml cold 1 M sorbitol. 250 µl of recovered cells was plated on regeneration dextrose Bacto agar (RDB) plates (15 cm) supplemented with 4 mg ml$^{-1}$ L-arginine (arg) and incubated at 30° C. After 3 days, colonies were picked into 96 well 2 ml blocks (Nunc) with 1 ml yeast peptone dextrose (YPD) media and grown overnight (29.2° C., 300 r.p.m.). The cultures were diluted 1:100 and 1-2 µl replica plated on YPD agar plates containing 0.25 mg ml$^{-1}$ Geneticin® (Invitrogen) and incubated at 30° C. After 4 days, GS200-rHSA$_{E37X}$ transformant G3 showed good growth, was picked, and made competent. A GS200-rHSA$_{WT}$ clone that showed good growth was also picked.

To integrate the orthogonal aaRS/tRNA$_{CUA}$ pair into the genome, the previously developed pPR1-P$_{PGK1}$+3SUP4-tRNA$_{CUA}^{Tyr}$ vector (Chen et al. (2007) "An improved system for the generation and analysis of mutant proteins containing unnatural amino acids in *Saccharomyces cerevisiae*." *J Mol Biol* 371: 112-122) (FIG. 1b) for optimized amber suppression and recombinant over-expression in *S. cerevisiae* was modified. The p-acetylphenylalanine-(pApa, FIG. 6b, Structure 1) specific aminoacyl-tRNA synthetase (pApaRS), previously evolved in *S. cerevisiae* (Zhang et al. (2003) "A new strategy for the site-specific modification of proteins in vivo." *Biochemistry* 42, 6735-6746), was inserted between the alcohol dehydrogenase 1 promoter (P$_{ADH1}$) and terminator (T$_{ADH1}$) with a His$_6$-tag to assay its expression.

To prepare the aaRS/tRNA$_{CUA}$ pair for integration into the *P. pastoris* genome, the pPR1-P$_{PGK1}$+3SUP4-tRNA$_{CUA}^{Tyr}$ vector (Chen et al. (2007) "An improved system for the generation and analysis of mutant proteins containing unnatural amino acids in *Saccharomyces cerevisiae*." *J Mol Biol* 371: 112-122) harboring the pApaRS was amplified by PCR, excluding the TRP and 2µ origin regions, to add restriction sites KpnI and HindIII with primers: pESC F, 5'-TAC CAC TAG AAG CTT GGA GAA AAT ACC GCA TCA GGA AAT TGT AAA CGT-3' (SEQ ID NO: 12) and pESC R, 5'-GTG AGG GCA GGT ACC GTT CTG TAA AAA TGC AGC TCA GAT TCT TTG TTT G-3' (SEQ ID NO: 13) and digested with HindIII and KpnI (NEB). The ARG4 coding region was amplified from pBLARG (gift from the James Cregg laboratory, Keck Graduate Institute, Claremont, Calif.) with primers: ARG4 F new, 5'-AAA TAT GGT ACC TGC CCT CAC GGT GGT TAC GGT-3' (SEQ ID NO: 14) and ARG4 R new, 5'-CAT TTC AAG CTT CTA GTG GTA GGA ATT CTG TAC CGG TTT AC-3' (SEQ ID NO: 15), digested with KpnI and HindIII and ligated into the similarly digested pPR1-P$_{PGK1}$+ 3SUP4-tRNA$_{CUA}^{Tyr}$ PCR product to create the recombinant eukaryotic ARG4 vector, pREAV-P$_{ADH1}$-pApaRS. The pREAV-P$_{ADH1}$-pApaRS was amplified by PCR, excluding the P$_{ADH1}$-pApaRS-T$_{ADH1}$ region, to add restriction sites AscI and AflII with primers: pESC-AOX-KETO F, 5'-ATC GTA CTT AAG GAA AGC GTA CTC AAA CAG ACA ACC ATT TCC-3' (SEQ ID NO: 16) and pESC-AOX-KETO R, 5'-TTC TCA GGC GCG CCA TCG CCC TTC CCA ACA GTT GCG-3' (SEQ ID NO: 17). Constructs were confirmed by size mapping and sequencing.

Figure 1C:
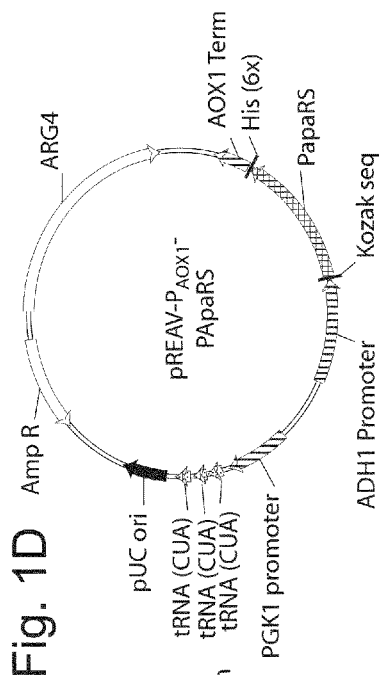

The cognate *E. coli* tRNA$_{CUA}^{Tyr}$ lacking the 5' CCA was inserted as three tandem repeats behind the phosphoglycerate kinase 1 promoter (P$_{PGK1}$). To aid in posttranscriptional processing, the tRNAs were flanked by regions from the yeast suppressor tRNA gene, SUP4, as previously described (Chen et al. (2007) "An improved system for the generation and analysis of mutant proteins containing unnatural amino acids in *Saccharomyces cerevisiae*." *J Mol Biol* 371: 112-122). Eukaryotic downstream processing adds the 5' CCA that is required for tRNA function. The 2µ origin and phosphoribosyl anthranilate isolmerase (TRP) marker of pPR1-P$_{PGK1}$+ 3SUP4-tRNA$_{CUA}^{Tyr}$ were replaced by the arginosuccinate lyase (ARG4) coding region to give the recombinant eukaryotic ARG4 vector (pREAV-P$_{ADH1}$-pApaRS) (FIG. 1c). Propagation of this cassette is only possible in the event of genomic incorporation since it lacks a eukaryotic origin of replication. Transformations to create GS200-rHSA$_{E37X}$/pREAV-P$_{ADH1}$-pApaRS were carried out using the protocol described above with competent G3 (e.g., competent GS200-rHSA$_{E37X}$ transformant), except recovered cells were plated on RDB plates lacking L-histidine and arginine. After 3 days colonies were picked into 96 well 2 ml blocks and rescreened as above for resistance to 0.25 mg ml$^{-1}$ Geneticin®. GS200-rHSA$_{WT}$/pREAV P$_{ADH1}$-pApaRS (HIS4, ARG4, Gen$^R$, mut$^s$) was created in identical fashion to isolate colony F2. Thus, linearization of pREAV-P$_{ADH1}$-pApaRS in the ARG4 coding region, and subsequent transformation into GS200-HSA$_{E37X}$ and GS200-HSA$_{WT}$ gave the fully prototrophic *P. pastoris* GS200-HSA$_{E37X}$/pREAV-P$_{ADH1}$-pApaRS and GS200-HSA$_{WT}$/pREAV-P$_{ADH1}$-pApaRS strains, respectively. (Both strains are HIS4, ARG4, Gen$^R$, mut$^s$).

Amber Suppression in *P. pastoris*.

All protein expression experiments followed protocols for mut$^s$ found in the Multi-Copy *Pichia* Expression Kit (Invitrogen Life, T., Vol. K1750-01, Edn. F 85 (Invitrogen Life Technologies, Carlsbad, Calif. 92008; 2005)). 14 colonies for GS200-rHSA$_{E37X}$/pREAV-P$_{ADH1}$-pApaRS or GS200-rHSA$_{WT}$/pREAV-P$_{ADH1}$-pApaRS were picked from plates containing 0.25 mg ml$^{-1}$ Geneticin® and grown to near saturation (OD$_{600}$≈12-18) in 10 ml buffered glycerol-complex medium (BMGY) (29.2° C., 300 r.p.m.). Cultures were centrifuged at 1500 g (10 min), and resuspended in 2 ml buffered methanol-complex media (BMMY) with 2 mM pApa amino acid (SynChem, Des Plaines, Ill.). Growth was continued for 6 days, with methanol supplementation to 0.5% every 24 hrs. 200 µl (10% culture volume) of media or sterile water was added every 24 hrs to account for evaporation. 50 µl of media was removed every 24 hrs and cleared of cells by centrifugation at 3000 g (5 min) 25 µl of the cleared media was added to 12.5 µl of SDS loading buffer, heated for 1 min at 95° C., and run on a SDS-PAGE gel (Invitrogen) (150 V 1 h).

Amber suppression only occurs in yeast harboring both vectors grown with methanol and pApa amino acid (pApa AA). Clones isolated from GS200-HSA$_{WT}$/pREAV-P$_{ADH1}$-pApaRS produced full length rHSA$_{WT}$ (66.5 kDa) visible by Coomassie stain (40% methanol, 10% acetic acid, 50% water, 0.1% (w/v) Coomassie Brilliant Blue R250 (Sigma-Aldrich)) on a sodium dodecyl sulfate polyacrylamide gel-electrophoresis (SDS-PAGE) gel after two to three days when grown under methanol inducing conditions. The expression of rHSA$_{WT}$ peaked after 6 days. Clone F2-wt for GS200-rHSA$_{WT}$/pREAV-P$_{ADH1}$-pApaRS showed highest expression and was used in further comparisons. In contrast, clones from GS200-HSA$_{E37X}$/pREAV-P$_{ADH1}$-pApaRS failed to produce full length rHSA$_{E37pApa}$ when grown for six days with methanol as the primary carbon source and pApa amino acid supplementation. (See, e.g., FIG. 2b; lane 2 is GS200; lane 3 is GS200-HSA$_{E37X}$; lane 4 is GS200-pREAV-P$_{AOX1}$-pApaRS; lanes 5-7 are GS200-HSA$_{E37X}$/pREAV-P$_{AOX1}$-pApaRS; and lane 8 is GS200-HSA$_{WT}$/pREAV-P$_{ADH1}$-pApaRS.

Figure 2A:
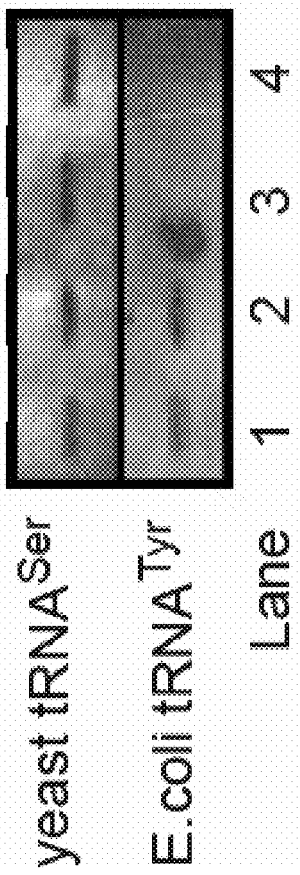
FIG. 2 shows the results of experiments that were performed to determine the fidelity and specificity with which the unnatural amino acid p-acetylphenylalanine is incorporated into HSA in response to a selector codon at amino acid position 37 in *P. pastoris*. (a) A Northern blot (bottom gel) was used to assay suppressor tRNA transcription in *S. cerevisiae*+pPR1-$P_{PGK1}$-3SUP4-tRNA (lane 1) and *P. pastoris*+ pREAV-$P_{ADH1}$-pApaRS (lane 2). For a negative control, lanes 3 and 4 are *S. cerevisiae* and *P. pastoris* strains lacking vectors, respectively. The top gel shows a Northern blot for the endogenous serine tRNA and illustrates equal miRNA preparations for all samples. (b) To assay the fidelity of the system, 25 µl of cleared media from 6 days of growth was analyzed on a denaturing SDS-PAGE gel and stained with Coomassie. Lane 2 is GS200; lane 3 is GS200-rHSA$_{E37X}$; lane 4 is GS200-pREAV-$P_{AOX1}$-pApaRS; lanes 5-7 are GS200-rHSA$_{E37X}$/pREAV-$P_{AOX1}$-pApaRS; and lane 8 is GS200-rHSA$_{WT}$/pREAV-$P_{ADH1}$-pApaRS. Amber suppression only occurs in yeast harboring both vectors and grown with methanol and pApa amino acid (pApa AA). (c) MS/MS fragmentation of a tryptic peptide (top) containing the unnatural amino acid pApa (denoted E*) at residue 37 of mature rHSA$_{E37pApa}$. The substitution is supported without ambiguity by the observed fragment ion series.

Genomic integration of all constructs was confirmed by genomic PCR (FIG. 7; four clones were chosen from one transformation and labeled 1-4). Expected PCR products were rHSA (1851 bp), pApaRS (1317 bp), and tRNA cassette (1100 bp). The lack of pApaRA amplification in clone 2 is likely a technical artifact. The bottom gel of FIG. 2a depicts the results of a northern blot performed to assay tRNA$_{CUA}$ expression in S. cerevisiae+pPR1-P$_{PGK1}$-3SUP4-tRNA (lane 1) and P. pastoris+pREAV-P$_{ADH1}$-pApaRS (lane 2). For a negative control, lanes 3 and 4 are S. cerevisiae and P. pastoris strains lacking vectors, respectively. The top gel of FIG. 2a shows a northern blot for the endogenous serine tRNA and illustrates equal miRNA preparation in all samples.

Briefly, northern blots to confirm transcription of the tRNA$_{CUA}$ were performed as follows: two P. pastoris clones, G3-2 and GS200, and two S. cerevisiae clones, SCY4-pPR1-P$_{PGK1}$+2SUP4-tRNA, and SCY4, were grown under their respective expression conditions, and micro RNA (miRNA) harvested. 2 µg of RNA from each sample was loaded onto two 6% Novex TBE-Urea gel (Invitrogen), and run at 180 V for 1 h. RNA was transferred to a Biodyne B nylon membrane (Pall Life Science) using an XCell surelock mini-cell (Invitrogen) in 0.5×TBE buffer (Invitrogen) and accompanying protocols. The membranes were auto cross-linked with UV Stratalinker 2400 (Stratagene, La Jolla, Calif.). Hybridization and detection was carried out with protocols and reagents found in the North2South chemiluminescent hybridization and detection kit (Pierce, Rockford, Ill.). One blot was incubated with biotinylated probes specific for tRNA$^{ser}$: tRNAser cere 1, 5'-/5Biosg/CAT TTC AAG ACT GTC GCC TTA ACC ACT CGG CCA T-3', tRNAser cere 2, 5'-/5Biosg/GAA CCA GCG CGG GCA GAG CCC AAC ACA TTT CAA G-3', tRNAser pich 1, 5'-/5Biosg/CTG CAT CCT TCG CCT TAA CCA CTC GGC CAT CGT A-3', tRNAser pich 2, 5'-/5Biosg/ACA CGA GCA GGG TTC GAA CCT GCG CGG GCA GAG C-3' and the second blot incubated with biotinylated probes specific for tRNA$_{CUA}^{tyr}$:tRNA 5' biot, 5'-/5Biosg/GGA AGG ATT CGA ACC TTC GAA GTC GAT GAC GG-3' and tRNA 3' biot, 5'-/5Biosg/TCT GCT CCC TTT GGC CGC TCG GGA ACC CCA CC-3'. Probes were incubated overnight at 55° C., bound to a streptavidin-horseradish peroxidase (HRP) conjugate, and detected with a luminol/enhancer—stable peroxide solution (Pierce) (FIG. 2a). Relative tRNA amounts were determined by band density. The results of FIG. 2 indicate that transcription of the tRNA$_{CUA}$ was found to be approximately 1.5 times greater in P. pastoris+pREAV-P$_{ADH1}$-pApaRS than the same cassette in S. cerevisiae by northern blot analysis (FIG. 2a).

Briefly, northern blots to confirm transcription of the tRNA$_{CUA}$ were performed as follows: two P. pastoris clones, G3-2 and GS200, and two S. cerevisiae clones, SCY4-pPR1-P$_{PGK1}$+2SUP4-tRNA, and SCY4, were grown under their respective expression conditions, and micro RNA (miRNA) harvested. 2 µg of RNA from each sample was loaded onto two 6% Novex TBE-Urea gel (Invitrogen), and run at 180 V for 1 h. RNA was transferred to a Biodyne B nylon membrane (Pall Life Science) using an XCell surelock mini-cell (Invitrogen) in 0.5×TBE buffer (Invitrogen) and accompanying protocols. The membranes were auto cross-linked with UV Stratalinker 2400 (Stratagene, La Jolla, Calif.). Hybridization and detection was carried out with protocols and reagents found in the North2South chemiluminescent hybridization and detection kit (Pierce, Rockford, Ill.). One blot was incubated with biotinylated probes specific for tRNA$^{ser}$: tRNAser cere 1, 5'-/5Biosg/CAT TTC AAG ACT GTC GCC TTA ACC ACT CGG CCA T-3' (SEQ ID NO: 18), tRNAser cere 2, 5'-/5Biosg/GAA CCA GCG CGG GCA GAG CCC AAC ACA TTT CAA G-3' (SEQ ID NO: 19), tRNAser pich 1, 5'-/5Biosg/CTG CAT CCT TCG CCT TAA CCA CTC GGC CAT CGT A-3' (SEQ ID NO: 20), tRNAser pich 2, 5'-/5Biosg/ACA CGA GCA GGG TTC GAA CCT GCG CGG GCA GAG C-3' (SEQ ID NO: 21) and the second blot incubated with biotinylated probes specific for tRNA$_{CUA}^{tyr}$: tRNA 5' biot, 5'-/5Biosg/GGA AGG ATT CGA ACC TTC GAA GTC GAT GAC GG-3' (SEQ ID NO: 22) and tRNA 3' biot, 5'-/5Biosg/TCT GCT CCC TTT GGC CGC TCG GGA ACC CCA CC-3' (SEQ ID NO: 23). Probes were incubated overnight at 55° C., bound to a streptavidin-horseradish peroxidase (HRP) conjugate, and detected with a luminol/enhancer—stable peroxide solution (Pierce) (FIG. 2a). Relative tRNA amounts were determined by band density. The results of FIG. 2 indicate that transcription of the tRNA$_{CUA}$ was found to be approximately 1.5 times greater in P. pastoris+pREAV-P$_{ADH1}$-pApaRS than the same cassette in S. cerevisiae by northern blot analysis (FIG. 2a).

Figure 1D:
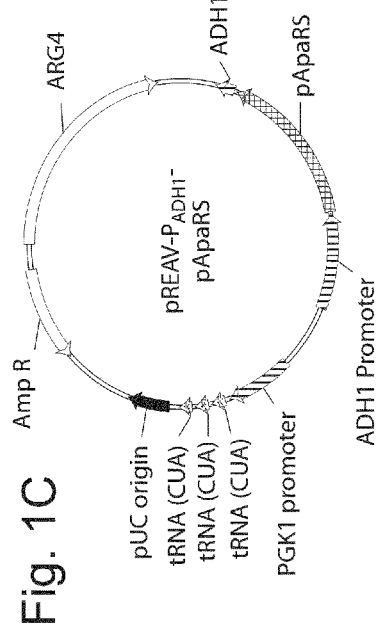
Figure 1E:

To address the poor expression of pApaRS, pREAV was modified to drive expression of pApaRS with the powerful P$_{AOX1}$ promoter, and pApaRS expression was further enhanced by adding a Kozak consensus sequence (ACCATGG) (Kozak (1990) "Downstream secondary structure facilitates recognition of initiator codons by eukaryotic ribosomes." Proc Natl Acad Sci USA 87: 8301-8305) to the 5' end of the pApaRS gene. The ADH1 terminator (T$_{ADH1}$) was also replaced by the AOX1 terminator (T$_{AOX1}$) in the final construct pREAV-P$_{AOX1}$-pApaRS (FIG. 1d). To create pREAV-P$_{AOX1}$-pApaRS, the AOX1 promoter and terminator sequences were derived from pPIC3.5k. The pApaRS was amplified with primers: KETO-Koz-F, 5'-TTC TGA GAA TTC ACC ATG GCA AGC AGT AAC TTG ATT AAA CAA TTG C-3' (SEQ ID NO: 24) and KetoRS R 6×His, 5'-TAG GCT CGG CCG CTT AGT GGT GGT GGT GGT GGT GTT TCC AGC AAA TCA GAC AGT AAT TCT TTT TAC-3' (SEQ ID NO: 25), digested with EcoRI and NotI (NEB) and ligated into the similarly digested pPIC3.5k to create pPIC3.5k-pApaRS. The P$_{AOX1}$-pApaRS-T$_{AOX1}$ coding region was amplified from pPIC3.5k-pApaRS with primers: pPIC-keto AOX5 F, 5'-ATC GTA CTT AAG AGA TCT AAC ATC CAA AGA CGA AAG GTT GAA TGA AAC-3' (SEQ ID NO: 26) and pPIC-keto AOXTT R, 5'-TGC ACA GGC GCG CCA AGC TTG CAC AAA CGA ACT TCT CAC TTA ATC TTC-3' (SEQ ID NO: 27), digested with AscI and AflII (NEB) and ligated into the similarly digested pREAV-P$_{ADH1}$-pApaRS PCR product to create pREAV-P$_{AOX1}$-pApaRS. Constructs were confirmed by size mapping and sequencing, as described above.

Figure 2B:
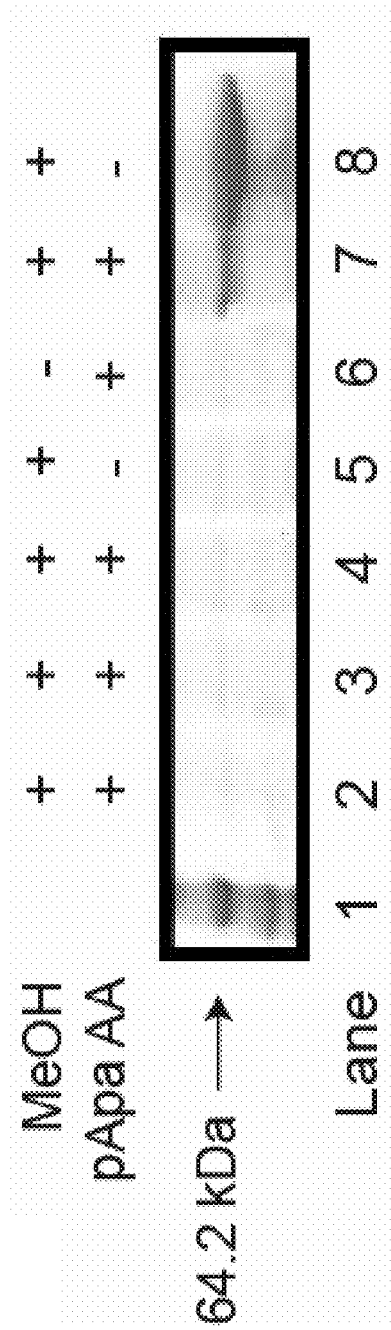
Figure 2C:
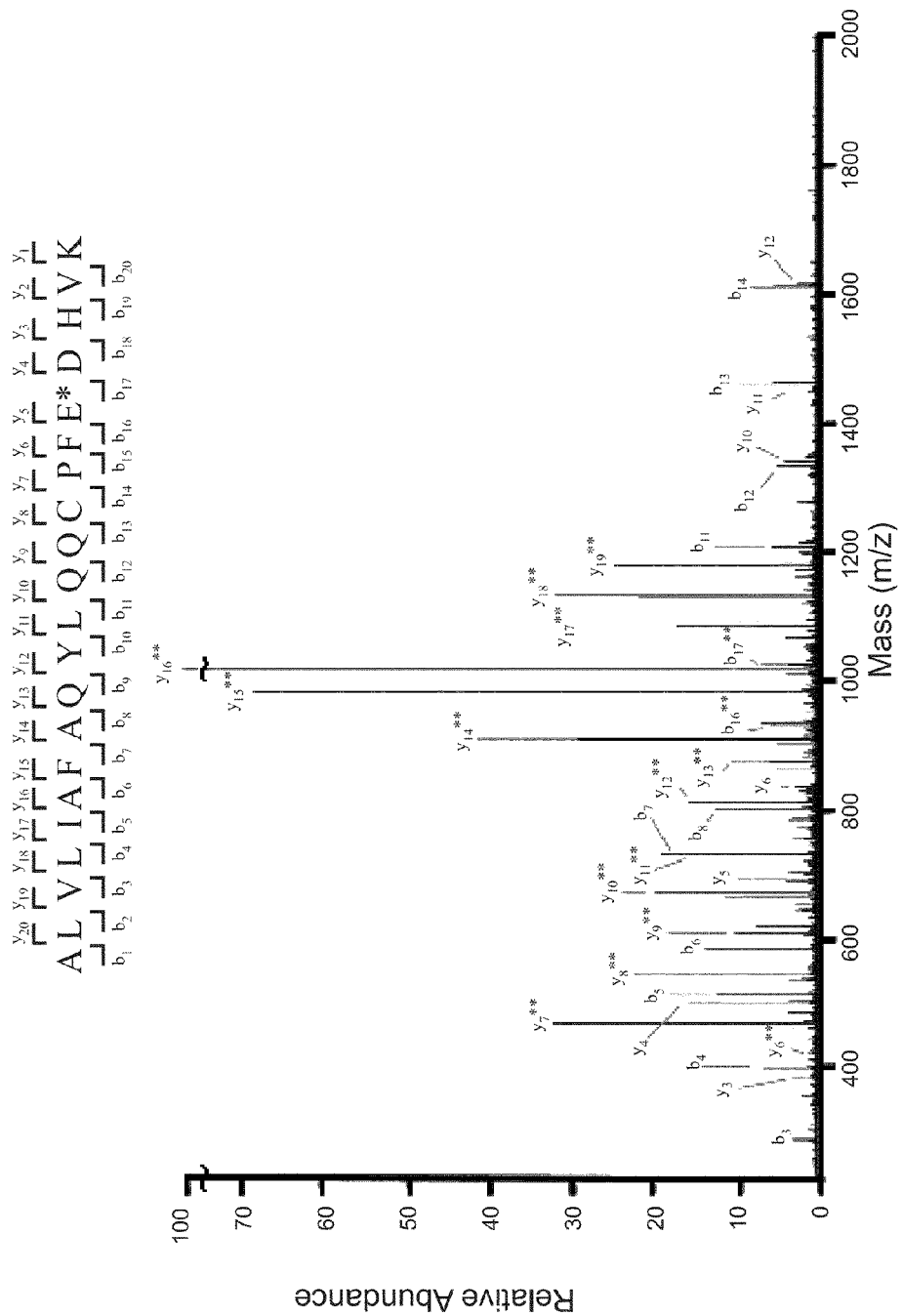

The GS200-pREAV-P$_{AOX1}$-pApaRS (his4, ARG4, Gen$^R$, mut$^s$) strain was constructed by transforming pREAV-P$_{AOX1}$-pApaRS into GS200 but plated on RDB plates supplemented with 4 mg ml$^{-1}$ histidine and not further screened for Geneticin® resistance. Transformations to create GS200-rHSA$_{E37X}$/pREAV-P$_{AOX1}$-pApaRS (HIS4, ARG4, Gen$^R$, mut$^s$) were carried out using the protocol described above with competent G3 (e.g., GS200-rHSA$_{E37X}$) except recovered cells were plated on RDB plates lacking L-histidine (His) and Arg. Clones from this transformation produced full length rHSA$_{E37pApa}$ only in the presence of methanol and pApa amino acid, at levels approximately 10-20% of identical clones harboring rHSA$_{WT}$. Protein was visible by SDS-PAGE gel two to three days post methanol induction, and peaked six days after expression with methanol supplementation to 0.5% every 24 h (FIG. 2b). Yeast lacking the pREAV cassette, pPIC3.5k cassette, methanol supplementation, or pApa amino acid failed to produce protein detectable by Coomassie staining. The lack of protein expression in the absence of pApa amino acid indicates that no cross aminoacylation occurs between the pApaRS/tRNA$_{CUA}^{tyr}$ pair and the endogenous aminoacylation machinery. Site-specific incorporation of pApa into rHSA$_{E37X}$ was confirmed by tryptic digest, LC-MS/MS (FIG. 2c). pApa (denoted E* in FIG. 2c) was incorporated at residue 37 of mature rHSA$_{E37pApa}$. The substitution is supported without ambiguity by the observed fragment ion series.

To express enough rHSA$_{E37pApa}$ protein to perform the LC-MS/MS analysis, the protein expression analysis conditions described above were modified. Briefly, 1 L of BMGY was inoculated with 20 ml of saturated G3-2 culture in YPD and grown (~24 h, 29.2° C., 300 r.p.m.) to OD$_{600}$≈12-18. The culture was centrifuged at 1500 g, and resuspended in 200 ml buffered minimal methanol (BMM) supplemented with 10% BMMY and 2 mM pApa. After 6 days of growth (29.2° C., 300 r.p.m. with methanol and volume supplementation) the culture was centrifuged at 3000 g, cells discarded, and supernatant passed through a 0.22 µm filter (Millipore, Billerica, Mass.). The supernatant was ammonium sulfate (NH$_4$SO) precipitated by addition of NH$_4$SO$_4$ with slow stirring at 4° C. to 50% of saturation (58.2 g), centrifugation at 20,000 g for 20 min, and again by addition of NH$_4$SO$_4$ to 75% of saturation (31.8 g), and centrifugation at 20,000 g for 20 min. The second precipitation contained rHSA$_{E37pApa}$ and was resuspended in FPLC Buffer A (25 mM Tris-HCl, 25 mM sodium chloride, 1 mM EDTA, 1× protease inhibitor cocktail (Roche, Basel, CH), pH=8.5). The resolubilized protein was purified with MonoQ 5/5 column (GE Healthcare) on an AKTA purifier FPLC (Amersham Biosciences, Piscataway, N.J.) (elution at 20-35% Buffer B (Buffer A+1 M NaCl)). Fractions were analyzed by SDS-PAGE gel, combined, dialyzed with a 30 MWCO dialysis cassette (Pierce) to PBS, and purified with a Superdex 200 10/300 GL (GE Healthcare) on an AKTA purifier FPLC (elution after 14 min in PBS at 0.5 ml min$^{-1}$). Fractions were analyzed by SDS-PAGE gel, combined, and purified with a C8 Vydac HPLC column (300 mm, 200 Å, 5 µm, Grace) on a Dynamax HPLC (Rainin, Oakland) (elution at 40-46% MeCN in water, 0.1% TFA). Fractions were analyzed by SDS-PAGE gel, and rHSA$_{E37pApa}$-containing fractions were flash frozen and lyophilized to a white powder. Purification of rHSA$_{WT}$ from F2-wt was done in similar fashion.

To perform the tryptic digest and nano-RP LC-MS/MS, purified rHSA$_{E37X}$ was digested overnight with trypsin under reducing conditions (10 mM TCEP, 1M guanidine HCl, 100 mM triethanolamine HCl, pH=7.8). The digest was purified by reversed-phase solid-phase extraction with a Sep-Pak, C18, (Waters, Milford, Mass.) and lyophilized. Oxidation of cysteines to cysteic acid and methionine to methionine sulfone was performed by incubation of lyophilized peptides with performic acid (9 parts concentrated formic acid+1 part 30% H$_2$O$_2$) (Matthiesen et al. (2004) "Use of performic acid oxidation to expand the mass distribution of tryptic peptides." Analytical chemistry 76, 6848-6852) for 1 h on ice. The reaction was quenched by addition of an excess of mercaptoethanol and 20× dilution with water. Nano-RP LC-MS/MS was performed with a HPLC system (Agilent Technologies, Santa Clara, Calif.) equipped with an LTQ Orbitrap hybrid mass spectrometer (ThermoElectron, Rochester, N.Y.). Tryptic digests were loaded onto the precolumn (4 cm, 100 µm i.d., 5 µm, Monitor C18, Column Engineering, Chicago, Ill.) of a vented column setup (Licklider et al. (2002) "Automation of nanoscale microcapillary liquid chromatography-tandem mass spectrometry with a vented column" Analytical chemistry 74: 3076-3083) at a flow rate of ~2 µl min$^{-1}$. After a load/wash period of 10 min gradient elution was started by switching the precolumn in line with the analytical column (10 cm, 75 µm i.d., 5 µm C18). The chromatographic profile was from 100% solvent A (0.1% aqueous acetic acid) to 50% solvent B (0.1% acetic acid in acetonitrile) in 40 min at ~100 nl min$^{-1}$. Data-dependent MS/MS acquisitions were performed following a top 10 scheme in which the mass spectrometer was programmed to first record a high-resolution Orbitrap scan (m/z 500-2,000) followed by 10 data-dependent MS/MS scans (relative collision energy=35%; 3 Da isolation window). The raw data was searched against the SwissProt 51.6 database using MASCOT (Matrixscience, London, UK) for protein identification with pApa as a variable modification.

Optimization of Expression

Figure 9:
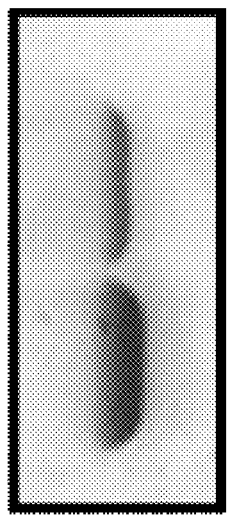
FIG. 9 depicts the results of an experiment that was performed to determine whether rHSA$_{E37X}$ is expressed more robustly in a *P. pastoris* Mut$^+$ mutant.

In an effort to optimize expression of rHSA$_{E37pApa}$, a GS200-rHSA$_{E37X}$/pREAV-P$_{AOX1}$-pApaRS (HIS4, ARG4, Gen$^R$) fast methanol utilization (Mut$^+$) mutant was created by insertion of pPIC3.5k-rHSA$_{E37X}$ into the region 5' of the AOX1 gene locus (this retains the integrity of the AOX1 gene). Genomic insertion in this manner can lead to multimerization, yielding tandem copies of both the Geneticin® resistance marker and the gene of interest (Cereghino et al. (2000) "Heterologous protein expression in the methylotrophic yeast Pichia pastoris." FEMS Microbiol Rev 24: 45-66). To create GS200-rHSA$_{E37X}$/pREAV-P$_{AOX1}$-PApaRS (HIS4, ARG4, Gen$^R$, Mut$^+$), 20 µg of pPIC3.5k-rHSA$_{E37X}$ was linearized with SacI or SalI (NEB) and transformed into freshly competent GS200 as previously described. Cells were recovered in 1 ml of cold 1 M sorbitol, and plated on RDB plates supplemented with 0.4 mg ml$^{-1}$ arginine. Colonies were picked into a 2 ml 96 well block with 1 ml YPD, grown to saturation (29.2° C., 300 r.p.m.), diluted 1:100, and replica plated on plates containing 0 to 3.0 mg ml$^{-1}$ Geneticin®. Clone 1D12 which survived up to 1.0 mg ml$^{-1}$ Geneticin®, was made competent, transformed with pREAV-P$_{AOX1}$-pApaRS as previously described and plated on RDB plates lacking Arg and His. Colonies were picked into a 1 ml 96 well block, grown to saturation, diluted 1:100, and rescreened on Geneticin® 1.0 mg ml$^{-1}$ plates. 14 surviving clones were picked, and tested for rHSA$_{E37pApa}$ expression in the presence of pApa amino acid and methanol. The mut$^s$ protocol was used, as described above. Clone K5 showed greatest protein expression, and was compared to G3-2 in test expressions (FIG. 9). 25 µl of cleared media from a GS200-rHSA$_{E37X}$/pREAV-P$_{AOX1}$-pApaRS (mut$^+$) culture (FIG. 9, lane 1) and a GS200-rHSA$_{E37X}$/pREAV-P$_{AOX1}$-pApaRS (mut$^s$) culture (FIG. 9, lane 2) were analyzed on an SDS-PAGE gel and stained with Coomassie. The resulting clone K5 displayed resistance to Geneticin® up to 1 mg ml⁻¹; whereas the aforementioned mut$^s$ clone G3-2 died above 0.25 mg ml⁻¹ Geneticin®, consistent with the incorporation of multiple copies of the cassette (Cereghino et al. (2000) "Heterologous protein expression in the methylotrophic yeast *Pichia pastoris*." *FEMS Microbiol Rev* 24: 45-66; Invitrogen Life Technologies, Carlsbad, Calif. 92008; 2005). Analysis of full length rHSA$_{E37pApa}$ expression from isolated clones in the presence of methanol and pApa amino acid showed that approximately 1.5-2.0 times more protein was produced than with the mut$^s$ counterpart (FIG. 9). Relative amounts of protein determined by band density.

To further increase yields of rHSA$_{E37pApa}$ six different promoters (including P$_{AOX1}$) were compared for their ability to drive pApaRS transcription in the pREAV vector. Transcript mRNA levels, pApaRS protein levels, and overall rHSA$_{E37pApa}$ yields were assayed. Two constitutive promoters derived from yeast, GTP binding protein I (YPT1) (Sears et al. (1998) "A versatile set of vectors for constitutive and regulated gene expression in *Pichia pastoris*." *Yeast* 14: 783-790; Segev et al. (1988) "The yeast GTP-binding YPT1 protein and a mammalian counterpart are associated with the secretion machinery." *Cell* 52: 915-924); glyceraldehyde-3-phosphate dehydrogenase (GAP) (Cos et al. (2006) "Operational strategies, monitoring and control of heterologous protein production in the methylotrophic yeast *Pichia pastoris* under different promoters: a review." *Microb Cell Fact* 5: 17; Waterham et al. (1997) "Isolation of the *Pichia pastoris* glyceraldehyde-3-phosphate dehydrogenase gene and regulation and use of its promoter." *Gene* 186: 37-44); three methanol inducible promoters from alcohol oxidase II (AOX2) (Ohi et al. (1994) "The positive and negative cis-acting elements for methanol regulation in the *Pichia pastoris* AOX2 gene." *Mol Gen Genet.* 243: 489-499), formaldehyde dehydrogenase I (FLD1) (Cos et al. (2006) "Operational strategies, monitoring and control of heterologous protein production in the methylotrophic yeast *Pichia pastoris* under different promoters: a review." *Microb Cell Fact* 5: 17); and isocitrate lyase I (ICL1) (Cos et al. (2006) "Operational strategies, monitoring and control of heterologous protein production in the methylotrophic yeast *Pichia pastoris* under different promoters: a review." *Microb Cell Fact* 5: 17) were chosen based on their compatibility with methanol induction. A truncated version of P$_{AOX2}$ was used which enhances the promoter by deleting one of the two repressor binding sequences (Ohi et al. (1994) "The positive and negative cis-acting elements for methanol regulation in the *Pichia pastoris* AOX2 gene." *Mol Gen Genet.* 243: 489-499). The use of the somewhat weaker P$_{YPT1}$ and P$_{GAP}$ promoters (Sears et al. (1998) "A versatile set of vectors for constitutive and regulated gene expression in *Pichia pastoris*." *Yeast* 14: 783-790) could be useful in the event that overproduction of the synthetase is toxic to the yeast, or sequesters cellular energy away from production of rHSA$_{E37X}$.

Figure 10:
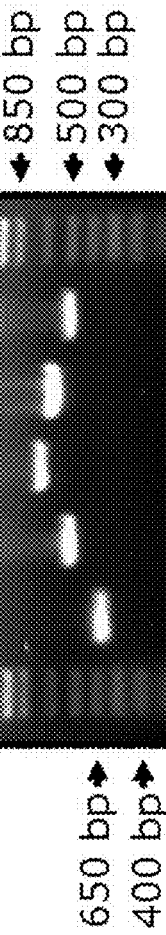
FIG. 10 depicts the results of PCR that was performed to amplify various *P. pastoris* gene promoters.

All promoters were amplified by PCR from *P. pastoris* genomic DNA along with their 5' untranslated regions (FIG. 10). P$_{AOX2}$, P$_{YPT1}$, P$_{ICL1}$, P$_{FLD1}$, and P$_{GAP}$ were separately amplified by PCR from genomic DNA (*P. pastoris* GS200) using the following primers: PAOX2 F, 5'-GTA TCG CTT AAG TCC AAG ATA GGC TAT TTT TGT CGC ATA AAT TTT TGT C-3' (SEQ ID NO: 28) and PAOX2 R, 5'-CGT TAG CCA TGG TTT TCT CAG TTG ATT TGT TTG TGG GGA TTT AGT AAG TCG-3' (SEQ ID NO: 29); PYPT1 F, 5'-GTA TCG CTT AAG CAT ATG ATG AGT CAC AAT CTG CTT CCA CAG ACG AG-3' (SEQ ID NO: 30) and PYPT1 R, 5'-CGT TAG CCA TGG GAC TGC TAT TAT CTC TGT GTG TAT GTG TGT ATT GGG C-3' (SEQ ID NO: 31); PICL1 F, 5'-GTA TCG CTT AAG GAA TTC GGA CAA ATG TGC TGT TCC GGT AGC TTG-3' (SEQ ID NO: 32) and PICL1 R, 5'-CGT TAG CCA TGG TCT TGA TAT ACT TGA TAC TGT GTT CTT TGA ATT GAA AG-3' (SEQ ID NO: 33); PFLD1 F, 5'-GTA TCG CTT AAG GCA TGC AGG AAT CTC TGG CAC GGT GCT AAT GG-3' (SEQ ID NO: 34) and PFLD1 R, 5'-CGT TAG CCA TGG TGT GAA TAT CAA GAA TTG TAT GAA CAA GCA AAG TTG G-3' (SEQ ID NO: 35); PGAP1 F, 5'-GTA TCG CTT AAG GGA TCC TTT TTT GTA GAA ATG TCT TGG TGT CCT CGT C-3' (SEQ ID NO: 36) and PGAP1 R, 5'-CGT TAG CCA TGG TGT GTT TTG ATA GTT GTT CAA TTG ATT GAA ATA GGG AC-3' (SEQ ID NO: 37); respectively. FIG. 10 shows an ethidium bromide stained gel with a 1 kb+ ladder flanking the PCR products. The expected lengths of the PCR products are PAOX2 342 bp, PYPT1 508 bp, PICL1 683 bp, PFLD1 597 bp, and PGAP 493 bp. The PCR amplified fragments were digested with AflIII and NcoI (NEB) and ligated into the similarly digested pREAV-P$_{AOX1}$-pApaRS (after removal of the P$_{AOX2}$ coding region via agarose gel purification) to create the pREAV-P$_{Promoter}$-pApaRS.

Figure 4:
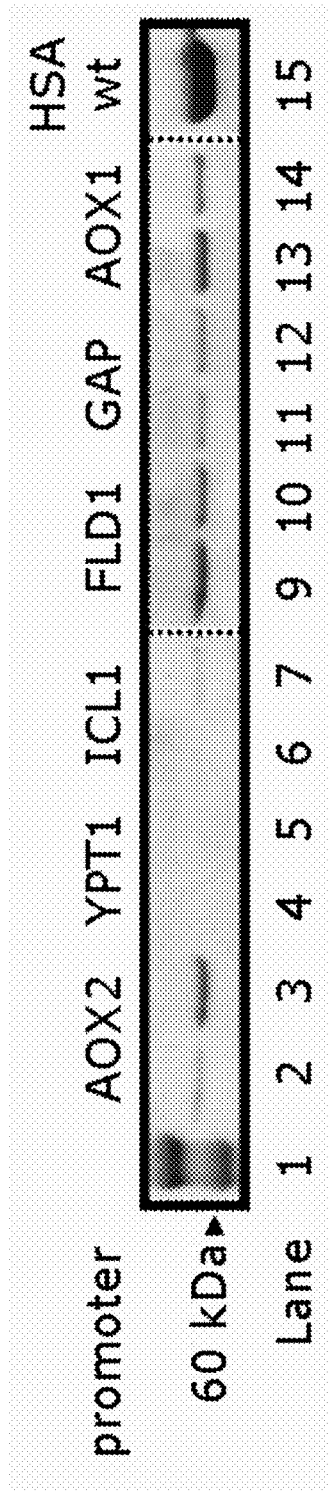
FIG. 4 shows the results of experiments that were performed to determine amber suppression levels with $P_{AOX2}$, $P_{YPT1}$, $P_{ICL1}$, $P_{FLD1}$, $P_{GAP}$, or $P_{AOX1}$ driven aaRS, as assayed by rHSA$_{E37pApa}$ levels in the media.

After sequence confirmation, each promoter was cloned into the pREAV vector 5' of pApaRS in place of P$_{AOX1}$, and transformed into the Mut⁺ GS200-HSA$_{E37X}$ created previously. The terminator remained T$_{AOX1}$. FIG. 3a provides a linear map of pREAV-P$_{Promoter}$-pApaRS illustrating the promoter region being varied. Promoters were PCR amplified from genomic DNA (as in the experiments whose results are depicted in FIG. 7). The plasmids (like the previously described construct pREAV-P$_{AOX1}$-pApaRS) were linearized with AatII, transformed into freshly competent GS200-rHSA$_{E37X}$ (clone 1D12), and plated on RDB plates lacking Arg and His as previously described to create GS200-rHSA$_{E37X}$/pREAV-P$_{Promoter}$-pApaRS (HIS4, ARG4, Gen$^R$, Mut⁺). Surviving clones were screened for Geneticin® resistance at 0.75 and 1.0 mg ml⁻¹. 48 clones corresponding to each promoter were picked into 1 mL 96 well blocks containing BMGY and grown to saturation (29.2° C., 24 h, 300 r.p.m.). The saturated cultures were centrifuged at 1500 g for 10 min and cells were resuspended in 200 µL BMMY+2 mM pApa amino acid. After 6 days (29.2° C., 300 r.p.m., with supplementation), the media was cleared by centrifugation at 3000 g for 10 minutes, and 1-2 µL of the cleared media spotted on a 0.45 micron nitrocellulose membrane (Bio-Rad) using a 96 well pin tool. The membrane was probed with the HSA antibody [1A9] HRP conjugate (Abcam) using standard western blotting techniques (Burnette (1981) "Western blotting: electrophoretic transfer of proteins from sodium dodecyl sulfate—polyacrylamide gels to unmodified nitrocellulose and radiographic detection with antibody and radioiodinated protein A." *Anal Biochem* 112: 195-203), and detected with ECL HRP chemiluminescence detection reagents and protocols (GE Healthcare). The two highest expressing clones corresponding to each promoter (AOX2: A6 and B7; YPT1: D11 and B7; ICL1: E5, and H3; FLD1: E11 and F3; GAP: B7 and B10; and AOX1: E3 and E7) were chosen for parallel test expressions (FIGS. 3 and 4).

P-$_{Promoter}$-pApaRS expression levels were monitored by northern and western blots after 6 days of methanol induction and compared to P$_{AOX1}$-pApaRS (FIG. 3b). Due to inherent expression variability with *P. pastoris*, two clones were chosen for western blot analysis. The two clones from each transformation of GS200-rHSA$_{E37X}$ with pREAV-P$_{Promoter}$-pApaRS were grown with methanol as the primary carbon source for 6 days, lysed, separated on an SDS-PAGE gel (FIG. 3b, top gel). The gel was stained with Coomassie to verify equal loading. Lysates were analyzed via western blot for pApaRs-His$_{6x}$ (FIG. 3b, bottom gel).

To perform western blots, clones, AOX2: A6 and B7; YPT1: D11 and B7; ICL1: E5 and H3; FLD1: E11 and F3; GAP: B7 and B10; and AOX1: E3 and E7 were cultured under test expression conditions, pelletted (3000 g, 10 min), and lysed with 2 ml YeastBuster (Novagen, Gibbstown, N.J.)+10 mM β-mercaptoethanol and Complete Protease Inhibitor Cocktail tablets (Roche). Samples were cleared at 20,000 g and 15 µl of the lysate run on a 4-20% SDS-PAGE gel (1:15 h, 150 V). The protein was transferred to a 0.45 micron nitrocellulose membrane (Bio-Rad) using a Trans-Blot SD semi-dry transfer cell (Bio-Rad) in Tobin's transfer buffer (24 mM tris base, 192 mM glycine, 20% ethanol) (2 h, 20 V, 100 mAmp). Residual protein on gel was stained with Coomassie (FIG. 3b, top) to ensure equal loading. The membrane was blotted using standard western blotting techniques (Burnette (1981) "Western blotting: electrophoretic transfer of proteins from sodium dodecyl sulfate-polyacrylamide gels to unmodified nitrocellulose and radiographic detection with antibody and radioiodinated Protein A." *Anal Biochem* 112: 195-203) with an anti His$_{6x}$-HRP conjugated antibody (Sigma-Aldrich) and detected with ECL (GE Healthcare) HRP chemiluminescence detection reagents and protocols (FIG. 3b, bottom). Relative expression rates were determined by band density.

Figure 11:
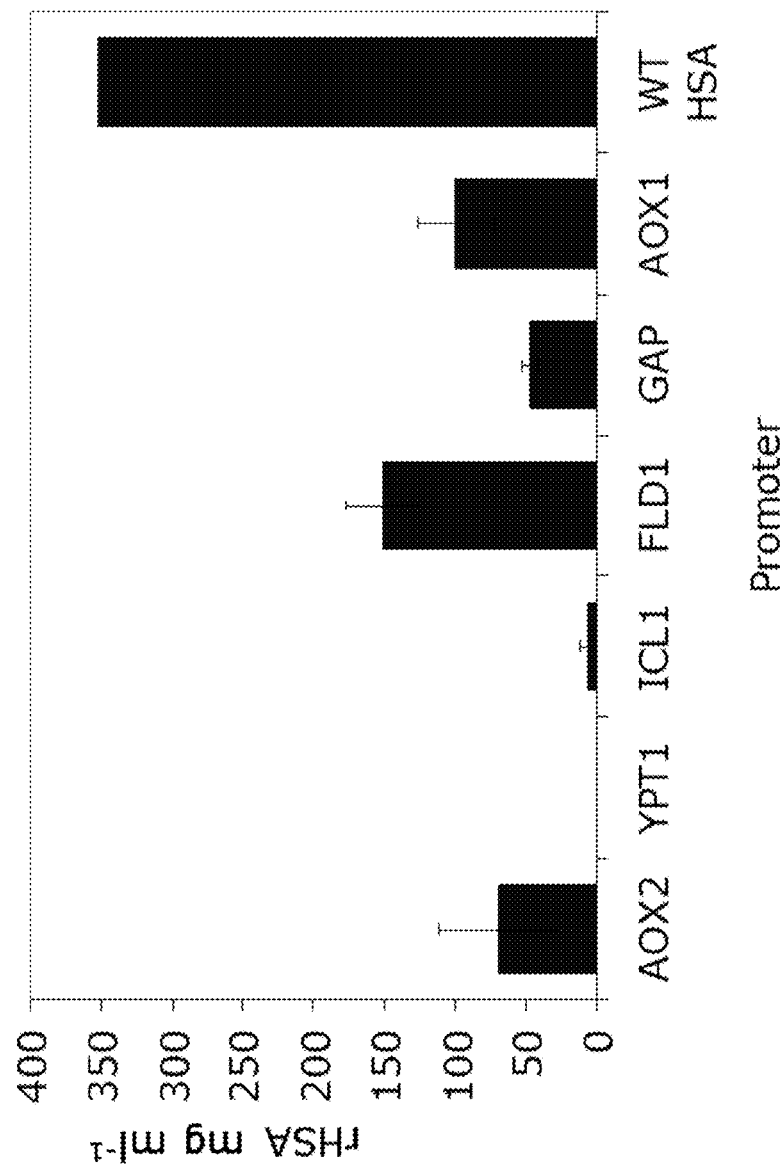
FIG. 11 provides a bar graph representation of the results of FIG. 4 showing amber suppression in rHSA$_{E37pApa}$ as a function of the promoter driving pApaRS production.
Figure 12:
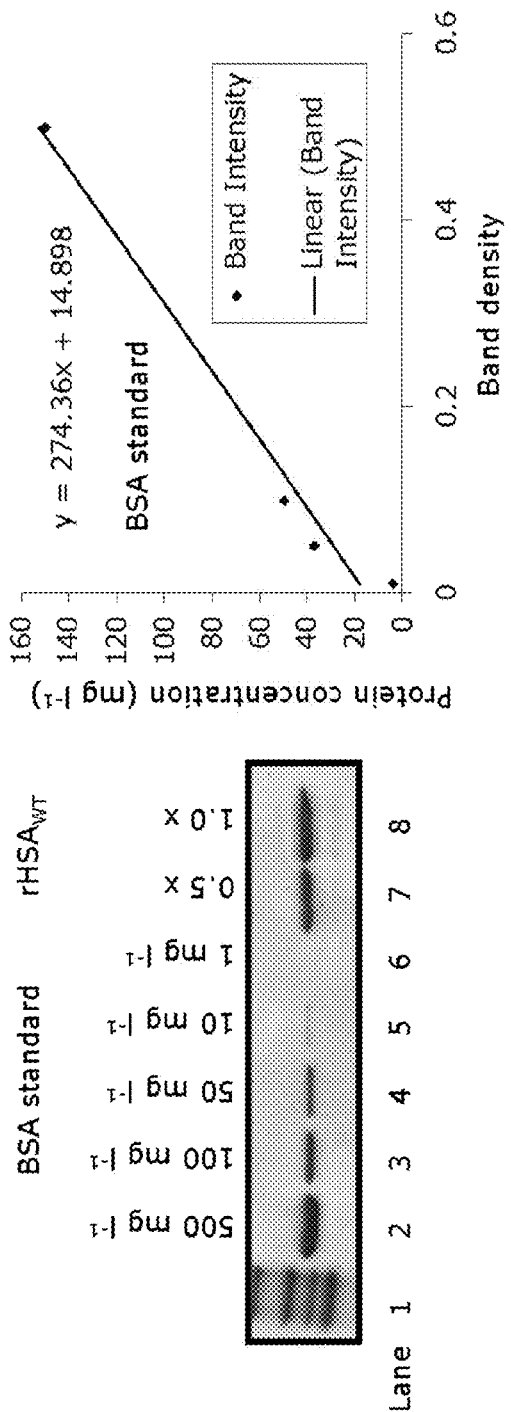
FIG. 12 shows a protein gel on which 25 µl of BSA standards or unpurified rHSA$_{WT}$ media from test protein expressions were run.

$P_{FLD1}$ drove pApaRS transcription four-fold better than $P_{AOX1}$ at the mRNA level, and produced five-fold more pApaRS protein. $P_{GAP}$, $P_{YPT1}$, $P_{ICL1}$, and $P_{AOX2}$ all showed lower pApaRS expression than $P_{FLD1}$. Consistent with this result, the overall amber suppression was highest with $P_{FLD1}$-pApa as measured by rHSA$_{E37pApa}$ expression into the media (FIG. 4). As shown in FIG. 4, the two clones from each promoter system were independently grown for six days with methanol as the primary carbon source and pApa amino acid. 25 µl of the cleared media was run on a denaturing SDS-PAGE gel and stained with Coomassie. rHSA$_{WT}$ (lane 15) was calculated to be 351.6 mg l$^{-1}$ by band density with BSA control. By density, $P_{FLD1}$ (lanes 9 and 10 averaged) expressed 43% as much protein, or 151.2 mg l$^{-1}$. Maximum yields were >150 mg L$^{-1}$ or approximately 43% of rHSA$_{WT}$ yields (352 mg L$^{-1}$) (FIG. 11). FIG. 11 provides a bar graph representation of FIG. 4 showing amber suppression in rHSA$_{E37pApa}$ as a function of the promoter driving pApaRS production. Protein production was determined by Coomassie band density on the SDS-PAGE gel shown in FIG. 4. rHSA$_{WT}$ protein in FIG. 4 was quantified as described as follows: 25 µl of BSA standards or unpurified rHSA$_{WT}$ media from test protein expressions was run on an SDS-PAGE gel (see In FIG. 12). Lane 7 was a 1:1 dilution of the rHSA$_{WT}$ test protein expression media. BSA standard band densities (lanes 2-5) were plotted, and linearly fit. The densities for rHSA$_{WT}$ bands (2× lane 7 and lane 8) average to 83.33 or, 351.55 mg ml$^{-1}$. Yields of unnatural protein (rHSA$_{E37X}$ in other figures) were determined as a percentage of the same rHSA$_{WT}$ sample.

The clones which produced most protein in FIG. 3b were analyzed by northern blot for pApaRS mRNA transcription (FIG. 3c bottom gel). To perform the northern blots, top expressing clones AOX2, B7; YPT1, D11; ICL1, H3; FLD1, E11; GAP, B7; and AOX1, E3, were grown under test expression conditions for 6 days. 3×10$^8$ cells (2.5 ml at OD$_{600}$=1.0) were collected and total RNA isolated via the RiboPure—Yeast Kit (Ambion) reagents and protocols. 13 µg of each RNA sample was loaded onto a 2% formaldehyde gel (2% agarose, 20 mM MOPS, 8 mM sodium acetate, 2.2 mM formaldehyde, pH=7.0). 3 volumes of NorthernMax formaldehyde load dye (Ambion) was mixed with 1 volume of RNA, heated to 65° C. for 15 minutes, and chilled on ice for 5 minutes before loading. The gel was electrophoresed (50 V for 2 h), and equal loading and RNA integrity were confirmed via ethidium bromide straining of 18S and 28S rRNA (FIG. 3c, top). The RNA was drawn onto a Biodyne B nylon membrane (Pall Life Science) in 10×SSC buffer (1.5 M sodium chloride, 0.15 M sodium citrate pH=7.0) via a standard blotting apparatus. The membrane was rinsed in 2×SSC buffer, dried, and auto-crosslinked with a UV Stratalinker 2400 (Stratagene). Hybridization and detection was carried out via protocols and reagents from the North2South Chemiluminescent Hybridization and Detection Kit (Pierce). Briefly, 400-500 µg of biotinylated probes: ketoRS3 biot 5'-/5Biosg/TGA GAC GCT GCT TAA CCG CTT C-3' (SEQ ID NO: 38) and ketoRS4 biot 5'-/5Biosg/TAA AGA AGT ATT CAG GAT CGG ACT G-3' (SEQ ID NO: 39) were incubated overnight at 55° C., bound to a streptavidin-HRP conjugate, and detected with a luminol/enhancer—stable peroxide solution (Pierce) (FIG. 3c, bottom). Relative mRNA titers were determined by band density.

Oxime Ligation to rHSA$_{E37pApa}$

Figure 5:
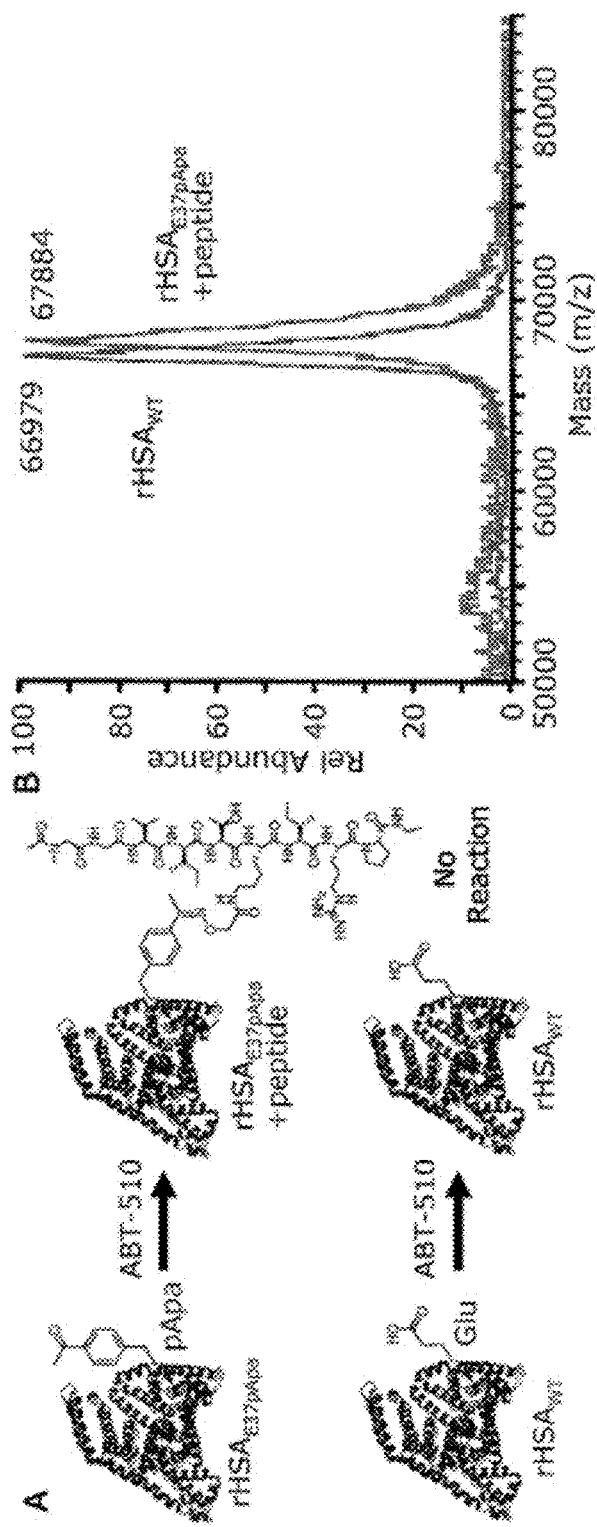
FIG. 5*a* shows a schematic of oxime ligation of ABT-510 peptide to rHSA$_{E37pApa}$. Incubation of 75 µM rHSA$_{E37pApa}$ (top) with 2.25 mM peptide overnight at 37° C. results in the formation of an oxime linkage (top right). No reaction occurs with rHSA$_{WT}$ (bottom) under identical conditions.
FIG. 5*b* shows the results of MALDI mass spectrometry that was performed to determine the extent of conjugation. Incubation of peptide with keto-containing rHS$_{AE37pApa}$ results in a 905 Da mass shift compared with incubation with rHSA$_{WT}$, indicating approximately 77% of rHSA$_{E37pApa}$ is linked to ABT-510.

To demonstrate the utility of this modified rHSA as a carrier for bioactive peptides, an oxime ligation was carried out between the unique keto side chain of rHSA$_{E37pApa}$ and the anti-angiogenic peptide ABT-510 (FIG. 5). A schematic representation of this ligation reaction is provided in FIG. 5a. The ABT-510 peptide harbors an ε-(2-(aminooxy)acetyl)-L-lysine as the sixth residue. Incubation of 75 µM rHSA$_{E37pApa}$ (FIG. 5a, top reaction) with 2.25 mM peptide overnight at 37° C., as described in further detail below, results in the formation of an oxime linkage. No reaction occurs with rHSA$_{WT}$ (FIG. 5a, bottom reaction) under identical conditions. This thrombospondin-1 (TSP-1) properdin type 1 repeat mimetic exhibits potent anti-tumor activity in humans, but suffers from rapid clearance by the kidneys when administered intravenously (Hoekstra et al. (2005) "Phase I safety, pharmacokinetic, and pharmacodynamic study of the thrombospondin-1-mimetic angiogenesis inhibitor ABT-510 in patients with advanced cancer." *J Clin Oncol* 23: 5188-5197; Yang et al. (2007) "Thrombospondin-1 peptide ABT-510 combined with valproic acid is an effective anti-angiogenesis strategy in neuroblastoma." *Cancer Res* 67: 1716-1724; Reiher et al. (2002) "Inhibition of tumor growth by systemic treatment with thrombospondin-1 peptide mimetics." *Int J Cancer* 98: 682-689). A nine amino acid peptide mimetic was synthesized with a unique ε-(2-(aminooxy)acetyl)-L-lysine UAA in place of the sixth L-norvaline residue (Anaspec, San Jose, Calif.). The sequence of the peptide was: Ac-Sar-Gly-Val-D-aloIle-Thr-Lys(Aoa)-Ile-Arg-Pro-NEt MW=1097.3 Da). Based on the known structure-activity relationships of TSP-1, modifications at this position are not expected to significantly alter biological activity (Haviv et al. (2005) "Thrombospondin-1 mimetic peptide inhibitors of angiogenesis and tumor growth: design, synthesis, and optimization of pharmacokinetics and biological activities." *J Med Chem* 48: 2838-2846). To perform the oxime ligation, 2.25 mM (0.5 mg) of the peptide was added to 75 µM rHSA$_{E37pApa}$ or rHSA$_{WT}$ (1.0 mg) in 200 µl oxime ligation buffer (1.5 M sodium chloride, 500 mM sodium acetate, pH=4.4) and incubated overnight at 37° C. At pH<5 the aminooxy group undergoes a selective oxime ligation with the keto group of pApa to covalently link the ABT-510 peptide to residue 37 of rHSA$_{E37pApa}$ (FIG. 5a, top reaction). The reactions were purified with a C8 Vydac HPLC column (300 mm, 200 Å, 5 µm, Grace) on a Dynamax HPLC (Rainin) (elution 40-46% acetonitrile in water, 0.1%). Fractions were collected, combined, and analyzed via Coomassie stained SDS-PAGE gel. Intact protein mass measurements were performed and the extent of derivatization of rHSA$_{E37pApa}$ with the peptide was confirmed using a linear MALDI-TOF MS Biflex III (Burker Daltonics, Billerica, Mass.) instrument with a sinapinic acid matrix to perform matrix assisted laser desorption ionization (MALDI) mass spectrometry (FIG. 5b). The mass of rHSA$_{WT}$ changed negligibly before and after treatment with the protein, indicating that no conjugation was observed by MALDI mass spectrometry when rHSA$_{WT}$ (glutamic acid at residue 37) was treated with the amino-oxy modified ABT-510 peptide under identical conditions.

The mass difference between rHSA$_{WT}$+peptide and rHSA$_{E37pApa}$+peptide, less 60 Da owing to the E37pApa mutation (905 Da less 60 Da=845 Da), was used to determine ligation efficiency (~77%). Previous conjugation protocols used an aniline catalyst for efficient ligation (Dirksen et al. (2006) "Nucleophilic catalysis of oxime ligation." Angew Chem Int Ed Engl 45: 7581-7584; Dirksen et al. (2006) "Nucleophilic catalysis of hydrazone formation and transimination: implications for dynamic covalent chemistry." J Am Chem Soc 128: 15602-15603); however, oxime couplings to rHSA$_{E37pApa}$ proceeded in approximately 77% yield without the use of aniline in an overnight reaction using 75 µM rHSA$_{E37pApa}$ and a thirty-fold excess of the peptide.

Addition of 8 UAAs to the Genetic Repertoire

Figure 6:
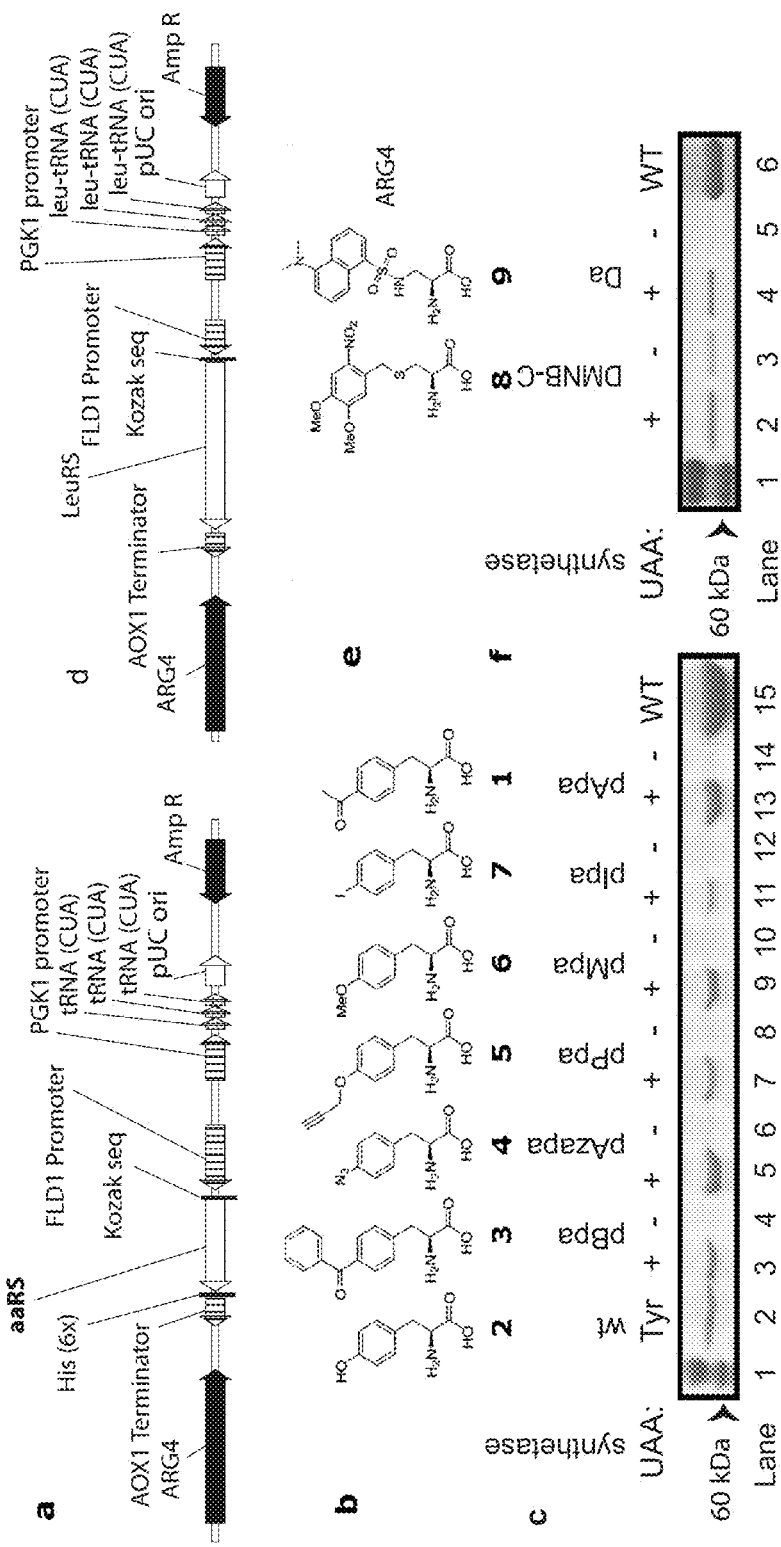
FIG. 6 depicts experiments performed to illustrate that the orthogonal translation system of the invention can be used to incorporate unnatural amino acids other than pApa (e.g., Structures 3-9) into rHSA$_{E37X}$ in *P. pastoris*. (a) Schematic of the optimized pREAV-$P_{FLD1}$ vector with *E. coli* tyrosyl-RS gene and tyrosyl suppressor tRNA cassette (tRNA$_{CUA}$). (b) Structures of six unnatural amino acids (Structures 1, 3-7) and tyrosine (Structure 2) with specific *E. coli* tyrosyl-RS. (c) Expression of rHSA$_{E37X}$ (where X is defined as the unnatural amino acid) in the presence (+) and absence (−) of unnatural amino acids Structures 1 and 3-7 with their corresponding aaRS. Twenty-five microliters of unpurified cleared media was run on a SDS-PAGE gel and stained with Coomassie. Lane 2 is rHSA$_{E37Y}$ expression with the wild-type (wt) tyrosyl-RS. Lane 15 is expression of rHSA$_{WT}$. (d) Schematic of the optimized pREAV$_{leu}$-$P_{FLD1}$ vector with *E. coli* leucyl-RS gene (LeuRS) and leucyl suppressor tRNA cassette (LeutRNA$_{CUA}$). (e) Structure of the DMNB-C and dansyl unnatural amino acids (8, 9) with specific *E. coli* leucyl aaRSs. (f) Expression of rHSA$_{E37X}$ in the presence (+) and absence (−) of unnatural amino acids, 8 and 9, with their corresponding LeuRS. Twenty-five microliters of unpurified cleared media from each protein expression was analyzed on an SDS-PAGE gel and stained with Coomassie. Lane 4 is expression of rHSA$_{WT}$, also after three days.

To illustrate the generality of this newly created recombinant expression system, unnatural aaRSs evolved by the S. cerevisiae methodology were inserted into pREAV-P$_{FLD1}$. FIG. 6a provides a schematic of the optimized pREAV-$_{PFLD1}$ vector with E. coli tyrosyl-RS gene (aaRS) and tyrosyl suppressor tRNA cassette (tRNA$_{CUA}$). The aaRSs specific for p-benzoylphenylalanine (pBpa, photocrosslinker, FIG. 6b, Structure 3, Chin et al. (2003) "An expanded eukaryotic genetic code." Science 301: 964-967); p-azidophenylalanine (pAzapa, photocrosslinker, chemically reactive, FIG. 6b, Structure 4, Deiters et al. (2003) "Adding amino acids with novel reactivity to the genetic code of Saccharomyces cerevisiae." J Am Chem Soc 125: 11782-11783); p-(propargyloxy) phenylalanine (pPpa, chemically reactive, FIG. 6b, Structure 5, Deiters et al. (2003) "Adding amino acids with novel reactivity to the genetic code of Saccharomyces cerevisiae." J Am Chem Soc 125: 11782-11783); p-methoxyphenylalanine (pMpa, structure/function probe, FIG. 6b, Structure 6, Chin et al. (2003) "An expanded eukaryotic genetic code." Science 301: 964-967); and p-iodophenylalanine (pIpa, heavy atom, FIG. 6b, Structure 7, Chin et al. (2003) "An expanded eukaryotic genetic code." Science 301: 964-967) were all inserted behind P$_{FLD1}$ in the optimized pREAV-P$_{FLD1}$ vector (FIGS. 6a and 6b). For comparison, wild type E. coli tyrosyl-RS (wt, FIG. 6b, Structure 2) was also inserted into the new expression vector. Unnatural aaRSs specific for tyrosine (wt), pBpa, pAzapa, pPpa, pMpa, and pIpa were amplified by PCR using the primers: KETO-Koz-F and KetoRS R 6×His (described above), digested with NcoI and EagI (NEB) and ligated into the similarly digested pREAV-P$_{FLD1}$-pApaRS (after removal of the pApaRS region via agarose gel purification). After sequence confirmation, the plasmids were transformed into GS200-rHSA$_{E37X}$ clone 1D12 as previously described to create GS200-rHSA$_{E37X}$/pREAV-P$_{FLD1}$-(synthetase$_{tyr}$) (HIS4, ARG4, Gen$^R$, Mut$^+$). 12 clones were chosen from each transformation and screened via dot blot in 96 well format as previously described. The best producer was chosen from each (tyr, A9; pBpa, B7; pAzapa C9; pPpa, D6; pMpa, E6; and pIpa, F6) and compared to FLD1 (i.e., the strain harboring pREAV-P$_{FLD1}$-pApaRS) E11 in rHSA expression experiments, as described above, to determine their abilities to suppress the amber mutation at position 37 in rHSA$_{E37X}$, where X is defined as the unnatural amino acid) in the presence (+) and absence (−) of unnatural amino acids 1, 3-7 with their corresponding aaRS. The results of these experiments are depicted in FIG. 6c. 25 µl of unpurified cleared media was run on a SDS-PAGE gel and stained with Coomassie. Lane 2 is rHSA$_{E37Y}$ expression with the wild type (wt) tyrosyl-RS. Lane 15 is expression of rHSA$_{WT}$. Suppression yields were similar for the pApa and pAzapa mutants (40-45% the yield of rHSA$_{WT}$); all other mutants with the exception of pIpa expressed >20% the yield of rHSA$_{WT}$ (FIG. 6c). Relative protein yields were determined by band density. No protein expression was observed in the absence of the cognate amino acid, demonstrating the high orthogonality of this new system Recently, a second orthogonal E. coli leucyl-derived RS/tRNA$_{CUA}$ pair (aaRS denoted as LeuRS) was generated to incorporate additional unnatural amino acids into proteins in S. cerevisiae (Lemke et al. (2007) "Control of protein phosphorylation with a genetically encoded photocaged amino acid." Nat Chem Biol 3: 769-772; Summerer et al. (2006) "A genetically encoded fluorescent amino acid." Proc Natl Acad Sci USA 103: 9785-9789). To accommodate unnatural LeuRSs derived from this orthogonal pair in the new P. pastoris expression system, the tRNA region of pREAV-P$_{FLD1}$ plasmid was modified. The existing tRNA$_{CUA}^{Tyr}$ cassette downstream of P$_{PGK1}$ was excised and replaced by a coding region corresponding to three tandem repeats of tRNA$_{CUA}^{Leu5}$ lacking the 5' CCA and separated by SUP4 segments, as previously described, to create pREAV$_{leu}$-P$_{FLD1}$. LeuRS mutants specific for 4,5-dimethoxy-2-nitrobenzylserine (DMNB-S, photocaged serine, FIG. 6e, Structure 8, Lemke et al. (2007) "Control of protein phosphorylation with a genetically encoded photocaged amino acid." Nat Chem Biol 3: 769-772) and 2-amino-3-(5-(dimethylamino)naphthalene-1sulfonamide)propanoic acid (dansylalanine, dansyl fluorophore, FIG. 6e, Structure 9, Summerer et al. (2006) "A genetically encoded fluorescent amino acid." Proc Natl Acad Sci USA 103: 9785-9789) were inserted behind P$_{FLD1}$ to create pREAV$_{leu}$-P$_{FLD1}$-LeuRS (FIGS. 6d and 6f).

FIG. 6d provides a schematic of the optimized pREAV$_{leu}$-P$_{FLD1}$ vector with E. coli leucyl-RS gene and leucyl suppressor tRNA cassette (leu-tRNA (CUA). To create pREAV$_{leu}$-P$_{FLD1}$ a section corresponding to three tandem repeats of tRNA$_{CUA}^{Leu5}$ lacking the 5' CCA and separated by SUP4 segments was synthesized (DNA 2.0, Menlo Park, Calif.) and PCR amplified using primers: Leu tRNA F, 5'-AAG GAA GCT AGC CTC TTT TTC AAT TGT ATA TGT G-3' (SEQ ID NO: 40) and Leu tRNA R, 5'-CGT ACA CGC GTC TGT ACA GAA AAA AAA GAA AAA TTT G-3' (SEQ ID NO: 41). The resulting 643 base pair product was digested with NheI and MiuI (NEB) and ligated into the similarly digested pREAV-P$_{FLD1}$-pApaRS (after removal of the tyrosyl tRNA via agarose gel purification), to create pREAV$_{leu}$-P$_{FLD1}$-pApaRS. aaRSs with specificity for the DMNB-S and dansyl unnatural amino acids were amplified using primers: LeuRS F, 5'-ATT CAC ACC ATG GAA GAG CAA TAC CGC CCG GAA GAG-3' (SEQ ID NO: 42) and LeuRS R, 5'-TTA ATT CGC GGC CGC TTA GCC AAC GAC CAG ATT GAG GAG TTT ACC TG-3' (SEQ ID NO: 43), digested with NcoI and NotI (NEB), and ligated into the similarly digested pREAV$_{leu}$-P$_{FLD1}$-pApaRS (after removal of the pApaRS coding region via agarose gel purification) to create pREAV$_{leu}$-P$_{FLD1}$-DMNB-S or pREAV$_{leu}$-P$_{FLD1}$-dansyl (FIG. 6d). After sequence confirmation, the plasmids were transformed into GS200-rHSA$_{E37X}$ (clone 1D12) and screened in 96 well dot blot format as described. Clones A:A5 (DMNB-S) and B:G12 (dansyl) were identified as successful producers grown under test expression conditions for three days post induction in buffer minimal methanol (BMM) media. rHSA$_{WT}$ was expressed for three days in BMMY for comparison (FIG. 6f). FIG. 6f provides the results of experiments performed to test the expression of rHSA$_{E37X}$ in the presence (+) and absence (−) of unnatural amino acids. 25 µl of unpurified cleared media from each protein expression was analyzed on an SDS-PAGE gel and stained with Coomassie. Lane 4 is expression of rHSA$_{WT}$, also after three days.

Figure 13:
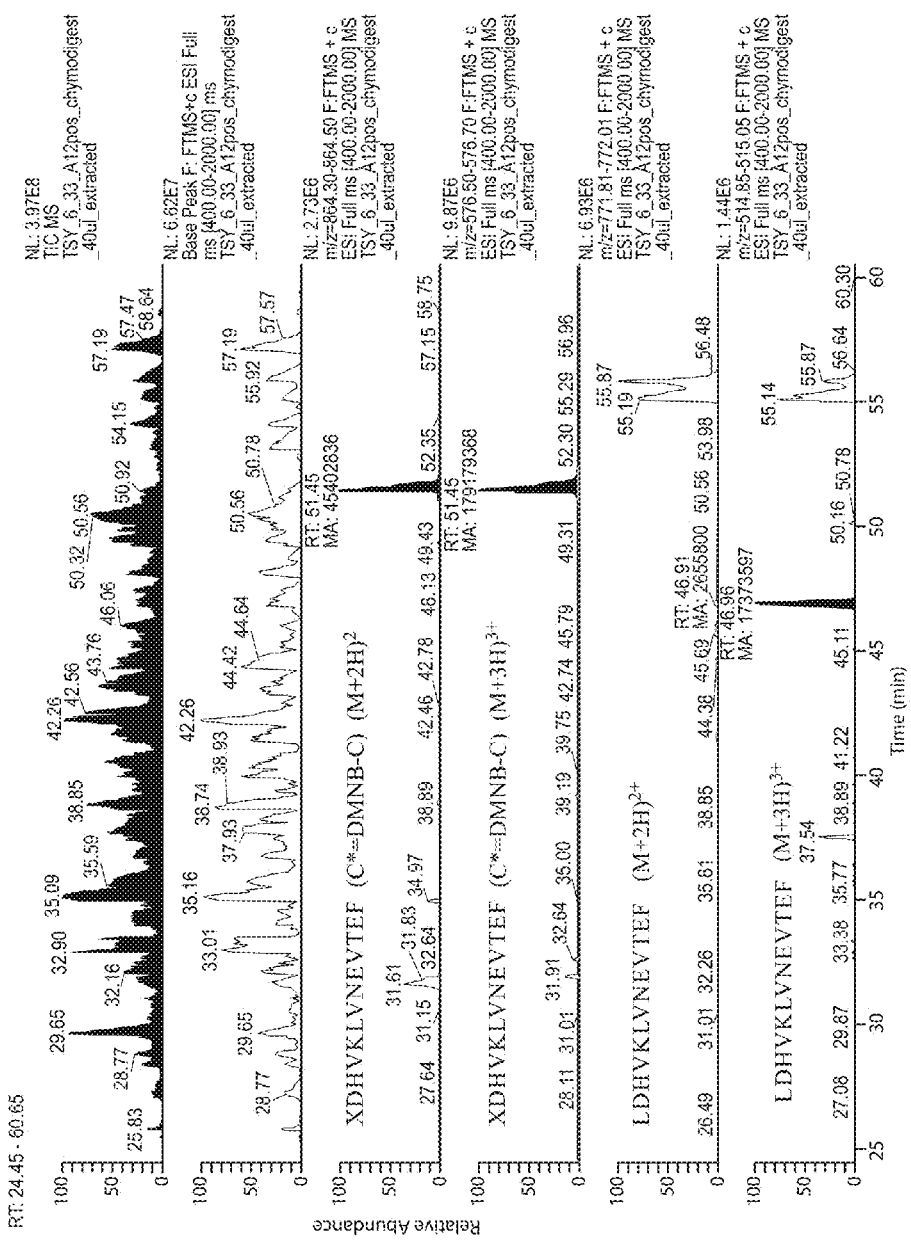
FIG. 13 shows LC-MS/MS of chymotrypsin-digested rHSA$_{E37DMNB-C}$ protein from lane 2 of FIG. 6*f*.

The LeuRS mutant specific for DMNB-S was recently shown to accept the cysteine analog of DMNB-S (DMNB-C), which was used in these expression experiments due to easier synthetic accessibility. Although small amounts of full-length protein (a background of 35% of rHSA$_{E37DMNB-S}$ for DMNB-S and 6% of rHSA$_{E37dansyl}$ for dansyl) were produced in the absence of the cognate amino acid, LC-MS/MS of a tryptic digest confirmed high fidelity of the system in the presence of the corresponding unnatural amino acid (FIG. 13). As shown in FIG. 13, rHSA$_{E37DMNB-C}$ protein from lane 2 of FIG. 6f was subjected to tryptic digest followed by LC-MS/MS as described above, except chymotrypsin replaced trypsin in the digest. The top chromatogram (black) illustrates the total ion count (TIC) for the LC-MS/MS run between minutes 24.45, and 60.05. The third and fourth chromatograms are ion extractions for the 2+ and 3+ charged species, respectively, corresponding to chymotryptic peptide, XDHVKLVNEVTEF (SEQ ID NO: 44), where X (the 37$^{th}$ residue of rHSA) is DMNB-C (total area under the peaks, "MA"=224582204). The fifth and sixth chromatograms are ion extractions for the 2+ and 3+ charged species, respectively, corresponding to chymotryptic peptide, XDHVKLVNEVTEF (SEQ ID NO: 45), where X is isoleucine or leucine (total area under the peaks "MA"=20029397). Calculations were done as follows: percent E37DMNB-C=224582204/(224582204+20029397)*100=91.8% and percent E37L=20029397/(224582204+20029397)*100=8.2%. Ion species corresponding to the incorporation of other natural amino acids at X were not detected in appreciable amounts.

Indeed, nonspecific readthrough of a nonsense codon is often suppressed by the presence of an aminoacylated suppressor tRNA. Suppression yields were approximately 37% the yield of rHSA$_{WT}$ for rHSA$_{E37DMNB-C}$ and 23% the yield of rHSA$_{WT}$ for rHSA$_{E37dansyl}$ after three days of expression.

Previous attempts to optimize the expression of proteins containing unnatural amino acids in S. cerevisiae resulted in maximal yields of 8-15 mg L$^{−1}$ in model systems, more than an order of magnitude less than demonstrated in the P. pastoris system developed here. Work in the Wang laboratory has recently shown that knockdown of the nonsense-mediated mRNA decay (NMD) pathway in yeast can increase protein expression up to 2-fold (Wang and Wang (2008) "New methods enabling efficient incorporation of unnatural amino acids in yeast." J Am Chem Soc 130: 6066-6067). Coupled with the use of a promoter derived from SNR52 to drive tRNA$_{CUA}$ transcription, they were able to achieve yields 300-fold higher yields of mutant protein than previously produced in S. cerevisiae, approximately 15 mg L$^{−1}$ (Wang and Wang (2008) "New methods enabling efficient incorporation of unnatural amino acids in yeast." J Am Chem Soc 130: 6066-6067). Thus, knockout of the UPF1 gene of the NMD pathway and use of the SNR52-tRNA$_{CUA}$ promoter system may further increase yields in P. pastoris. Additionally, work in the Kobayashi laboratory has demonstrated that yields of rHSA$_{WT}$ from P. pastoris are more than an order of magnitude better (>10 g L$^{−1}$) when expressed in fed-batch fermentation rather than in standard shake flasks (Ohya (2005) "Optimization of human serum albumin production in methylotrophic yeast Pichia pastoris by repeated fed-batch fermentation." Biotechnol Bioeng 90: 876-887).

In summary, we have extended the methodology for the biosynthetic incorporation of unnatural amino acids into methylotrophic yeast. Two aaRS/tRNA$_{CUA}$ pairs were shown to be orthogonal in P. pastoris and used to express mutant proteins with eight different unnatural amino acids in response to an amber codon at residue 37 of rHSA$_{E37X}$. Mutant proteins were expressed at high levels in shake flasks with excellent fidelities. These results suggest that this expression system is amenable to many other unnatural amino acids with synthetases currently being evolved in S. cerevisiae and is not limited to the unnatural amino acids or aaRS/tRNA$_{CUA}$ pairs discussed here. The high yields and fidelities of this new system make it possible to obtain useful amounts of therapeutic proteins with unique biological and pharmacological properties. For example, chemistries such as oxime ligation or the copper catalyzed 1,3-cycloaddition reaction ("click chemistry") can be exploited to site-specifically PEGylate or crosslink proteins, metal ion binding amino acids can be incorporated to bind radioisotopes, and peptide, toxin, or siRNA conjugates can be made from carrier proteins such as HSA or targeting proteins such as antibodies. In addition, the aforementioned rHSA$_{E37pApa}$-ABT-510 conjugates are being tested in in vitro anti-angiogenesis assays. The use of rHSA$_{E37pApa}$ as an endogenous, non-immunogenic carrier can be applied to other rapidly cleared peptides including glucagon-like peptide 1 mimetics (GLP-1) and parathyroid hormone (PTH) peptides.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

Amino acid sequence of mature HSA (not including signal sequence or propeptide sequence) SEQ ID NO: 1

```
DAHKSE VAHRFKDLGE ENFKALVLIA FAQYLQQCPF EDHVKLVNEV TEFAKTCVAD ESAENCDKSL

HTLFGDKLCT VATLRETYGE MADCCAKQEP ERNECFLQHK DDNPNLPRLV RPEVDVMCTA

FHDNEETFLK KYLYEIARRH PYFYAPELLF FAKRYKAAFT ECCQAADKAA CLLPKLDELR

DEGKASSAKQ RLKCASLQKF GERAFKAWAV ARLSQRFPKA EFAEVSKLVT DLTKVHTECC

HGDLLECADD RADLAKYICE NQDSISSKLK ECCEKPLLEK SHCIAEVEND EMPADLPSLA
```

-continued

ADFVESKDVC KNYAEAKDVF LGMFLYEYAR RHPDYSVVLL LRLAKTYETT LEKCCAAADP

HECYAKVFDE FKPLVEEPQN LIKQNCELFE QLGEYKFQNA LLVRYTKKVP QVSTPTLVEV

SRNLGKVGSK CCKHPEAKRM PCAEDYLSVV LNQLCVLHEK TPVSDRVTKC CTESLVNRRP

CFSALEVDET YVPKEFNAET FTFHADICTL SEKERQIKKQ TALVELVKHK PKATKEQLKA

VMDDFAAFVE KCCKADDKET CFAEEGKKLV AASQAALGL

Amino acid sequence of mature TSP-1 (not including signal sequence) SEQ ID NO: 2

NR IPESGGDNSV FDIFELTGAA RKGSGRRLVK GPDPSSPAFR IEDANLIPPV

PDDKFQDLVD AVRAEKGFLL LASLRQMKKT RGTLLALERK DHSGQVFSVV SNGKAGTLDL

SLTVQGKQHV VSVEEALLAT GQWKSITLFV QEDRAQLYID CEKMENAELD VPIQSVFTRD

LASIARLRIA KGGVNDNFQG VLQNVRFVFG TTPEDILRNK GCSSSTSVLL TLDNNVVNGS

SPAIRTNYIG HKTKDLQAIC GISCDELSSM VLELRGLRTI VTTLQDSIRK VTEENKELAN

ELRRPPLCYH NGVQYRNNEE WTVDSCTECH CQNSVTICKK VSCPIMPCSN ATVPDGECCP

RCWPSDSADD GWSPWSEWTS CSTSCGNGIQ QRGRSCDSLN NRCEGSSVQT RTCHIQECDK

RFKQDGGWSH WSPWSSCSVT CGDGVITRIR LCNSPSPQMN GKPCEGEARE TKACKKDACP

INGGWGPWSP WDICSVTCGG GVQKRSRLCN NPTPQFGGKD CVGDVTENQI CNKQDCPIDG

CLSNPCFAGV KCTSYPDGSW KCGACPPGYS GNGIQCTDVD ECKEVPDACF NHNGEHRCEN

TDPGYNCLPC PPRFTGSQPF GQGVEHATAN KQVCKPRNPC TDGTHDCNKN AKCNYLGHYS

DPMYRCECKP GYAGNGIICG EDTDLDGWPN ENLVCVANAT YHCKKDNCPN LPNSGQEDYD

KDGIGDACDD DDDNDKIPDD RDNCPFHYNP AQYDYDRDDV GDRCDNCPYN HNPDQADTDN

NGEGDACAAD IDGDGILNER DNCQYVYNVD QRDTDMDGVG DQCDNCPLEH NPDQLDSDSD

RIGDTCDNNQ DIDEDGHQNN LDNCPYVPNA NQADHDKDGK GDACDHDDDN DGIPDDKDNC

RLVPNPDQKD SDGDGRGDAC KDDFDHDSVP DIDDICPENV DISETDFRRF QMIPLDPKGT

SQNDPNWVVR HQGKELVQTV NCDPGLAVGY DEFNAVDFSG TFFINTERDD DYAGFVFGYQ

SSSRFYVVMW KQVTQSYWDT NPTRAQGYSG LSVKVVNSTT GPGEHLRNAL WHTGNTPGQV

RTLWHDPRHI GWKDFTAYRW RLSHRPKTGF IRVVMYEGKK IMADSGPIYD KTYAGGRLGL

FVFSQEMVFF SDLKYECRDP

Amino acid sequence of ABT-510 peptide SEQ ID NO: 3

(N-Ac-Sar)-Gly-Val-(D-alloIle)-Thr-Nva-Ile-Arg- (Pro-NHEt)

---

SEQUENCE LISTING

<160> NUMBER OF SEQ ID NOS: 45

<210> SEQ ID NO 1
<211> LENGTH: 585
<212> TYPE: PRT
<213> ORGANISM: Homo sapiens

<400> SEQUENCE: 1

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 2
<211> LENGTH: 771
<212> TYPE: PRT
<213> ORGANISM: Homo sapiens

<400> SEQUENCE: 2

Asn Arg Ile Pro Glu Ser Gly Gly Asp Asn Ser Val Phe Asp Ile Phe
1               5                   10                  15

Glu Leu Thr Gly Ala Ala Arg Lys Gly Ser Gly Arg Arg Leu Val Lys
            20                  25                  30

Gly Pro Asp Pro Ser Ser Pro Ala Phe Arg Ile Glu Asp Ala Asn Leu
        35                  40                  45

Ile Pro Pro Val Pro Asp Asp Lys Phe Gln Asp Leu Val Asp Ala Val
    50                  55                  60

Arg Ala Glu Lys Gly Phe Leu Leu Leu Ala Ser Leu Arg Gln Met Lys
65                  70                  75                  80

Lys Thr Arg Gly Thr Leu Leu Ala Leu Glu Arg Lys Asp His Ser Gly
                85                  90                  95

Gln Val Phe Ser Val Val Ser Asn Gly Lys Ala Gly Thr Leu Asp Leu
            100                 105                 110

Ser Leu Thr Val Gln Gly Lys Gln His Val Val Ser Val Glu Glu Ala
        115                 120                 125

Leu Leu Ala Thr Gly Gln Trp Lys Ser Ile Thr Leu Phe Val Gln Glu
    130                 135                 140

Asp Arg Ala Gln Leu Tyr Ile Asp Cys Glu Lys Met Glu Asn Ala Glu
145                 150                 155                 160

Leu Asp Val Pro Ile Gln Ser Val Phe Thr Arg Asp Leu Ala Ser Ile
                165                 170                 175

Ala Arg Leu Arg Ile Ala Lys Gly Gly Val Asn Asp Asn Phe Gln Gly
            180                 185                 190

Val Leu Gln Asn Val Arg Phe Val Phe Gly Thr Thr Pro Glu Asp Ile
        195                 200                 205
```

```
Leu Arg Asn Lys Gly Cys Ser Ser Thr Ser Val Leu Thr Leu
    210                 215                 220

Asp Asn Asn Val Val Asn Gly Ser Ser Pro Ala Ile Arg Thr Asn Tyr
225                 230                 235                 240

Ile Gly His Lys Thr Lys Asp Leu Gln Ala Ile Cys Gly Ile Ser Cys
                245                 250                 255

Asp Glu Leu Ser Ser Met Val Leu Glu Leu Arg Gly Leu Arg Thr Ile
            260                 265                 270

Val Thr Thr Leu Gln Asp Ser Ile Arg Lys Val Thr Glu Glu Asn Lys
        275                 280                 285

Glu Leu Ala Asn Glu Leu Arg Arg Pro Pro Leu Cys Tyr His Asn Gly
    290                 295                 300

Val Gln Tyr Arg Asn Asn Glu Glu Trp Thr Val Asp Ser Cys Thr Glu
305                 310                 315                 320

Cys His Cys Gln Asn Ser Val Thr Ile Cys Lys Lys Val Ser Cys Pro
                325                 330                 335

Ile Met Pro Cys Ser Asn Ala Thr Val Pro Asp Gly Glu Cys Cys Pro
            340                 345                 350

Arg Cys Trp Pro Ser Asp Ser Ala Asp Asp Gly Trp Ser Pro Trp Ser
        355                 360                 365

Glu Trp Thr Ser Cys Ser Thr Ser Cys Gly Asn Gly Ile Gln Gln Arg
    370                 375                 380

Gly Arg Ser Cys Asp Ser Leu Asn Asn Arg Cys Glu Gly Ser Ser Val
385                 390                 395                 400

Gln Thr Arg Thr Cys His Ile Gln Glu Cys Asp Lys Arg Phe Lys Gln
                405                 410                 415

Asp Gly Gly Trp Ser His Trp Ser Pro Trp Ser Ser Cys Ser Val Thr
            420                 425                 430

Cys Gly Asp Gly Val Ile Thr Arg Ile Arg Leu Cys Asn Ser Pro Ser
        435                 440                 445

Pro Gln Met Asn Gly Lys Pro Cys Glu Gly Glu Ala Arg Glu Thr Lys
    450                 455                 460

Ala Cys Lys Lys Asp Ala Cys Pro Ile Asn Gly Gly Trp Gly Pro Trp
465                 470                 475                 480

Ser Pro Trp Asp Ile Cys Ser Val Thr Cys Gly Gly Gly Val Gln Lys
                485                 490                 495

Arg Ser Arg Leu Cys Asn Asn Pro Thr Pro Gln Phe Gly Gly Lys Asp
            500                 505                 510

Cys Val Gly Asp Val Thr Glu Asn Gln Ile Cys Asn Lys Gln Asp Cys
        515                 520                 525

Pro Ile Asp Gly Cys Leu Ser Asn Pro Cys Phe Ala Gly Val Lys Cys
    530                 535                 540

Thr Ser Tyr Pro Asp Gly Ser Trp Lys Cys Gly Ala Cys Pro Pro Gly
545                 550                 555                 560

Tyr Ser Gly Asn Gly Ile Gln Cys Thr Asp Val Asp Glu Cys Lys Glu
                565                 570                 575

Val Pro Asp Ala Cys Phe Asn His Asn Gly Glu His Arg Cys Glu Asn
            580                 585                 590

Thr Asp Pro Gly Tyr Asn Cys Leu Pro Cys Pro Pro Arg Phe Thr Gly
        595                 600                 605

Ser Gln Pro Phe Gly Gln Gly Val Glu His Ala Thr Ala Asn Lys Gln
    610                 615                 620
```

-continued

```
Val Cys Lys Pro Arg Asn Pro Cys Thr Asp Gly Thr His Asp Cys Asn
625                 630                 635                 640

Lys Asn Ala Lys Cys Asn Tyr Leu Gly His Tyr Ser Asp Pro Met Tyr
            645                 650                 655

Arg Cys Glu Cys Lys Pro Gly Tyr Ala Gly Asn Gly Ile Ile Cys Gly
            660                 665                 670

Glu Asp Thr Asp Leu Asp Gly Trp Pro Asn Glu Asn Leu Val Cys Val
            675                 680                 685

Ala Asn Ala Thr Tyr His Cys Lys Lys Asp Asn Cys Pro Asn Leu Pro
            690                 695                 700

Asn Ser Gly Gln Glu Asp Tyr Asp Lys Asp Gly Ile Gly Asp Ala Cys
705                 710                 715                 720

Asp Asp Asp Asp Asp Asn Asp Lys Ile Pro Asp Asp Arg Asp Asn Cys
                725                 730                 735

Pro Phe His Tyr Asn Pro Ala Gln Tyr Asp Tyr Asp Arg Asp Asp Val
            740                 745                 750

Gly Asp Arg Cys Asp Asn Cys Pro Tyr Asn His Asn Pro Asp Gln Ala
            755                 760                 765

Asp Thr Asp
    770

<210> SEQ ID NO 3
<211> LENGTH: 9
<212> TYPE: PRT
<213> ORGANISM: Artificial Sequence
<220> FEATURE:
<223> OTHER INFORMATION: ABT-510 peptide
<220> FEATURE:
<221> NAME/KEY: SITE
<222> LOCATION: (1)..(1)
<223> OTHER INFORMATION: n-acyl-sarcosine
<220> FEATURE:
<221> NAME/KEY: SITE
<222> LOCATION: (4)..(4)
<223> OTHER INFORMATION: D-allo-Isoleucine
<220> FEATURE:
<221> NAME/KEY: SITE
<222> LOCATION: (6)..(6)
<223> OTHER INFORMATION: norvaline
<220> FEATURE:
<221> NAME/KEY: SITE
<222> LOCATION: (9)..(9)
<223> OTHER INFORMATION: proline ethylamide

<400> SEQUENCE: 3

Xaa Gly Val Xaa Thr Xaa Ile Arg Xaa
1               5

<210> SEQ ID NO 4
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 4
gacagacctt accaaagtcc acacggaatg ctgccatg                            38

<210> SEQ ID NO 5
<211> LENGTH: 48
<212> TYPE: DNA
<213> ORGANISM: Artificial Sequence
<220> FEATURE:
<223> OTHER INFORMATION: Synthetic olgionucleotide
```

<400> SEQUENCE: 5
ggtaaggtct gtcactaact tggaaacttc tgcaaactca gctttggg                48

<210> SEQ ID NO 6
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 6
catggagacc tgcttgaatg tgctgatgac agggcgg                             37

<210> SEQ ID NO 7
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 7
caagcaggtc tccatggcag cattccgtgt ggac                                34

<210> SEQ ID NO 8
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 8
atccgaggat ccaaacgatg aagtgggtaa cctttatttc ccttcttttt c             51

<210> SEQ ID NO 9
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 9
gctaacgaat tcattataag cctaaggcag cttgacttgc agc                      43

<210> SEQ ID NO 10
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 10
gattgccttt gctcagtatc ttcagcagtg tccattttag gatcat                   46

<210> SEQ ID NO 11
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 11
gtttttgcaa attcagttac ttcattcact aattttacat gatcctaaaa tgg           53

<210> SEQ ID NO 12
<211> LENGTH: 48

```
<212> TYPE: DNA
<213> ORGANISM: Artificial Sequence
<220> FEATURE:
<223> OTHER INFORMATION: Synthetic oligonucleotide

<400> SEQUENCE: 12
taccactaga agcttggaga aaataccgca tcaggaaatt gtaaacgt                48

<210> SEQ ID NO 13
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 13
gtgagggcag gtaccgttct gtaaaaatgc agctcagatt ctttgtttg               49

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 14
aaatatggta cctgccctca cggtggttac ggt                                33

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 15
catttcaagc ttctagtggt aggaattctg taccggttta c                       41

<210> SEQ ID NO 16
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 16
atcgtactta aggaaagcgt actcaaacag acaaccattt cc                      42

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 17
ttctcaggcg cgccatcgcc cttcccaaca gttgcg                             36

<210> SEQ ID NO 18
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 18
```
catttcaaga ctgtcgcctt aaccactcgg ccat                34

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
gaaccagcgc gggcagagcc caacacattt caag                34

<210> SEQ ID NO 20
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 20
ctgcatcctt cgccttaacc actcggccat cgta                34

<210> SEQ ID NO 21
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 21
acacgagcag ggttcgaacc tgcgcgggca gagc                34

<210> SEQ ID NO 22
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 22
ggaaggattc gaaccttcga agtcgatgac gg                  32

<210> SEQ ID NO 23
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 23
tctgctccct ttggccgctc gggaacccca cc                  32

<210> SEQ ID NO 24
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 24
ttctgagaat tcaccatggc aagcagtaac ttgattaaac aattgc    46

<210> SEQ ID NO 25
<211> LENGTH: 66
<212> TYPE: DNA
<213> ORGANISM: Artificial Sequence

```
<220> FEATURE:
<223> OTHER INFORMATION: Synthetic oligonucleotide

<400> SEQUENCE: 25
taggctcggc cgcttagtgg tggtggtggt ggtgtttcca gcaaatcaga cagtaattct      60
ttttac                                                                66

<210> SEQ ID NO 26
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 26
atcgtactta agagatctaa catccaaaga cgaaaggttg aatgaaac                   48

<210> SEQ ID NO 27
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 27
tgcacaggcg cgccaagctt gcacaaacga acttctcact taatcttc                   48

<210> SEQ ID NO 28
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 28
gtatcgctta agtccaagat aggctatttt tgtcgcataa atttttgtc                  49

<210> SEQ ID NO 29
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 29
cgttagccat ggttttctca gttgatttgt ttgtggggat ttagtaagtc g               51

<210> SEQ ID NO 30
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 30
gtatcgctta agcatatgat gagtcacaat ctgcttccac agacgag                    47

<210> SEQ ID NO 31
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 31
```
cgttagccat gggactgcta ttatctctgt gtgtatgtgt gtattgggc        49

<210> SEQ ID NO 32
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 32
gtatcgctta aggaattcgg acaaatgtgc tgttccggta gcttg             45

<210> SEQ ID NO 33
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 33
cgttagccat ggtcttgata tacttgatac tgtgttcttt gaattgaaag        50

<210> SEQ ID NO 34
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 34
gtatcgctta aggcatgcag gaatctctgg cacggtgcta atgg              44

<210> SEQ ID NO 35
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 35
cgttagccat ggtgtgaata tcaagaattg tatgaacaag caaagttgg         49

<210> SEQ ID NO 36
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 36
gtatcgctta agggatcctt ttttgtagaa atgtcttggt gtcctcgtc         49

<210> SEQ ID NO 37
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 37
cgttagccat ggtgtgtttt gatagttgtt caattgattg aaataggggac       50

<210> SEQ ID NO 38
<211> LENGTH: 22
<212> TYPE: DNA
<213> ORGANISM: Artificial Sequence

```
<220> FEATURE:
<223> OTHER INFORMATION: Synthetic oligonucleotide

<400> SEQUENCE: 38
tgagacgctg cttaaccgct tc                                              22

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
taaagaagta ttcaggatcg gactg                                           25

<210> SEQ ID NO 40
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 40
aaggaagcta gcctcttttt caattgtata tgtg                                 34

<210> SEQ ID NO 41
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 41
cgtacacgcg tctgtacaga aaaaaagaa aaatttg                               37

<210> SEQ ID NO 42
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 42
attcacacca tggaagagca ataccgcccg gaagag                               36

<210> SEQ ID NO 43
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 43
ttaattcgcg gccgcttagc caacgaccag attgaggagt ttacctg                   47

<210> SEQ ID NO 44
<211> LENGTH: 13
<212> TYPE: PRT
<213> ORGANISM: Artificial Sequence
<220> FEATURE:
<223> OTHER INFORMATION: Fragment from tryptic digest of rHSA protein
      comprising the unnatural amino acid DMNB-C at amino acid position
      37 of HSA
<220> FEATURE:
<221> NAME/KEY: SITE
<222> LOCATION: (1)..(1)
```

```
<223> OTHER INFORMATION: DMNB-C

<400> SEQUENCE: 44

Xaa Asp His Val Lys Leu Val Asn Glu Val Thr Glu Phe
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Fragment from tryptic digest of rHSA protein
<220> FEATURE:
<221> NAME/KEY: SITE
<222> LOCATION: (1)..(1)
<223> OTHER INFORMATION: isoleucine or leucine

<400> SEQUENCE: 45

Xaa Asp His Val Lys Leu Val Asn Glu Val Thr Glu Phe
1               5                   10

=
```

What is claimed is:

1. A carrier polypeptide-target polypeptide conjugate comprising:
a carrier polypeptide domain comprising a first unnatural amino acid residue, wherein the carrier polypeptide domain comprises an antibody or antibody fragment; and,
a target polypeptide domain comprising a second unnatural amino acid residue;
wherein the carrier polypeptide domain and target polypeptide domain are conjugated together through the first and second unnatural amino acid residues;
wherein the first amino acid residue is incorporated into the antibody or antibody fragment, and/or the second unnatural amino acid residue is incorporated into the target polypeptide, in vivo in a methylotrophic yeast cell during translation using an orthogonal tRNA-synthetase/tRNA (O-RS/O-tRNA) pair derived from an *Escherichia coli* tyrosyl- or leucyl-tRNA synthetase/tRNA pair;
wherein the first or second unnatural amino acid comprises an azido moiety, an alkynyl moiety, or an alkenyl moiety; and
wherein the first and second unnatural amino acid are covalently coupled via a cycloaddition reaction.

2. The conjugate of claim 1, wherein the target polypeptide is a therapeutic peptide, or a peptide derivative of a therapeutic polypeptide.

3. The conjugate of claim 1, wherein the cycloaddition reaction is selected from the group consisting of a 1,3-cycloaddition reaction, a 1,3-dipolar cycloaddition reaction, a 2,3 cycloaddition reaction, an alkyne-azide cycloaddition reaction, and a Diels-Alder reaction.

4. The conjugate of claim 1, wherein the antibody or antibody fragment is selected from the group consisting of monoclonal antibodies, chimeric antibodies, humanized antibodies, Fab fragments, fragments produced by an Fab expression library, and single chain antibody fragments.

5. The conjugate of claim 1, wherein the antibody or antibody fragment is selected from the group consisting of a HER2 antibody, a HER2 antibody fragment, an OKT3 antibody, and an OKT3 antibody fragment.

6. The conjugate of claim 1, wherein the target polypeptide domain comprises one or more of: a TSP-1, an ABT-510, a glugacon-like peptide-1 (GLP-1), a parathyroid hormone (PTH), a ribosome inactivating protein (RIP), an angiostatin, an Exedin-4, an apoprotein, an atrial natriuretic factor, an atrial natriuretic polypeptide, an atrial peptide, a C—X—C chemokine, a T39765, a NAP-2, an ENA-78, a gro-a, a gro-b, a gro-c, an IP-10, a GCP-2, a NAP-4, an a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, a RANTES, an 1309, an R83915, an R91733, a T58847, a D31065, a T64262, a CD40 ligand, a complement inhibitor, a cytokine, an epithelial neutrophil activating peptide-78, a GROα, a MGSA, a GROβ, a GROγ, a MIP1-α, a MIP1-β, an MCP-1, an epithelial neutrophil activating peptide, an erythropoietin (EPO), an exfoliating toxin, a fibroblast growth factor (FGF), an FGF21, a G-CSF, a gonadotropin, a growth factor, a Hirudin, an LFA-1, a human insulin, a human insulin-like growth factor (hIGF), an hIGF-I, an hIGF-II, a human interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a leukemia inhibitory factor, a neurturin, a PDGF, a peptide hormone, a pleiotropin, a pyrogenic exotoxin A, a pyrogenic exotoxin B, a pyrogenic exotoxin C, a relaxin, a somatostatin, a superoxide dismutase, a thymosin alpha 1, a human tumor necrosis factor (hTNF), a human tumor necrosis factor alpha, a human tumor necrosis factor beta, a Ras, a Tat, an inflammatory molecule, a signal transduction molecule, a bovine pancreatic trypsin inhibitor (BPTI), or a BP320 antigen.

7. The conjugate of claim 1, wherein the first unnatural amino acid is incorporated into the antibody or antibody fragment variant during translation.

8. The conjugate of claim 1, wherein the second unnatural amino acid is incorporated into the target polypeptide during synthesis.

9. The conjugate of claim 1, wherein the target polypeptide is a TSP-1 variant comprising the second unnatural amino acid.

10. The conjugate of claim 1, wherein the target polypeptide is an ABT-510 variant comprising the second unnatural amino acid.

11. The conjugate of claim 1, wherein the carrier or target polypeptide is produced in a *Candida* cell, a *Hansenula* cell, a *Pichia* cell, or a *Torulopsis* cell.

12. A composition comprising the conjugate of claim 1.

13. A cell comprising the conjugate of claim 1.

14. A method of producing in a methylotrophic yeast cell at least one antibody or antibody fragment comprising at least one unnatural amino acid, the method comprising:
   growing, in an appropriate medium, a methylotrophic yeast cell that comprises a nucleic acid that comprises at least one selector codon and encodes the at least one antibody or antibody fragment; wherein the medium comprises the at least one unnatural amino acid and the methylotrophic yeast cell comprises:
   an orthogonal tRNA (O-tRNA) derived from an *Escherichia coli* tyrosyl- or leucyl-tRNA, that functions in the cell and recognizes the selector codon; and
   an orthogonal aminoacyl tRNA synthetase (O-RS) derived from an *Escherichia coli* tyrosyl- or leucyl-tRNA synthetase, that preferentially aminoacylates the O-tRNA with the at least one unnatural amino acid; and
   wherein the at least one unnatural amino acid comprises a moiety selected from the group consisting of: an azido moiety, an alkynyl moiety, and an alkenyl moiety.

15. An antibody or antibody fragment produced by the method of claim 14.

16. A method of producing a covalently coupled antibody-target polypeptide conjugate, the method comprising:
   incorporating a first unnatural amino acid residue into an antibody or antibody fragment during synthesis or translation of the antibody or antibody fragment;
   incorporating a second unnatural amino acid residue into a target polypeptide during synthesis or translation of the target polypeptide, wherein the antibody or antibody fragment, and/or the target polypeptide, is produced in a methylotrophic yeast cell during translation using an orthogonal tRNA-synthetase/tRNA (O-RS/O-tRNA) pair derived from an *Escherichia coli* tyrosyl- or leucyl-tRNA synthetase/tRNA pair; and,
   reacting the first and second unnatural amino acid residues to produce the covalently coupled antibody-target polypeptide conjugate;
   wherein the first or second unnatural amino acid comprises a moiety selected from the group consisting of: an azido moiety, an alkynyl moiety, and an alkenyl moiety; and
   wherein the first and second unnatural amino acid are covalently coupled via a cycloaddition reaction.

17. The method of claim 16, wherein the cycloaddition reaction is selected from the group consisting of: a 1,3-cycloaddition reaction, a 1,3-dipolar cycloaddition reaction, a 2,3 cycloaddition reaction, an alkyne-azide cycloaddition reaction, and a Diels-Alder reaction.

18. The method of claim 16, wherein the first or second unnatural amino acid is a photoreactive or radioactive amino acid.

19. The method of claim 16, wherein the carrier or target polypeptide is produced in a *Candida* cell, a *Hansenula* cell, a *Pichia* cell, or a *Torulopsis* cell.

20. An antibody conjugate produced by the method of claim 16.

21. The antibody conjugate of claim 20, wherein the antibody or antibody fragment is selected from the group consisting of monoclonal antibodies, chimeric antibodies, humanized antibodies, Fab fragments, a fragment produced by an Fab expression library, and single chain antibody fragments.

\* \* \* \* \*